(12) United States Patent
Kyriakides et al.

(10) Patent No.: US 12,186,452 B2
(45) Date of Patent: Jan. 7, 2025

(54) COMPOSITIONS AND METHODS USEFUL IN REGENERATIVE MEDICINE

(71) Applicant: YALE UNIVERSITY, New Haven, CT (US)

(72) Inventors: Themis Kyriakides, Branford, CT (US); Aaron Morris, Ann Arbor, MI (US)

(73) Assignee: Yale University, New Haven, CT (US)

( * ) Notice: Subject to any disclaimer, the term of this patent is extended or adjusted under 35 U.S.C. 154(b) by 74 days.

(21) Appl. No.: 16/757,811

(22) PCT Filed: Oct. 19, 2018

(86) PCT No.: PCT/US2018/056710
§ 371 (c)(1),
(2) Date: Apr. 21, 2020

(87) PCT Pub. No.: WO2019/083842
PCT Pub. Date: May 2, 2019

(65) Prior Publication Data
US 2021/0308327 A1 Oct. 7, 2021

Related U.S. Application Data

(60) Provisional application No. 62/575,595, filed on Oct. 23, 2017.

(51) Int. Cl.
| | | |
|---|---|---|
| *A61L 27/36* | (2006.01) | |
| *A61K 9/06* | (2006.01) | |
| *A61K 35/28* | (2015.01) | |
| *A61K 35/32* | (2015.01) | |
| *A61K 35/33* | (2015.01) | |
| *A61K 35/34* | (2015.01) | |
| *A61K 35/545* | (2015.01) | |
| *A61K 45/06* | (2006.01) | |
| *A61L 27/52* | (2006.01) | |
| *A61L 27/54* | (2006.01) | |
| *A61P 17/02* | (2006.01) | |

(52) U.S. Cl.
CPC ............ *A61L 27/3633* (2013.01); *A61K 9/06* (2013.01); *A61K 35/28* (2013.01); *A61K 35/32* (2013.01); *A61K 35/33* (2013.01); *A61K 35/34* (2013.01); *A61K 35/545* (2013.01); *A61K 45/06* (2013.01); *A61L 27/52* (2013.01); *A61L 27/54* (2013.01); *A61P 17/02* (2018.01)

(58) Field of Classification Search
None
See application file for complete search history.

(56) References Cited

U.S. PATENT DOCUMENTS

| | | | |
|---|---|---|---|
| 5,643,712 A | 7/1997 | Brasile | |
| 6,333,194 B1 * | 12/2001 | Levy | A61K 47/42 435/6.12 |
| 11,191,872 B2 | 12/2021 | Kyriakides et al. | |
| 2009/0318334 A1 | 12/2009 | Varadhachary et al. | |
| 2014/0220548 A1 | 8/2014 | Brasile | |
| 2016/0000834 A1 | 1/2016 | Kinsey et al. | |
| 2017/0182221 A1 * | 6/2017 | Benny | A61L 27/3633 |
| 2022/0152273 A1 | 5/2022 | Kyriakides et al. | |

FOREIGN PATENT DOCUMENTS

| | | |
|---|---|---|
| WO | 9421116 A1 | 9/1994 |
| WO | 0209735 A2 | 2/2002 |
| WO | 2014189835 A2 | 11/2014 |
| WO | 2017189480 A1 | 11/2017 |

OTHER PUBLICATIONS

Rijal G. The decellularized extracellular matrix in regenerative medicine. Regen Med. Jul. 2017;12(5):475-477. (Year: 2017).*
Calabro et al. Angiogenesis 17(1):291-292. Abstract presented at meeting Oct. 2013 (Year: 2013).*
Crapo et al. Biomaterials 2011 32(12):3233-3243 (Year: 2011).*
Omura et al. British Journal of Oral and Maxillofacial Surgery 35:85-91, 1997 (Year: 1997).*
Printout from the NIH-NCI website. https://www.cancer.gov/publications/dictionaries/cancer-terms/def/extracellular-matrix. Printed Mar. 9, 2023. one page. (Year: 2023).*
Calabro et al. Biochim Biophys Acta 1840(8):2396-2402, 2014 (Year: 2014).*
Google printout from google.com/search, printed Mar. 25, 2023 pp. 1-2.*
International Search Report and Written Opinion for PCT International Application No. PCT/US2018/056710 issued Feb. 6, 2019.
Addison , et al., "Inositol hexakisphosphate inhibits mineralization of MC3T3-E1 osteoblast cultures", Bone 46(4), Apr. 2010, 1100-1107.
Attwood , et al., "Measurement of the Interaction Between Recombinant I-domain From Integrin Alpha 2 Beta 1 and a Triple Helical Collagen Peptide With the GFOGER Binding Motif Using Molecular Force Spectroscopy", Int J Mol Sci. 14(2), Jan. 2013, 2832-2845.

(Continued)

*Primary Examiner* — Marcia S Noble
(74) *Attorney, Agent, or Firm* — Saul Ewing, LLP; Alireza Behrooz; Kathryn Doyle

(57) ABSTRACT

The present invention relates in part to compositions and methods for treating a wound, or location of interest, in mammal by administering a decellularized extracellular matrix (ECM) lacking thrombospondin-2 (TSP-2-null ECM). In certain embodiments, the invention provides an acellular composition comprising a decellularized TSP-2-null ECM. In certain embodiments, the invention provides a tunable hydrogel comprising a decellularized TSP-2-null ECM. The invention also provides, in certain embodiments, methods for accelerating cellular migration, methods for enhancing cellular invasion, methods for enhancing vascular growth and maturation of a region to be treated, and/or methods for enhancing a wound repair in a mammal in need thereof.

9 Claims, 53 Drawing Sheets

(56) References Cited

OTHER PUBLICATIONS

Bancroft, et al., "Up-regulation of thrombospondin-2 in Akt1-null mice contributes to compromised tissue repair due to abnormalities in fibroblast function", J Biol Chem. 290(1), Jan. 2015, 409-422.
Bourgine, et al., "Engineered Extracellular Matrices as Biomaterials of Tunable Composition and Function", Adv. Funct. Mater. 27(7), Jan. 2017, Abstract only.
Calabro, et al., "Thrombospondin-2 and extracellular matrix assembly", Biochim Biophys Acta. 1840(8), Aug. 2014, 2396-2402.
Dearth, et al., "A Rodent Model to Evaluate the Tissue Response to a Biological Scaffold When Adjacent to a Synthetic Material", Tissue Eng Part A. 21(19-20), Oct. 2015, 2526-2535.
Dreifuss, et al., "Acellular micronized extracellular matrix and occlusive dressings for open fingertip injuries", Plast Aesthet Res 2015;2:, 2015, 282-283.
Freytes, et al., "Preparation and rheological characterization of a gel form of the porcine urinary bladder matrix", Biomaterials 29(11), Apr. 2008, 1630-1637.
Gilbert, et al., "Production and characterization of ECM powder: implications for tissue engineering applications", Biomaterials 26(12), Apr. 2005, 1431-1435.
Hwang, et al., "Molecular assessment of collagen denaturation in decellularized tissues using a collagen hybridizing peptide", Acta Biomater. 53, Apr. 2017, 268-278.
Kee, et al., "Platelet Mechanosensing of Collagen Matrices", PLoS One. 10(4), Apr. 2015, e0126624.
Kobsa, et al., "An electrospun scaffold integrating nucleic acid delivery for treatment of full-thickness wounds", Biomaterials 34(15), May 2013, 3891-3901.
Krady, et al., "Thrombospondin-2 Modulates Extracellular Matrix Remodeling During Physiological Angiogenesis", Am J Pathol. 173(3), Sep. 2008, 879-891.
Kristofik, et al., "Improving in vivo outcomes of decellularized vascular grafts via incorporation of a novel extracellular matrix", Biomaterials 141, Oct. 2017, 63-73.
Kyriakides, et al., "Accelerated wound healing in mice with a disruption of the thrombospondin 2 gene", J Invest Dermatol. 113(5), Nov. 1999, 782-787.
Kyriakides, et al., "Megakaryocytes Require thrombospondin-2 for Normal Platelet Formation and Function", Blood. 101(10), May 2003, 3915-3923.
Kyriakides, et al., "Mice that lack thrombospondin 2 display connective tissue abnormalities that are associated with disordered collagen fibrillogenesis, an increased vascular density, and a bleeding diathesis", J Cell Biol. 140(2), Jan. 1998, 419-430.
Lopresti, et al., "Host Response to Biomaterials: The Impact of Host Response on Biomaterial Selection", Academic Press, 2015, 53-73 (abstract only).
Moore, et al., "Loss of monocyte chemoattractant protein-1 alters macrophage polarization and reduces NFkB activation in the foreign body response", Acta Biomater. 11, Jan. 2015, 37-47.
Morris, et al., "Inadequate Processing of Decellularized Dermal Matrix Reduces Cell Viability In Vitro and Increases Apoptosis and Acute Inflammation In Vivo", Biores Open Access. 5(1), Jul. 2016, 177-187.
Morris, et al., "Matricellular Proteins and Biomaterials", Matrix Biol. 37, Jul. 2014, 183-191.
Morris, et al., "Multicompartment Drug Release System for Dynamic Modulation of Tissue Responses", Advanced Healthcare Materials 6(19), Jun. 2017, Abstract only.
Qiu, et al., "Platelet Mechanosensing of Substrate Stiffness During Clot Formation Mediates Adhesion, Spreading, and Activation", Proc Natl Acad Sci U S A. 111(40), Oct. 2014, 14430-14435.
Reing, et al., "Degradation products of extracellular matrix affect cell migration and proliferation", Tissue Eng Part A. 15(3), Mar. 2009, 605-614.
Roh, et al., "Small-diameter biodegradable scaffolds for functional vascular tissue engineering in the mouse model", Biomaterials. 29(10), Apr. 2008, 1454-1463.
Singelyn, et al., "Naturally derived myocardial matrix as an injectable scaffold for cardiac tissue engineering", Biomaterials 30(29), Oct. 2009, 5409-5416.
Soucy, et al., "Microelastic Properties of Lung Cell-Derived Extracellular Matrix", Acta Biomater. 7(1), Jan. 2011, 96-105.
Szántó, et al., "New Insights Into Von Willebrand Disease and Platelet Function", Semin Thromb Hemost. 38(1), Feb. 2012, 55-63 (Abstract Only).
Wise, et al., "Submucosal injection of micronized acellular dermal matrix: analysis of biocompatibility and durability", Plast Reconstr Surg. 120(5), Oct. 2007, 1156-1160.
Wolf, et al., "A hydrogel derived from decellularized dermal extracellular matrix", Biomaterials 33(29), Oct. 2012, 7028-7038.
Yoo, et al., "A Novel in Vitro Model of Lymphatic Metastasis From Colorectal Cancer", J Surg Res. 143(1), Nov. 2007, 94-98 (Abstract Only).
Zhu, et al., "Determination of Mechanical Properties of Soft Tissue Scaffolds by Atomic Force Microscopy Nanoindentation", J Biomech. 44(13), Sep. 2011, 2356-2361 (Abstract Only).

* cited by examiner

WT

TSP-2 KO

FITC-Dextran

COMPOSITIONS AND METHODS USEFUL IN REGENERATIVE MEDICINE

CROSS-REFERENCE TO RELATED APPLICATIONS

The present application is a 35 U.S.C. § 371 national phase application from, and claims priority to, International Application No. PCT/US2018/056710, filed Oct. 19, 2018, and published under PCT Article 21 (2) in English, which claims priority under 35 U.S.C. § 119 (e) to U.S. Provisional Patent Application No. 62/575,595, filed Oct. 23, 2017, all of which applications are hereby incorporated by reference in their entireties.

STATEMENT REGARDING FEDERALLY SPONSORED RESEARCH OR DEVELOPMENT

This invention was made with government support under HL107205 and GM072194 awarded by National Institutes of Health and under 1122492 awarded by National Science Foundation. The government has certain rights in the invention.

BACKGROUND OF THE INVENTION

The extracellular matrix (ECM) is a complex network of materials, such as proteins and polysaccharides, that are secreted locally by cells and remain closely associated with them. This non-cellular network of materials is present within all tissues and organs, and provides not only essential physical scaffolding for the cellular constituents, but also initiates crucial biochemical and biomechanical cues that are required for tissue morphogenesis, differentiation and homeostasis.

Regenerative material requires the use of biocompatible scaffolds. Examples of such scaffolds include decellularized materials, a class of biomaterials that present distinct advantages over synthetic materials. Such advantages include: existence of native ECM structure, retention of matrix-bound growth factors and other bioactive components, and a favorable host response. Nevertheless, decellularized materials are not without limitations. While synthetic materials can be engineered to fit almost any need, decellularized materials are difficult to customize, because they rely on a natural source (either animal tissues or cells grown in vitro).

Research efforts have included comminuting the decellularized materials into a powder, solubilizing them into a gel, perforating the ECM to create larger pores within the decellularized tissue, or removing some ECM components to customize the decellularized materials. Addition of exogenous factors to these materials provides an additional method to tune these materials. A number of components have been added to decellularized materials typically by incubating the materials in these factors including: matricellular proteins, hyaluronic acid (HA), heparin, VEGF, EGF, and bFGF.

Materials made from cell-derived matrix (CDM) inherently have more engineering controls. The type of cells and duration of their culture period can be controlled, as well as factors such as scaffold architecture and mechanical conditioning. Recent studies have focused on controlling cellular phenotype either genetically or pharmacologically to alter ECM production prior to decellularization. TSP-2 is an anti-angiogenic, matricellular protein that interacts not only with ECM proteins, but also with a variety of cell surface receptors including CD36, CD47, heparin sulfate proteoglycan, low-density lipoprotein receptor-related protein, and $\alpha_v\beta_3$. Investigations on TSP-2 knock-out (KO) mice have shown that TSP-2 KO phenotype is dominated by abnormalities in connective tissue and a platelet aggregation defect that manifests an abnormal bleeding tendency. However, the process of ECM assembly, and particularly the role of cells in this process, remain not well understood. Also, it remains unclear whether genetic manipulation can impart tunability to entire materials or to a more complex component of the ECM such as architecture or mechanics.

Hydrogels are materials composed of polymers swollen with water and can be fabricated with synthetic or natural starting materials. More recently, hydrogels derived from solubilized decellularized ECM have been investigated. These hydrogels are attractive because they are derived from intact decellularized tissues and should maintain a level of biochemical complexity not achievable with purified polymers. Further, they are injectable, moldable, and readily translate to a cell culture platform. Nevertheless, there remains a lack in the art for hydrogels constructed from CDM, let alone hydrogels with tunable ECM.

There is a need in the art for compositions and methods for generating tunable acellular matrices useful for regenerative medicine. The present invention addresses this need.

BRIEF SUMMARY OF THE INVENTION

In one aspect, the invention provides a method of promoting tissue regeneration in a site of a subject in need thereof. In certain embodiments, the method comprises administering an acellular composition comprising a decellularized extracellular matrix (ECM) lacking thrombospondin-2 (TSP-2-null ECM) to the site in the subject.

In certain embodiments, the method enhances at least one biological response at the treatment site, as compared to a site administered a wild ECM or an untreated site, wherein the at least one biological response is selected from the group consisting of cellular migration towards the treatment site, cellular invasion of the treatment site, vascular growth and maturation at the treatment site, and wound repair at the treatment site.

In certain embodiments, the decellularized TSP-2-null ECM is derived from at least one material selected from the group consisting of a primary matrix-producing cell, a fibroblast, an osteoblast, and a smooth muscle.

In certain embodiments, wherein the decellularized TSP-2-null ECM is comminuted.

In certain embodiments, the decellularized TSP-2-null ECM is formulated in at least one material selected from the group consisting of a silicone and a hydrogel.

In certain embodiments, the acellular composition further comprises a wild type ECM.

In certain embodiments, the acellular composition is administered by at least one method selected from the group consisting of subcutaneous and topical.

In certain embodiments, the subject suffers from at least one condition selected from the group consisting of diabetes, hernia, mastectomy, peripheral vascular disease, and neuropathy.

In certain embodiments, the subject is a mammal. In other embodiments, the subject is a human.

In another aspect, the invention also provides a composition comprising a decellularized extracellular matrix (ECM) lacking thrombospondin-2 (TSP-2-null ECM).

In certain embodiments, the composition is a hydrogel composition. In other embodiments, the composition further comprises at least one therapeutic agent selected from the group consisting of an immunosuppressive agent, an anti-inflammatory agent, an antimetabolite, an antibiotic, an antibody, a growth factor, a cytokine, a gene therapy, and an immunomodulator.

In certain embodiments, the decellularized TSP-2-null ECM is derived from a mammal. In other embodiments, the decellularized TSP-2-null ECM is derived from at least one material selected from the group consisting of a primary matrix-producing cell, a fibroblast, an osteoblast, and a smooth muscle.

In certain embodiments, the decellularized TSP-2-null ECM is derived from cells or tissue having a full or partial knock-out of the TSP-2 gene. In other embodiments, the decellularized TSP-2-null ECM is derived from cells or tissue wherein TSP-2 expression is downregulated via at least one method selected from the group consisting of RNA interference (RNAi), small hairpin RNA (shRNA) transfection, and Clustered Regularly Interspaced Short Palindromic Repeats (CRISPRs).

In certain embodiments, the composition further comprises wild decellularized ECM.

In certain embodiments, the decellularized TSP-2-null ECM comprises a lower overall concentration of collagen than wild-type ECM. In other embodiments, the decellularized TSP-2-null ECM comprises a higher concentration of at least one selected from collagen 4 and the alpha 1 chain of collagen 6, as compared to wild-type ECM.

In yet another aspect, the invention provides a composition comprising a cell-derived matrix (CDM) hydrogel comprising an extracellular matrix produced by cells cultured in an in vitro environment. In certain embodiments, the hydrogel is made by culturing one or more cells in a cell culture such that an extracellular matrix (ECM) is produced, decellularizing the cell culture such that the ECM remains substantially intact, optionally contacting the ECM with an acid protease, and forming a hydrogel from the ECM material.

In certain embodiments, the CDM hydrogel is derived from at least one cell type selected from the group consisting of dermal fibroblast cells, osteoblast cells, smooth muscle cells, cardiac fibroblasts, mesenchymal stem cells and embryonic stem cells.

In certain embodiments, the CDM hydrogel is derived from a wild-type cell line or a genetically modified cell line. In other embodiments, the CDM hydrogel is derived from a TSP-2 knockout cell line.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 1A shows a set of representative SEM demonstrating contrast between structures. FIG. 1B shows a set of representative H&E images indicating the absence of nuclear material in both constructs. FIGS. 1C-1D are a graph showing stress versus strain plots of tensile testing (FIG. 1C) and a diagram of dog bone-shaped cutouts (units in mm) (FIG. 1D). FIGS. 1E-1F are graphs showing the ultimate tensile strength (FIG. 1E) and elastic modulus (FIG. 1F) of WT and TSP-2 KO constructs. Results are given as mean+SEM, n=3, *p<0.05, **p<0.01.

FIG. 2A is a graph showing that TSP-2 KO decellularized skin constructs exhibited reduced collagen content as compared to WT by hydroxyproline assay (n=7). FIGS. 2B-2C are graphs showing that sGAG content (FIG. 2B) and residual DNA (FIG. 2C) were unchanged between genotypes (n=3). FIG. 2D is a graph comparing collagen denaturation between native skin, WT ADM, TSP-2 KO ADM and heat denatured intact skin. There was no difference in denaturation between WT and TSP-2 KO constructs compared to native skin. Each of these three exhibited significantly less denaturation than heat-denatured native skin (n=3). FIGS. 2E-2F are graphs of enzymatic degradation kinetics of WT and TSP-2 KO constructs. The results showed no difference in susceptibility between WT and TSP-2 KO constructs to either collagenase (FIG. 2E) or pepsin (FIG. 2F) (n=3). Results are given as mean+SEM, *p<0.05, ***p<0.0001.

FIGS. 3F-3G show the results of control migration experiments toward serum free and complete media performed for MC3T3-E1 and NIH/3T3. Results are given as mean+SEM, n=3, *p<0.05, ***p<0.005.

Figure 4B:
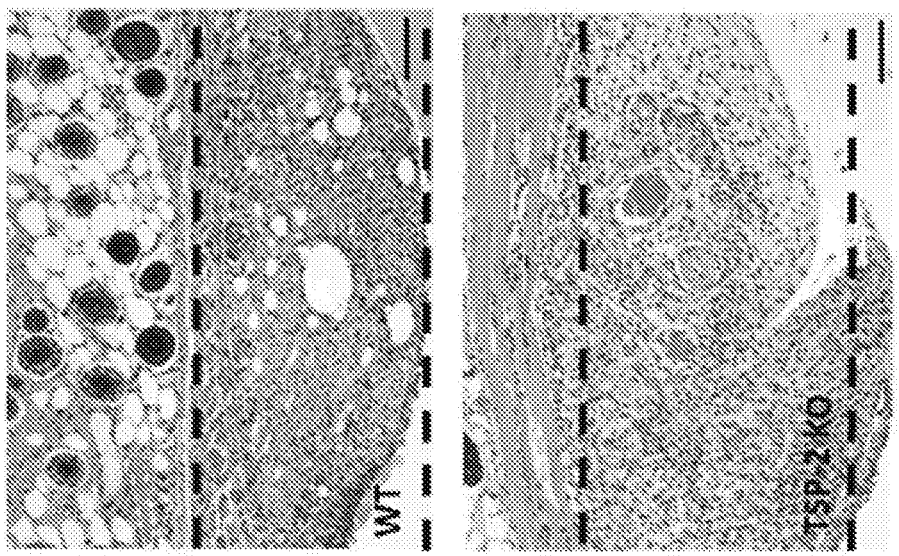
FIGS. 4A-4H are images and drafts showing that comminuted TSP-2 KO ADM promotes vascularization. SEM of WT and TSP-2 KO powdered ECM indicated difference in the structure of the grains, with WT appearing more shredded (FIG. 4A). After 14 days in vivo the powder was well invaded (FIG. 4B). Immunohistochemistry demonstrated more vascularization around the TSP-2 KO powder as demonstrated by CD31 (FIGS. 4C and 4H), αSMA (FIGS. 4D and 4H), Mac-3 and PCNA (FIG. 4H). There were more CD31-positive lumens (FIG. 4E) that were larger (FIG. 4F)
Figure 4A:
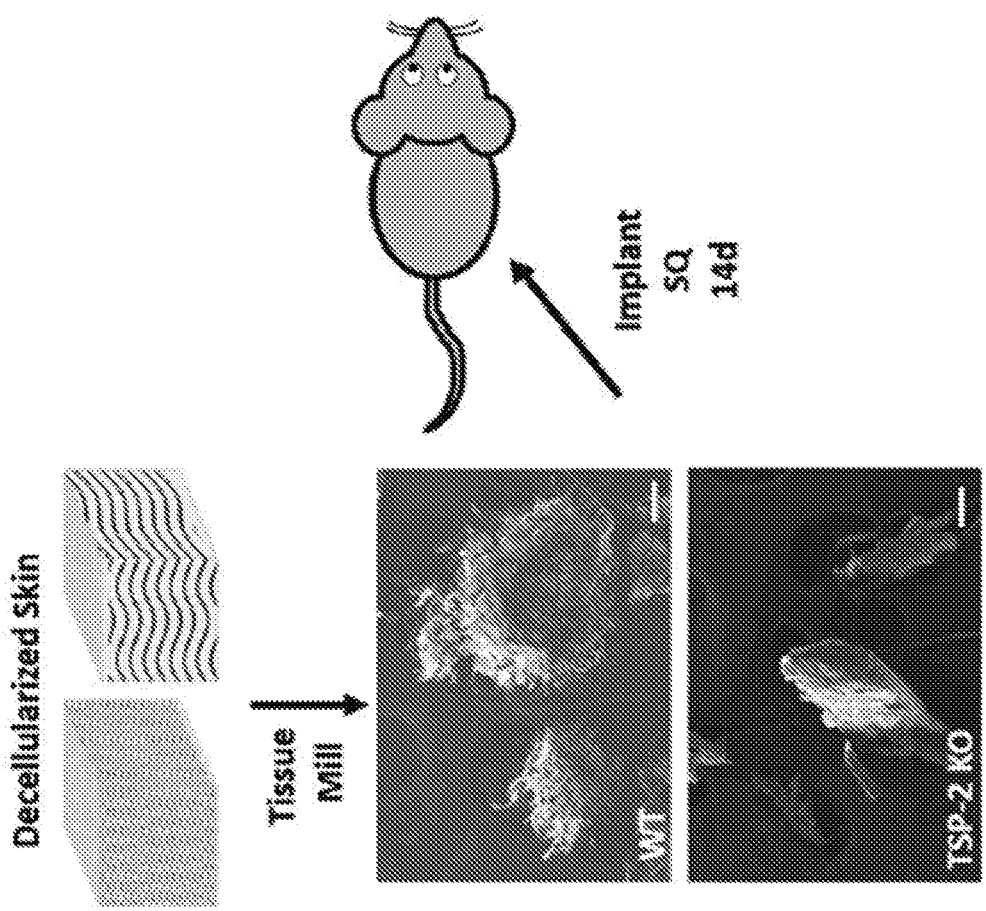
Figure 4C:
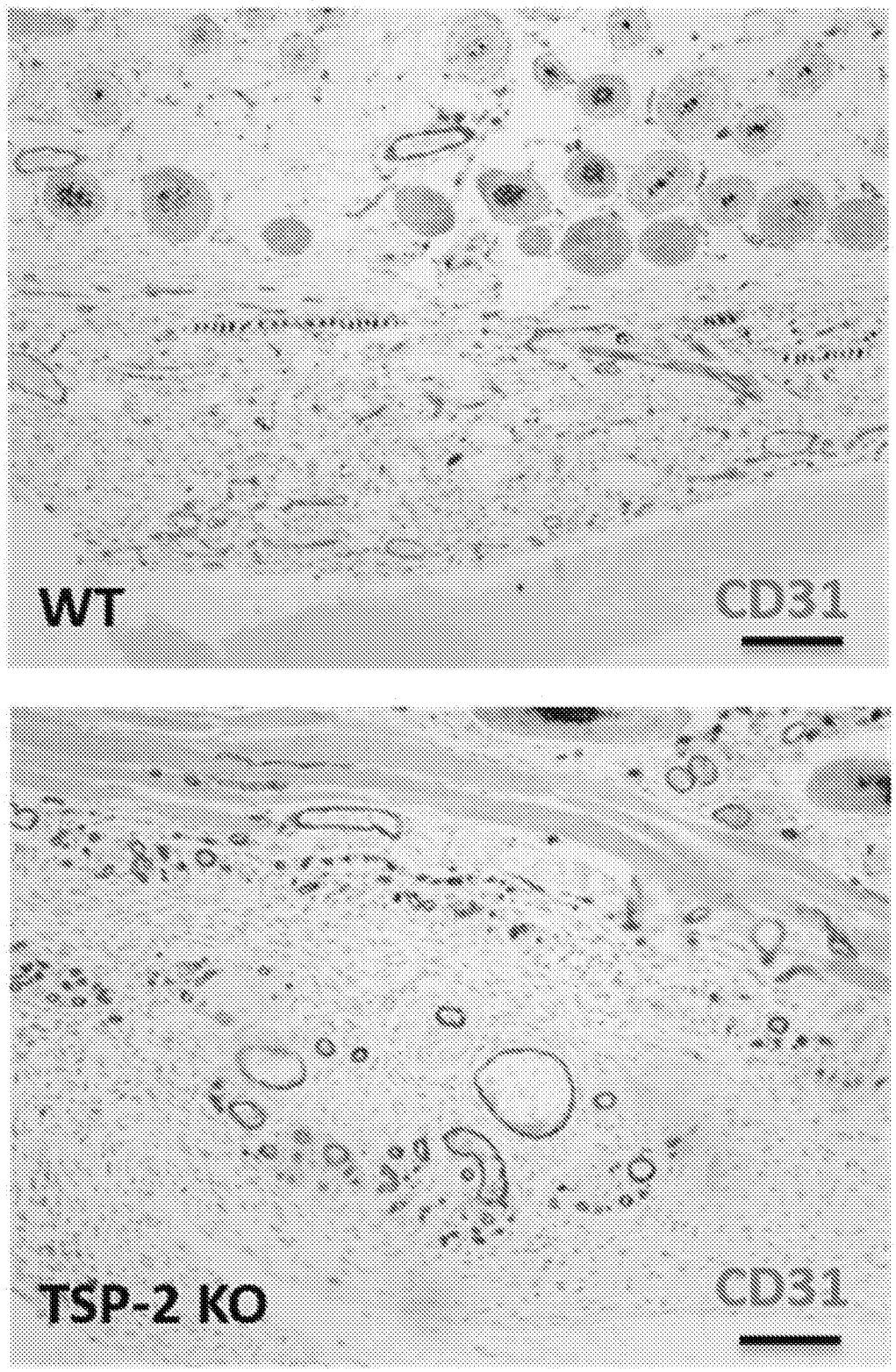
Figure 4D:
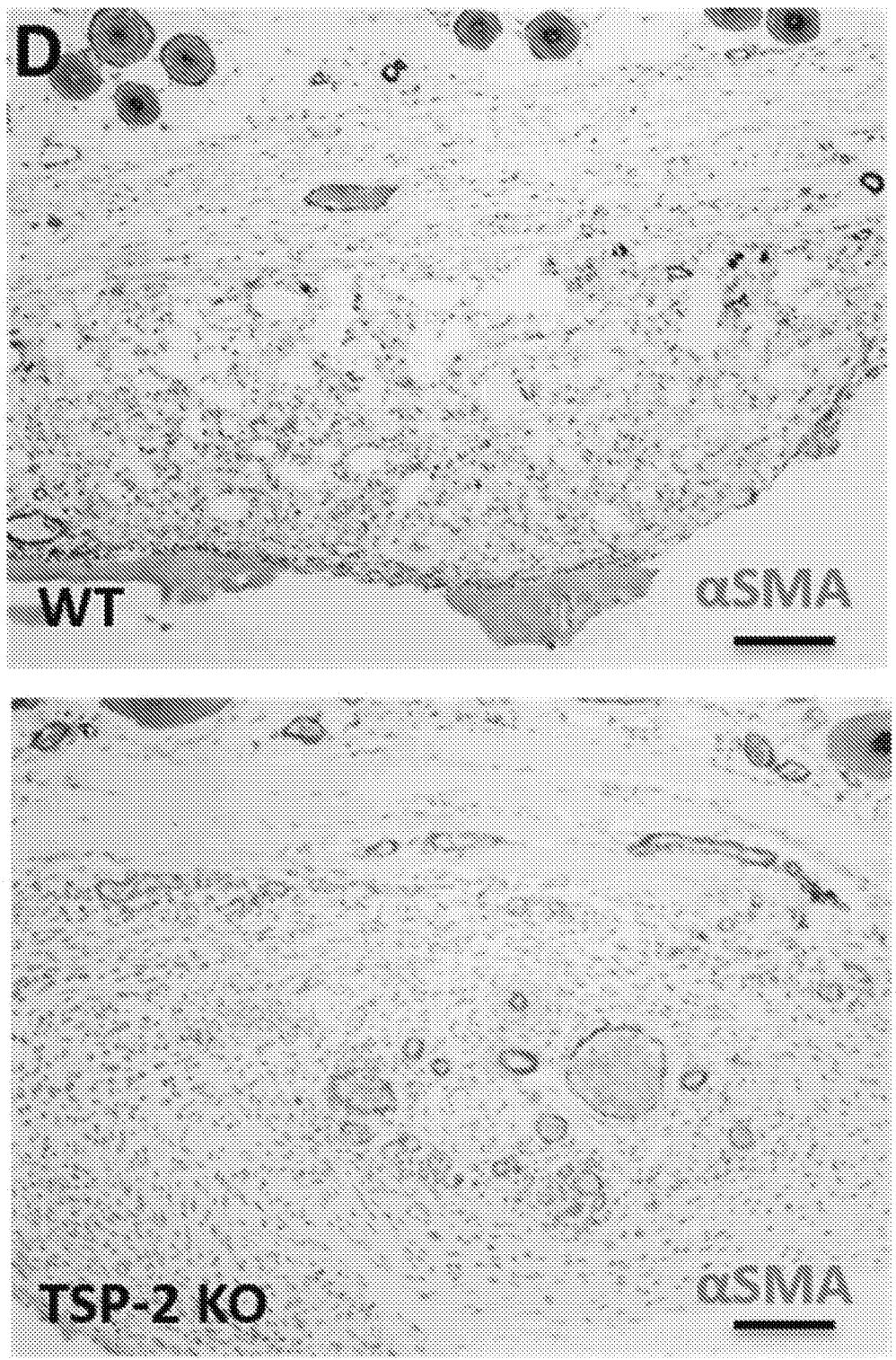
Figure 4E:
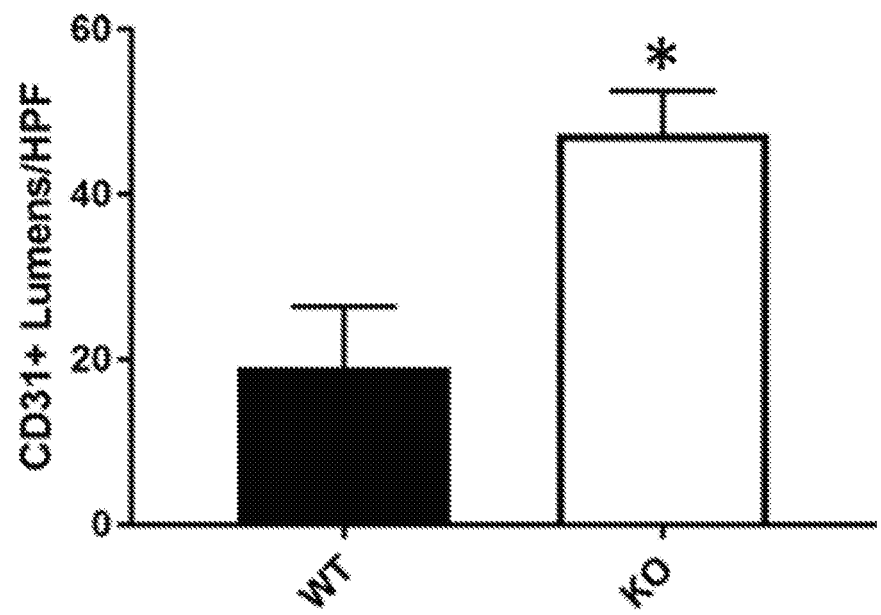
Figure 4F:
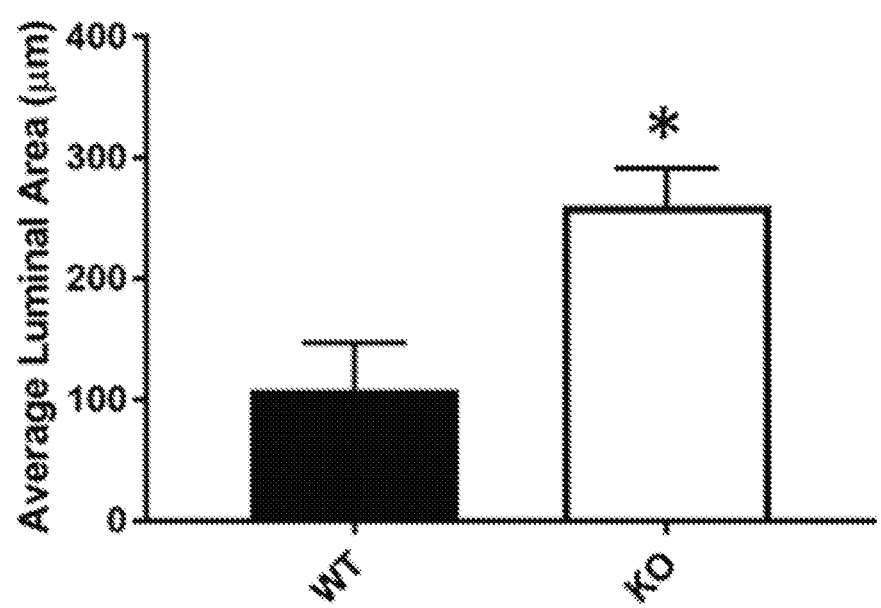
Figure 4G:
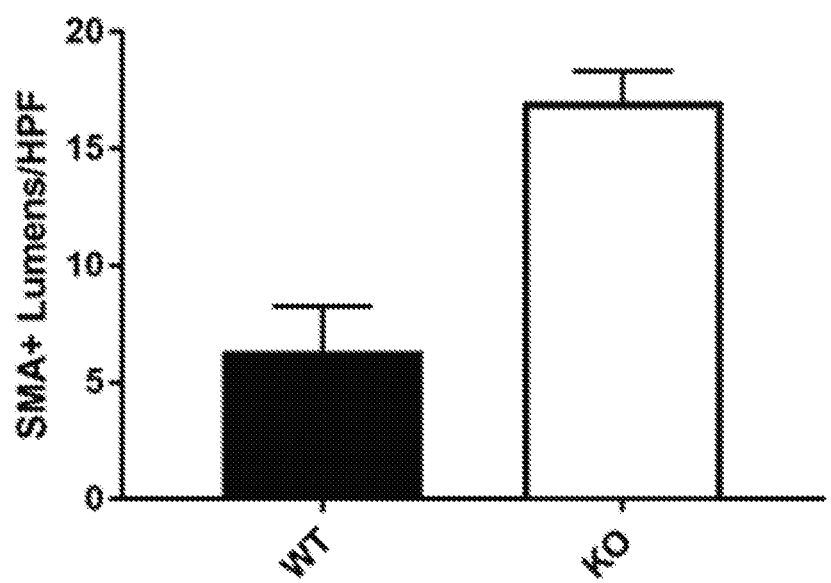
Figure 4H:
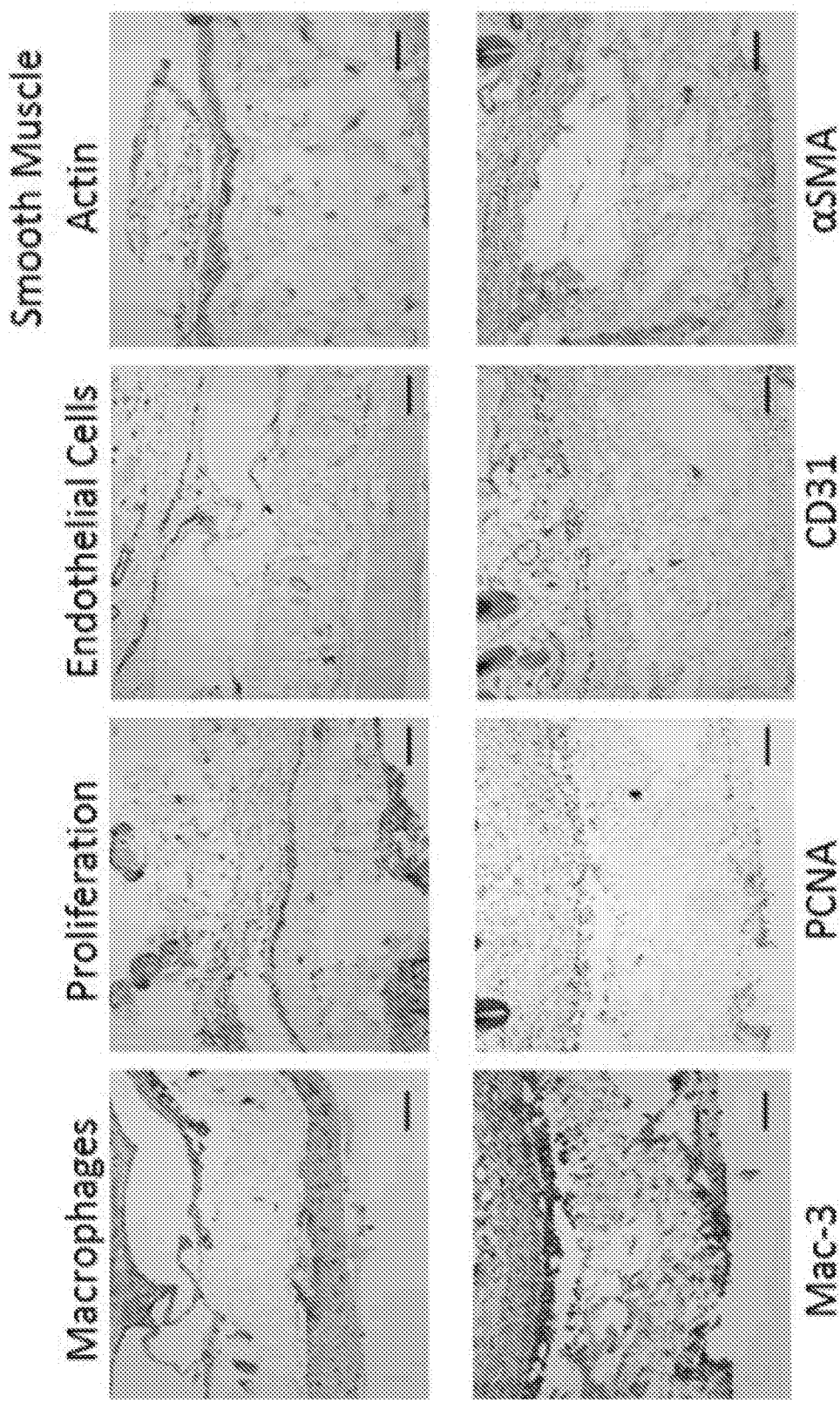

and more αSMA-positive (FIG. 4G). Scale bars=100 μm. Implanted silicone trays are out of frame but reside below and to the sides of the implanted ECM. ECM was just below the dermis. Results are given as mean+SEM, n=6, *p<0.05, ***p<0.005.

Figure 5A:
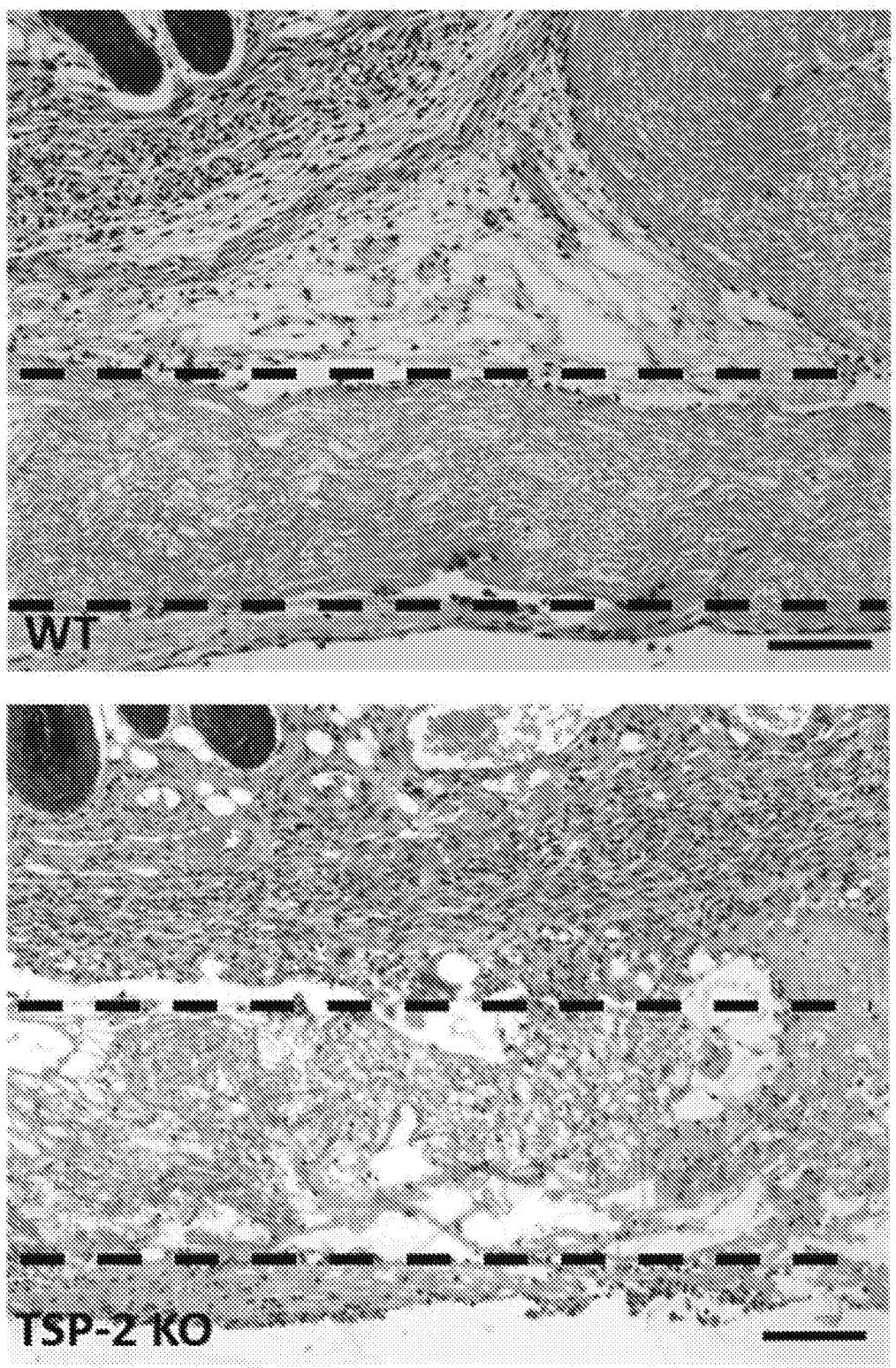
Figure 5B:
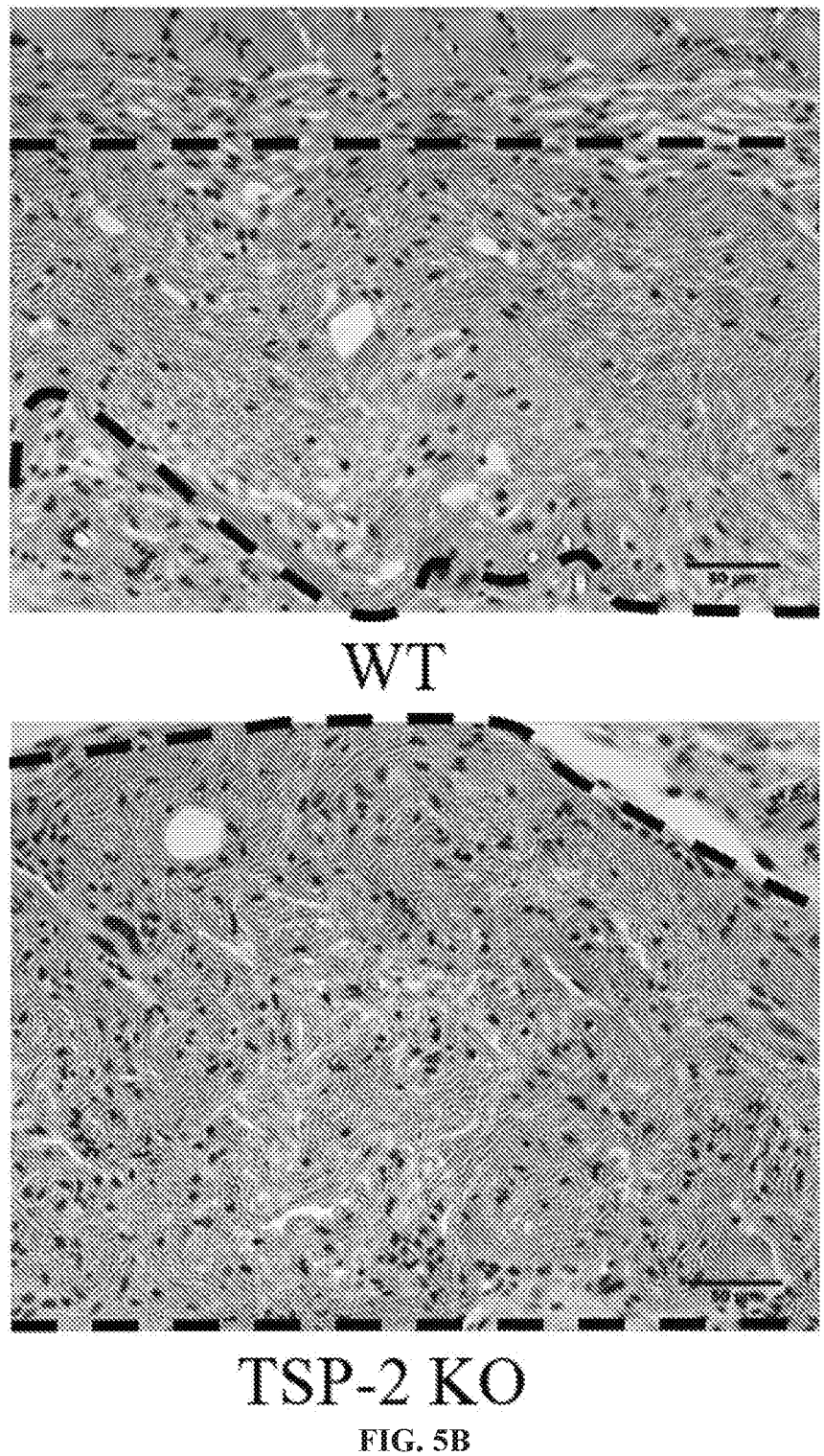
Figure 5C:
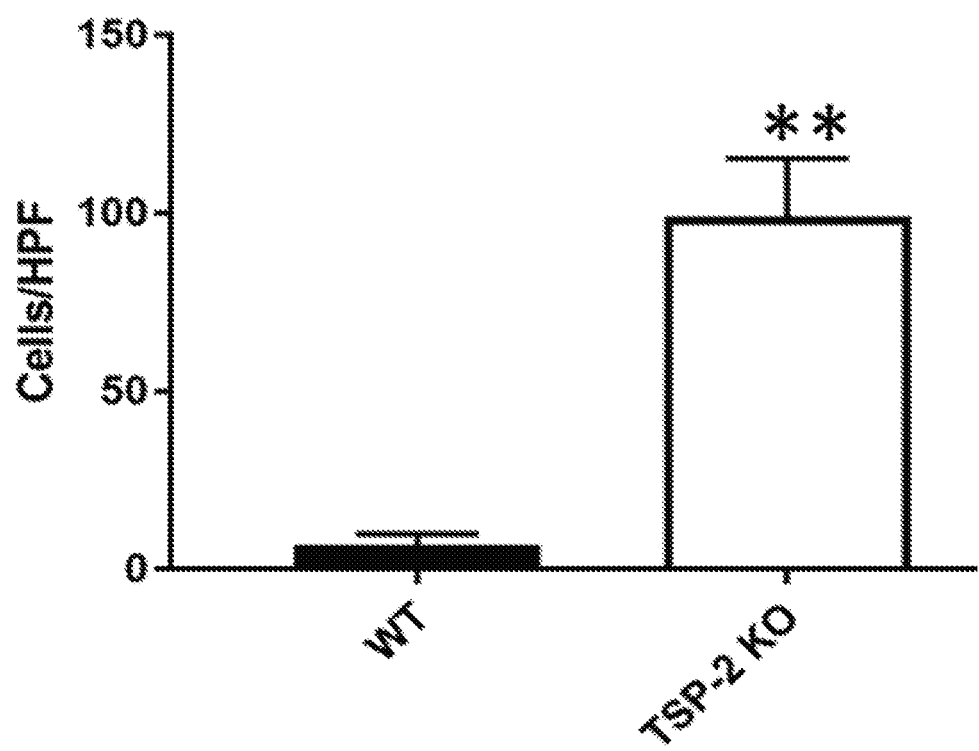
Figure 5D:
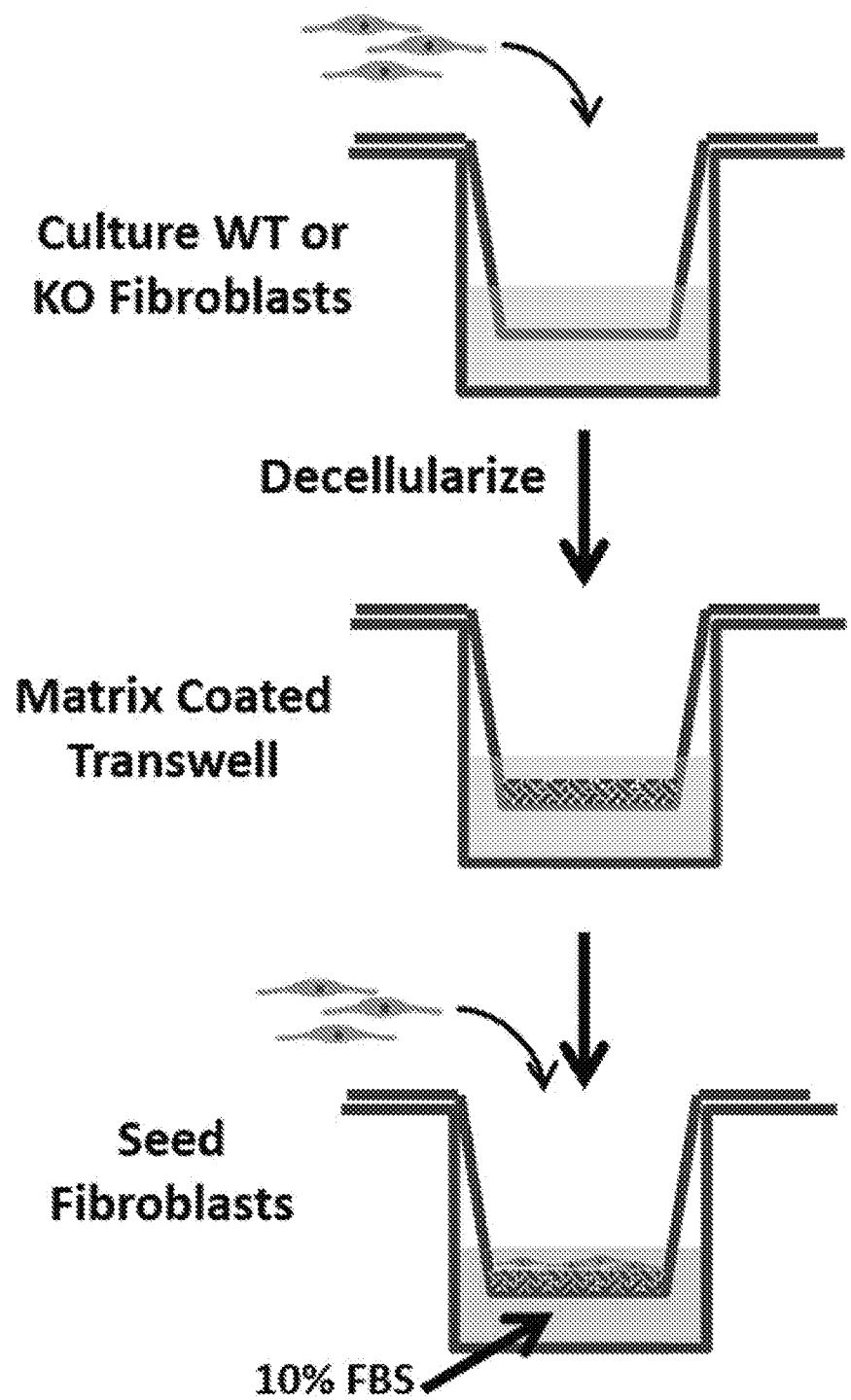
Figure 5E:
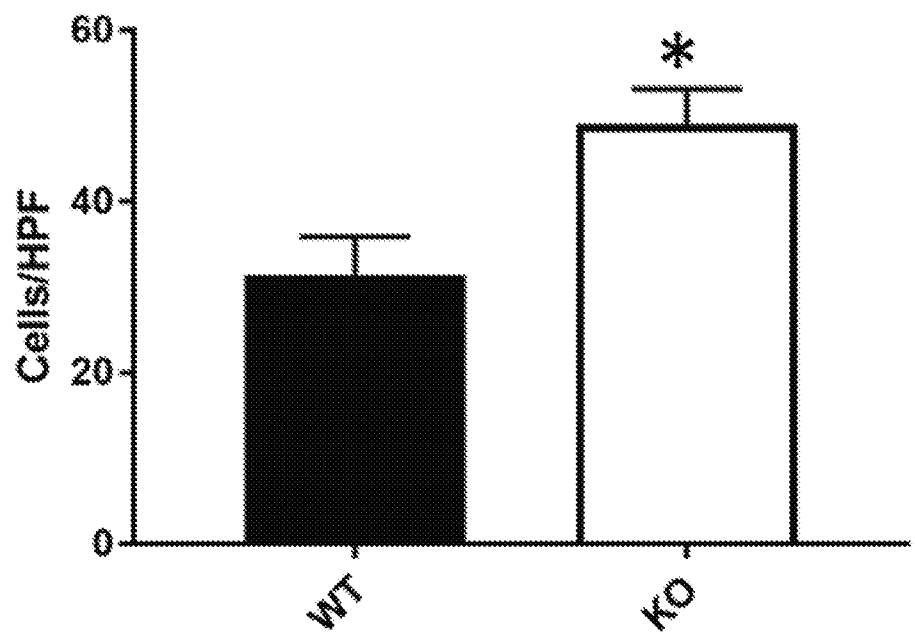
Figure 5F:
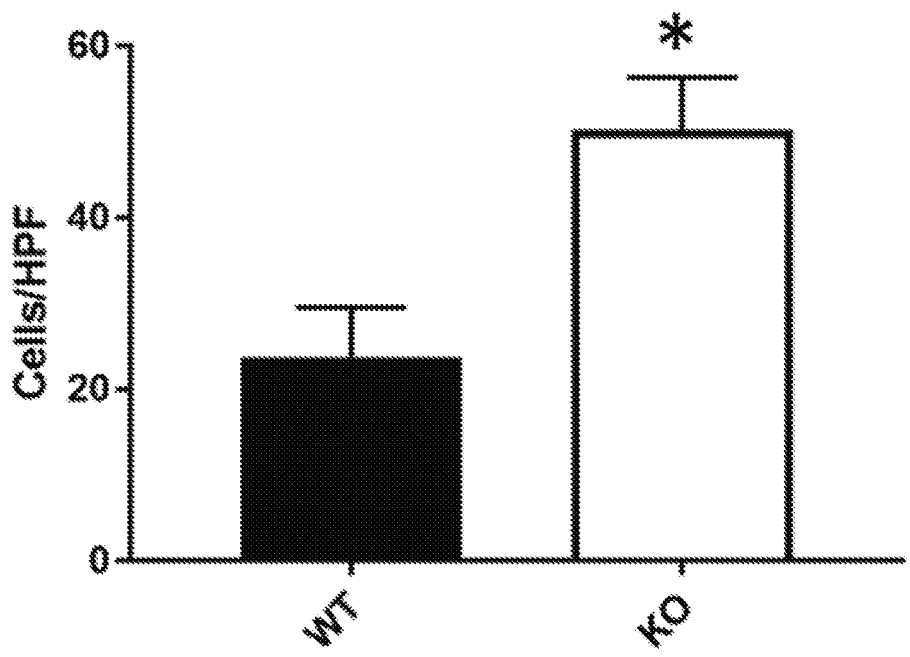

FIGS. 5A-5F are images, schemes and graphs showing that TSP-2 KO matrix promoted a pro-migratory environment. FIGS. 5A-5B are a set of images showing that intact slabs of constructs were implanted subcutaneously for 14 days, scale bar=100 μm, and TSP-2 KO constructs display increased cell penetration into the matrix. Implanted silicone trays are out of frame but reside below and to the sides of the implanted ECM; ECM was just below the dermis (n=4). FIG. 5C is a graph reporting cell migration. FIG. 5D is a scheme showing how cCDM was analyzed as an in vitro system to probe cell migration through WT and TSP-2 KO matrix. TSP-2 null ECM was more permissive to both WT and db/db fibroblast migration, n=5 (FIGS. 5E-5F). Scale bars=100 μm. Results are given as mean+SEM, *p<0.05, **p<0.01.

Figure 6A:
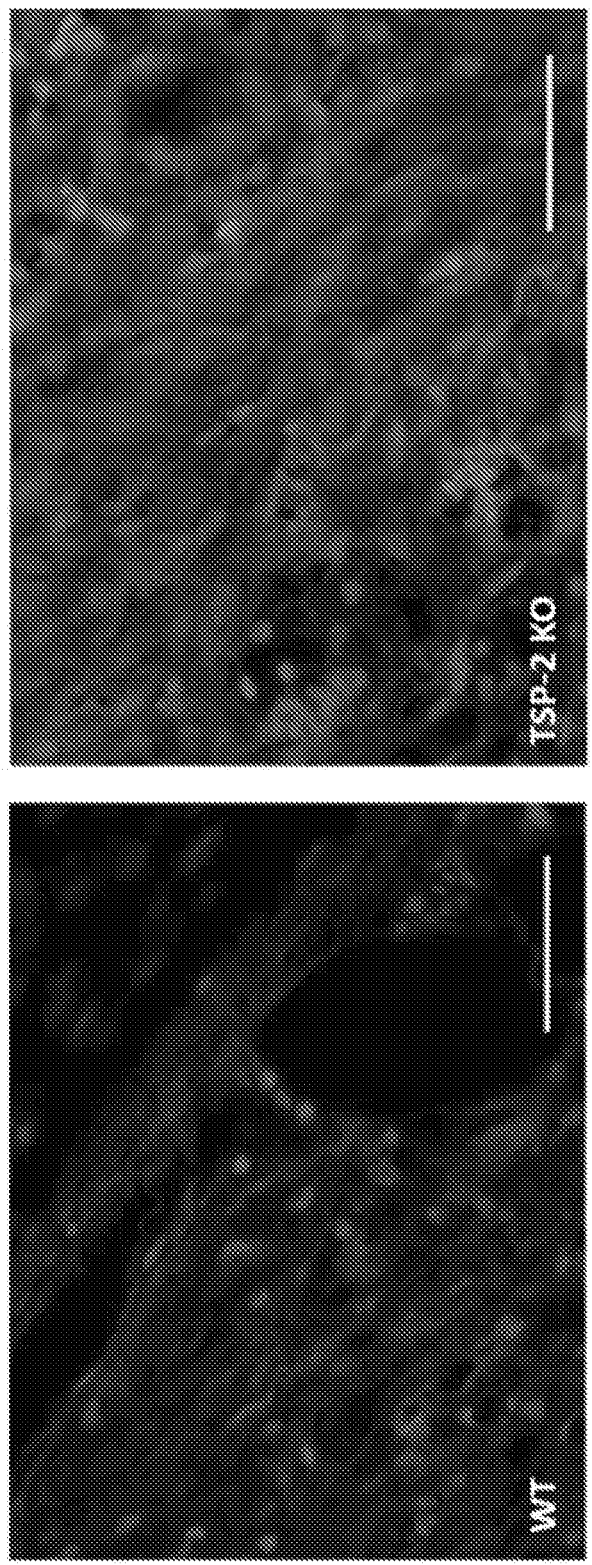
Figure 6B:
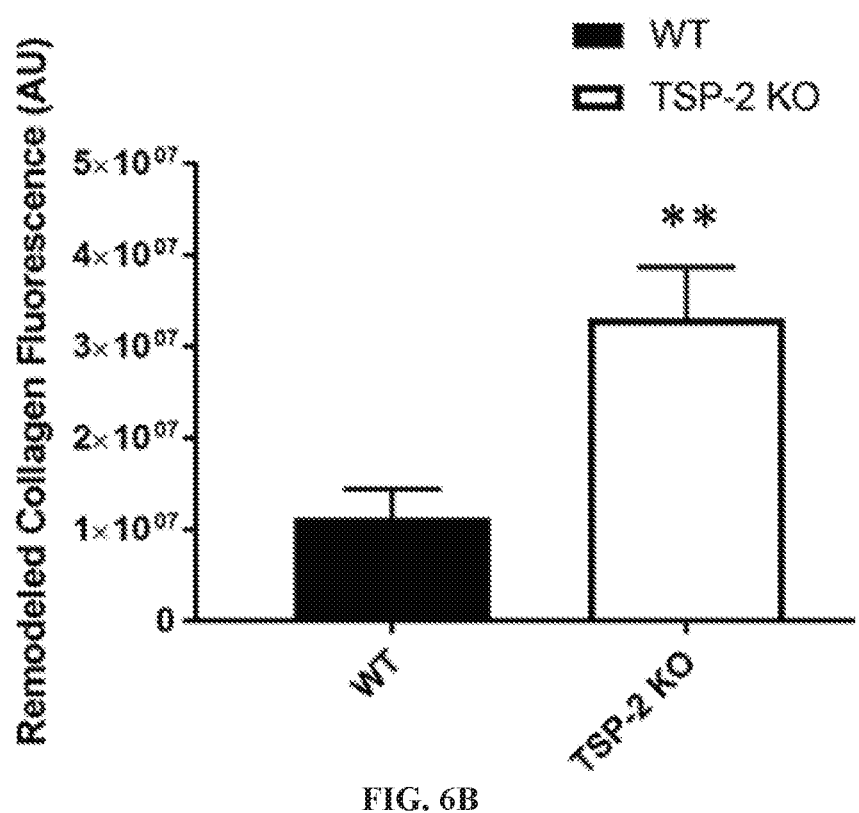
Figure 6C:
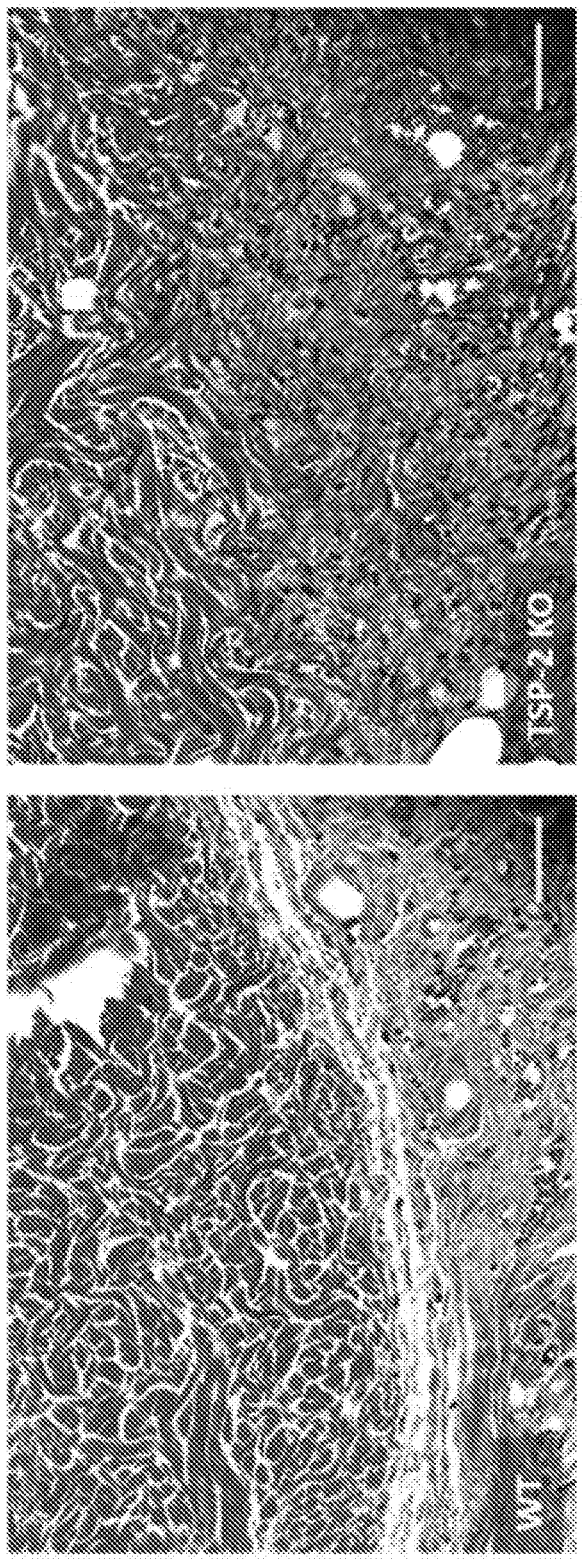
Figure 6D:
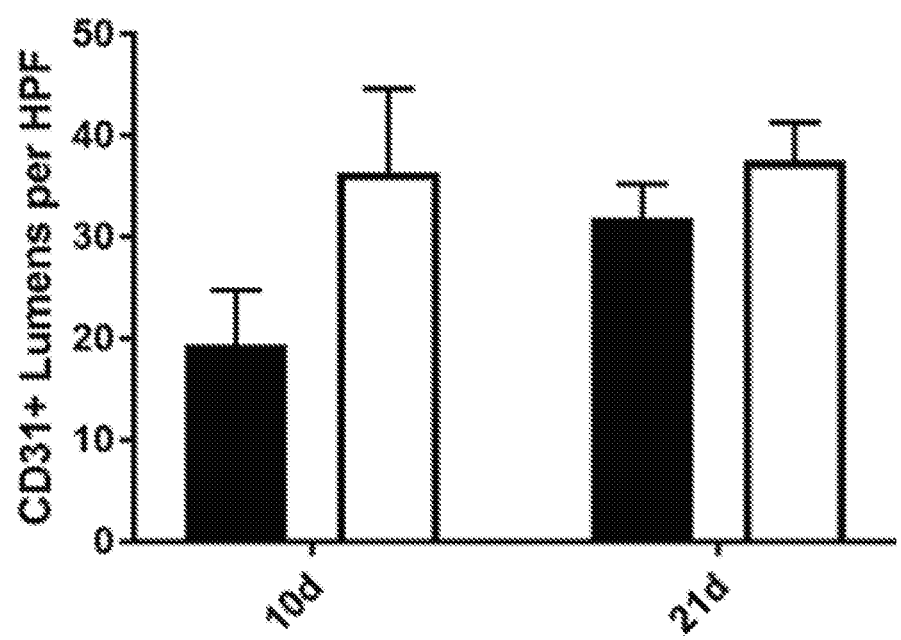
Figure 6E:
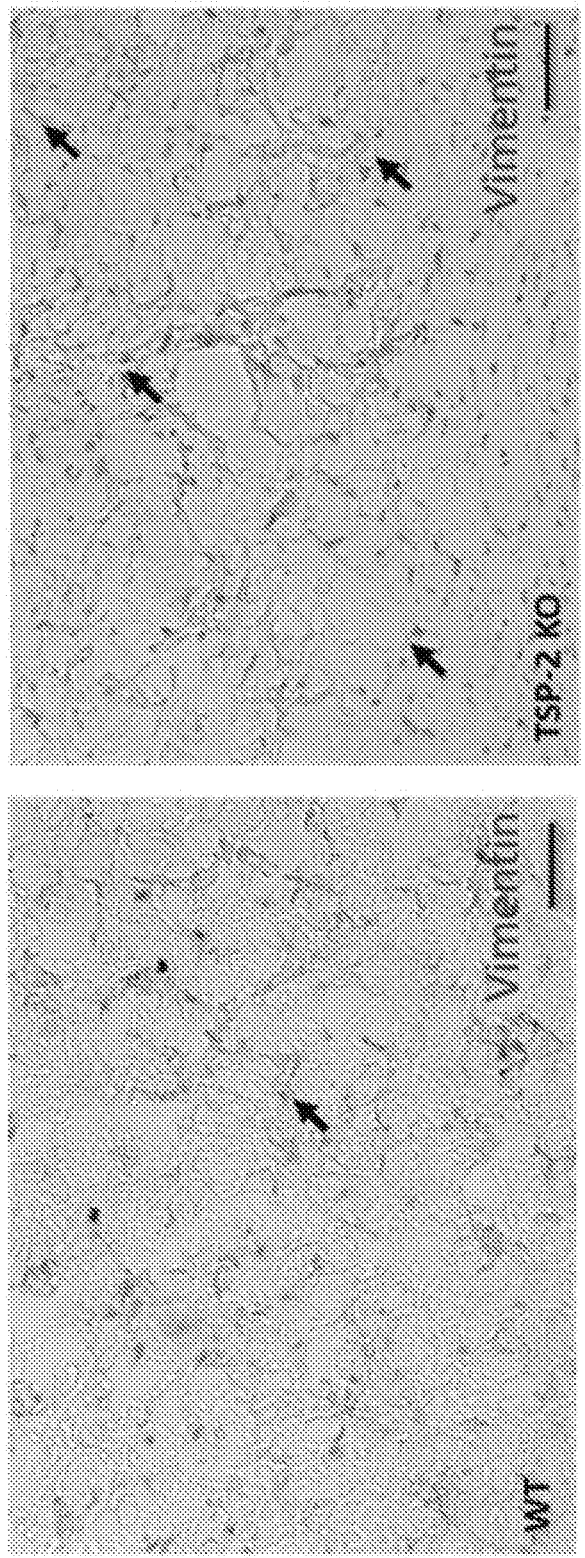
Figure 6F:
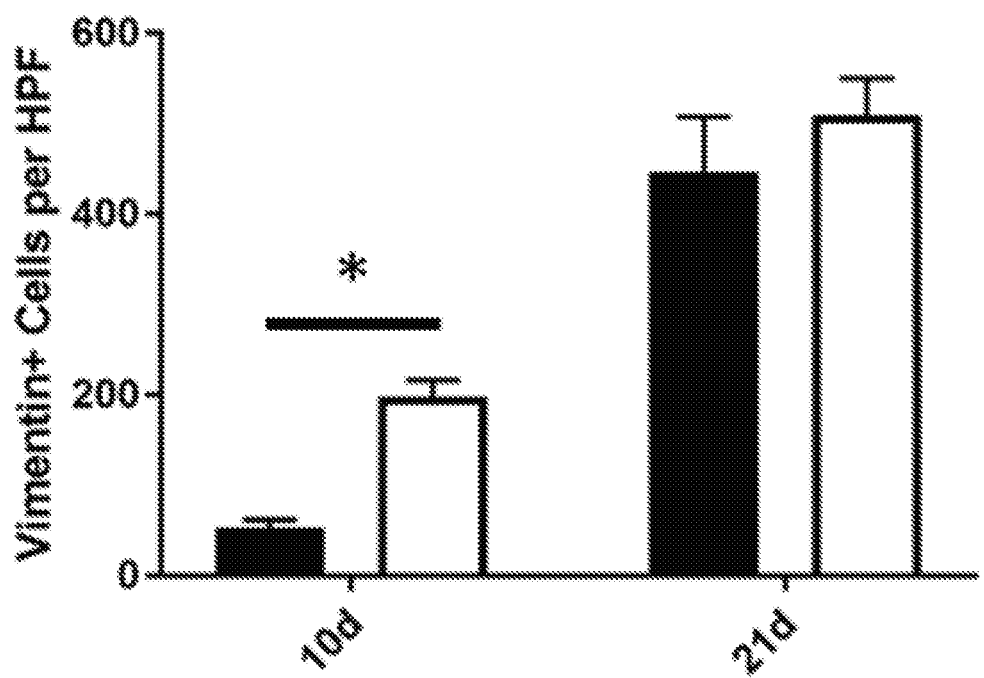
Figure 6G:
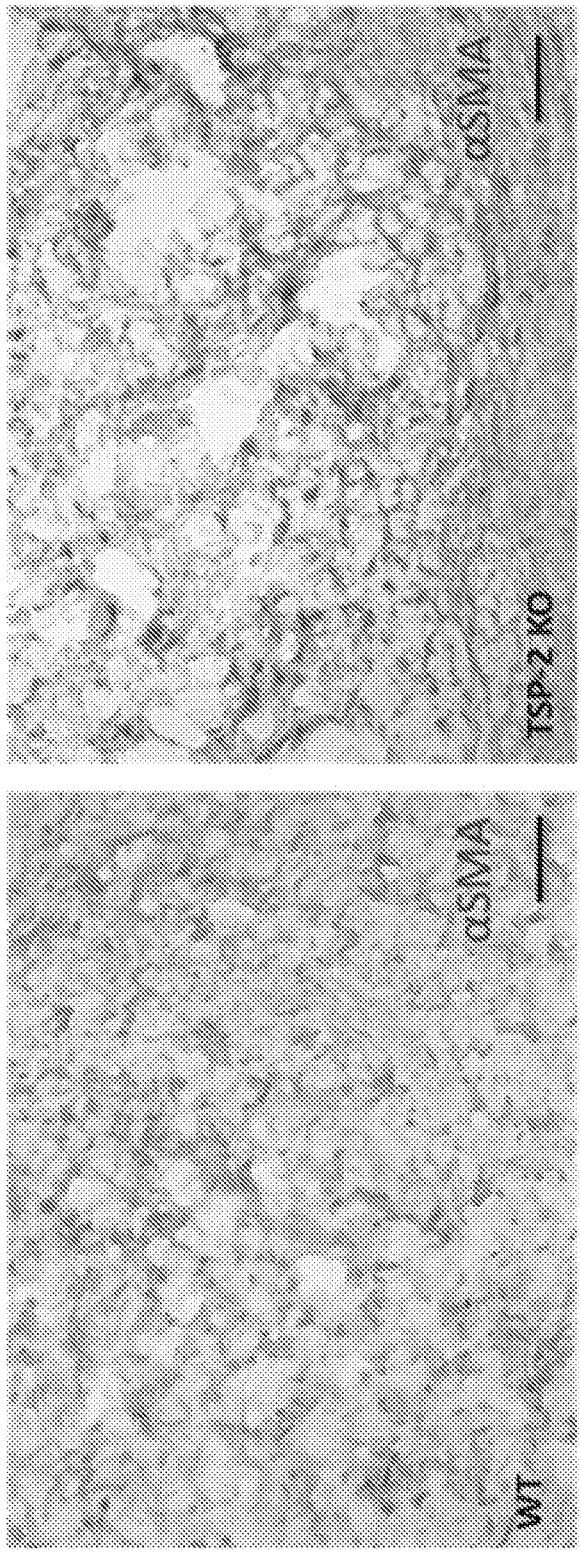
Figure 6H:
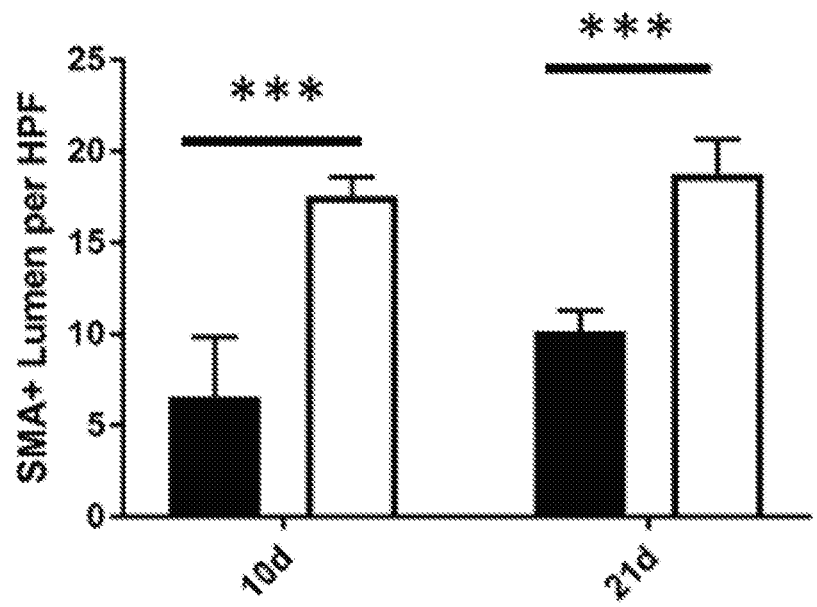

FIGS. 6A-6H are images and graphs showing that TSP-2 KO ADM exhibited enhanced integration and vascular maturation in diabetic wounds. FIGS. 6A-6B are representative images of collagen remodeling in ADM after 10 days of implantation in diabetic wounds (FIG. 6A) and a graph demonstrating increased remodeling in TSP-2 KO ADM (FIG. 6B). FIG. 6C is a set of representative images of Masson's trichrome staining along border of graft demonstrate increased tissue integration with TSP-2 KO ADM; the border between normal tissue and graft is no longer visible by 10 days. There were no differences in total vessel number (CD31) between WT and TSP-2 KO ADM treated wounds at 10 or 21 days (FIG. 6D). FIG. 6E is a set of representative images of vimentin staining after 10 days. FIG. 6F is a graph quantifying the vimentin stain indicating an increased penetration of mesenchymal cells within the TSP-2 KO ADM by 10 days. The WT ADM were no different by 21 days. FIG. 6G is a set of representative images of αSMA after 10 days, and FIG. 6H is a graph quantifying the staining in FIG. 6G, revealing more positive vessels at both 10 and 21 days. n=4 (10 days) or n=6 (21 days). Scale bars=50 μm. Results are given as mean+SEM, *p<0.05, **p<0.01.

Figure 7A:
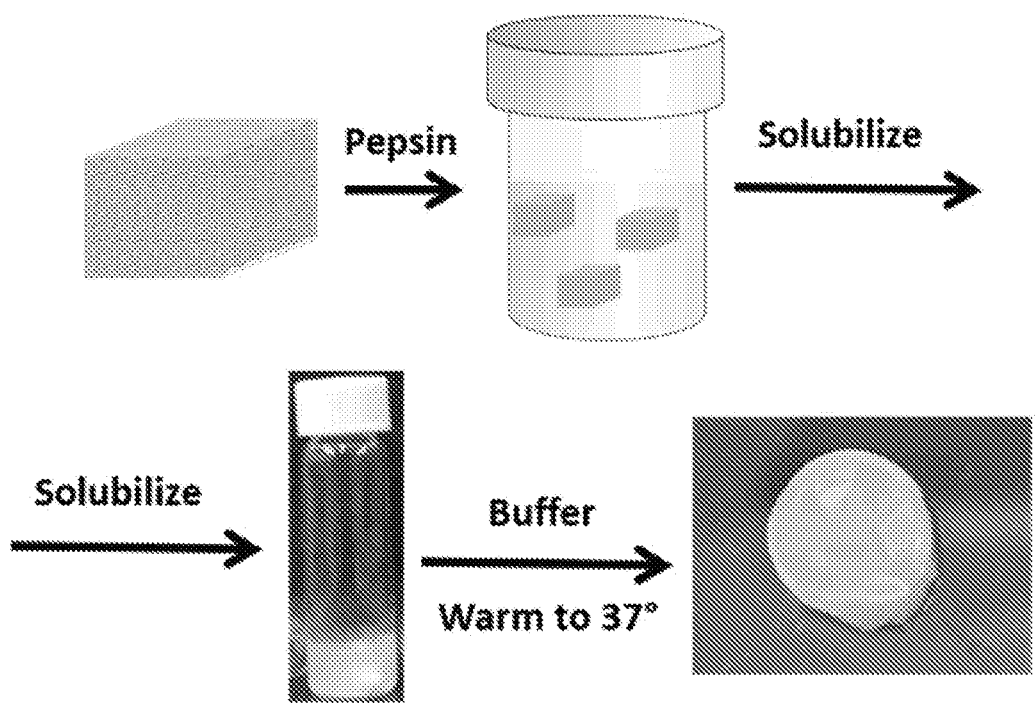
Figure 7B:
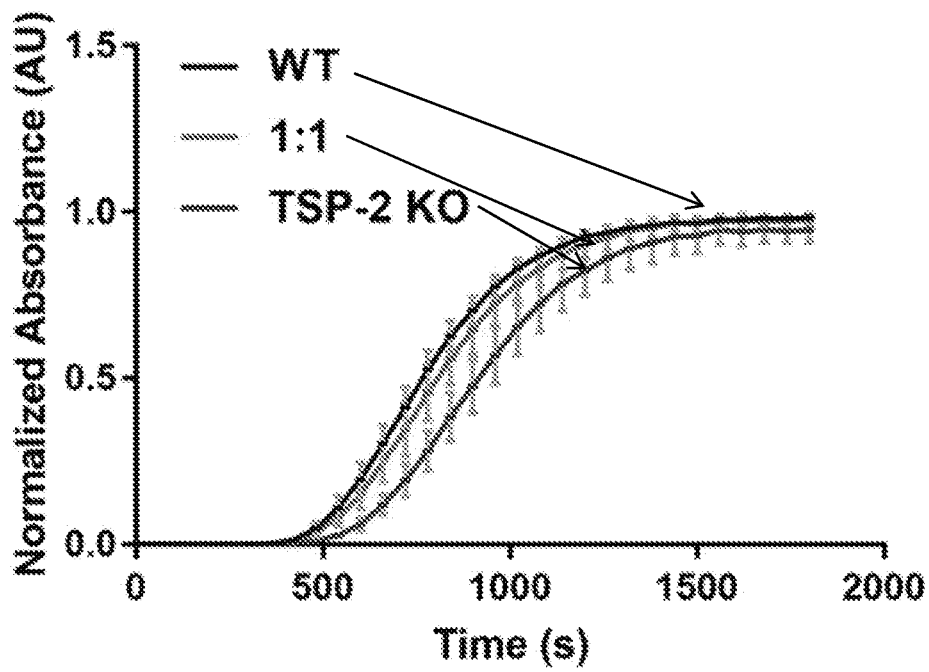
Figure 7C:
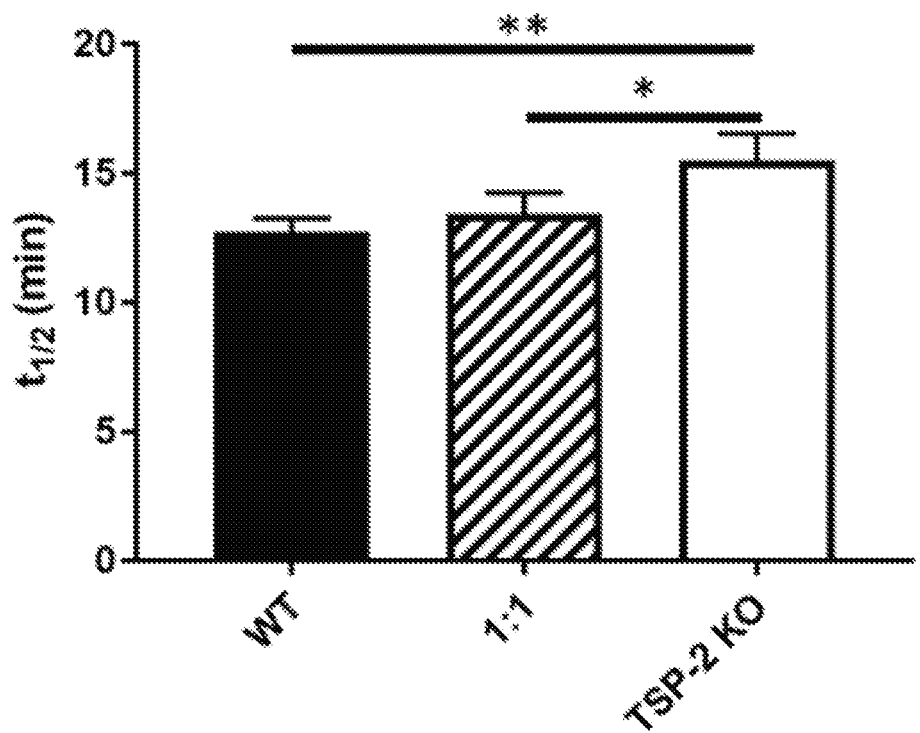
Figure 7D:
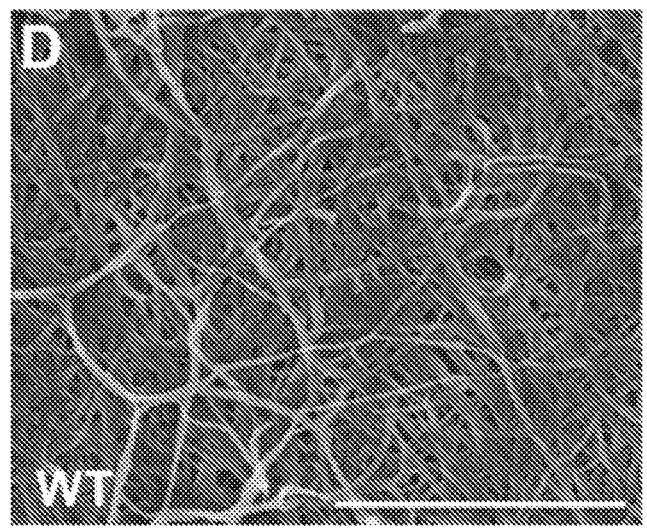
Figure 7E:
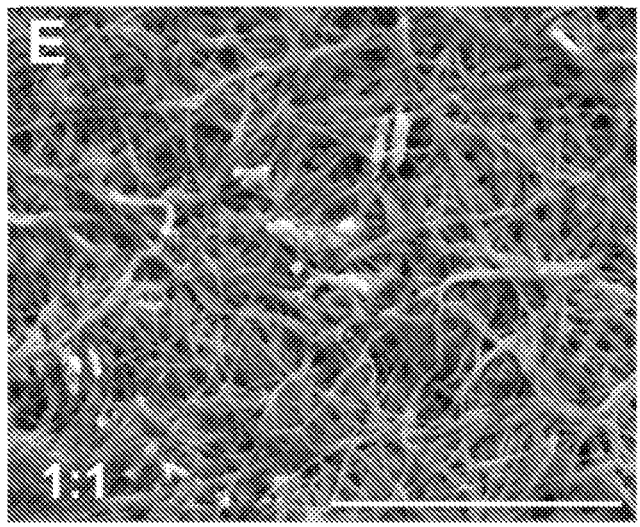
Figure 7F:
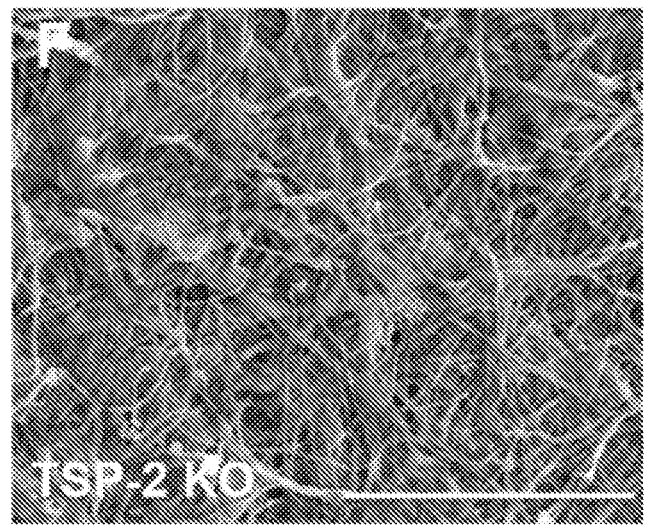
Figure 7G:
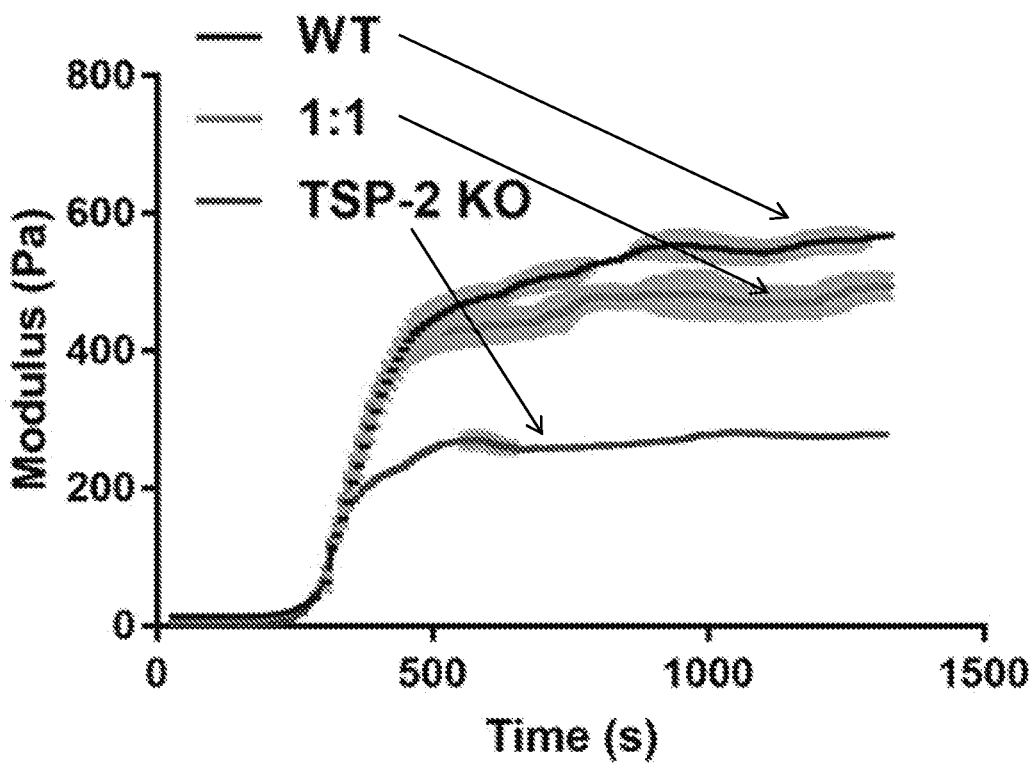
Figure 7H:
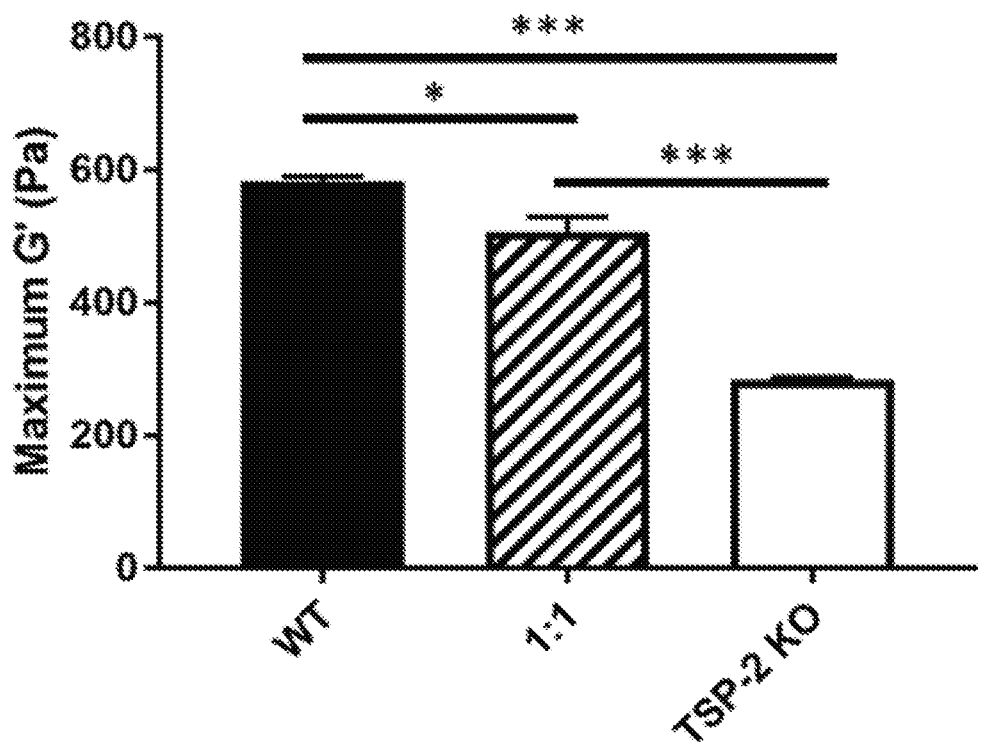

FIGS. 7A-7H are schemes, graphs and images showing that genetic manipulation permitted tunability of tissue-derived hydrogels. FIG. 7A is a schematic of hydrogel preparation and an example macroscopic image of hydrogel. FIGS. 7B-7C are graphs of optical density during gelation (FIG. 7B) and the time to half gelation of 4 mg/mL hydrogels (n=5) (FIG. 7C). FIGS. 7D-7F are representative SEMs of WT, 1:1, and TSP-2 KO gels showing similar structures, scale bars=5 μm. Rheology revealed overall changes in maxima, and suggested tunability of mechanical properties between WT, TSP-2 KO, and a 1:1 mixture (rheological traces are given as mean±SEM) (FIG. 7G). Analysis of rheological data indicated significant changes between maximum storage moduli with genotype of matrix (n=3) (FIG. 7H). Results are given as mean+SEM, *p<0.05, p<0.01, *p<0.005.

Figure 7I:
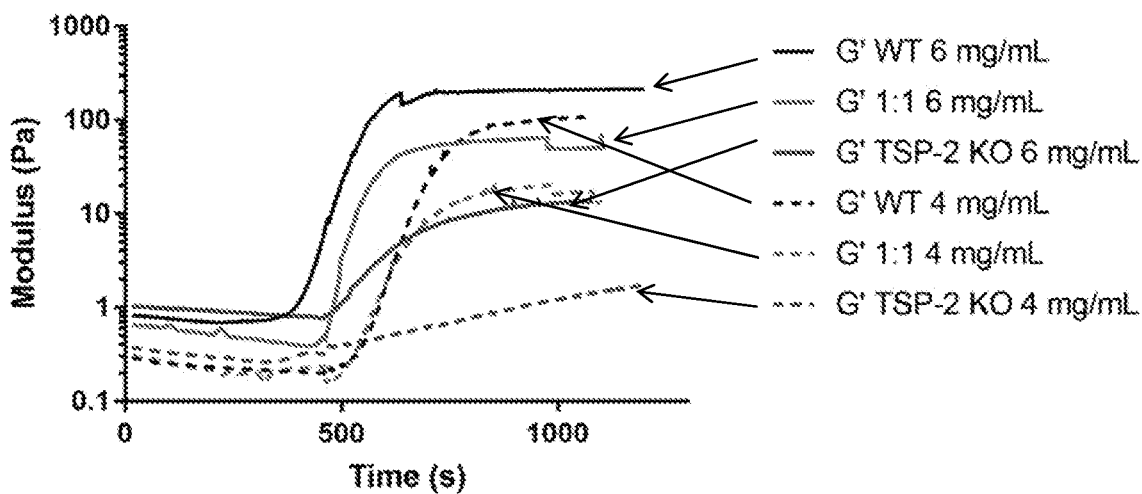
Figure 7J:
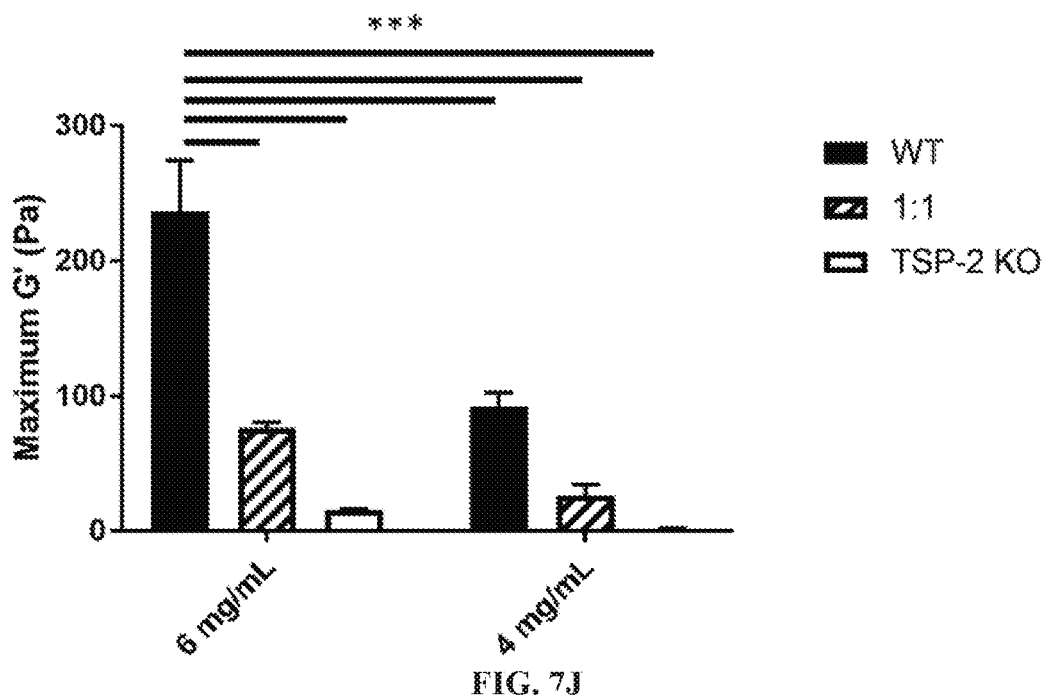

FIGS. 7I-7J are rheology graphs showing overall changes in maxima for WT. KO and 1:1 mixtures at both 4 mg/mL and 6 mg/mL. Data are presented as means. Analysis of rheological data indicates significant changes between maximum storage moduli with genotype of matrix (6 mg/mL, n=2-4; 4 mg/mL, n=3). Results are given as mean+SEM, ***p<0.005.

Figure 7K:
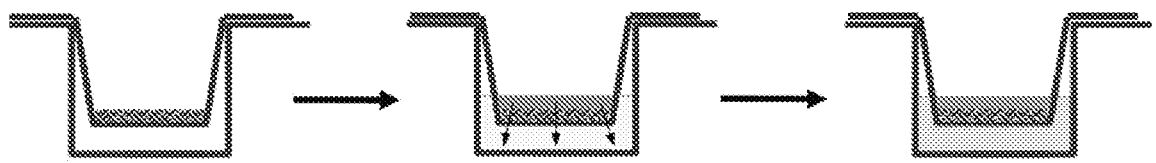
Figure 7L:
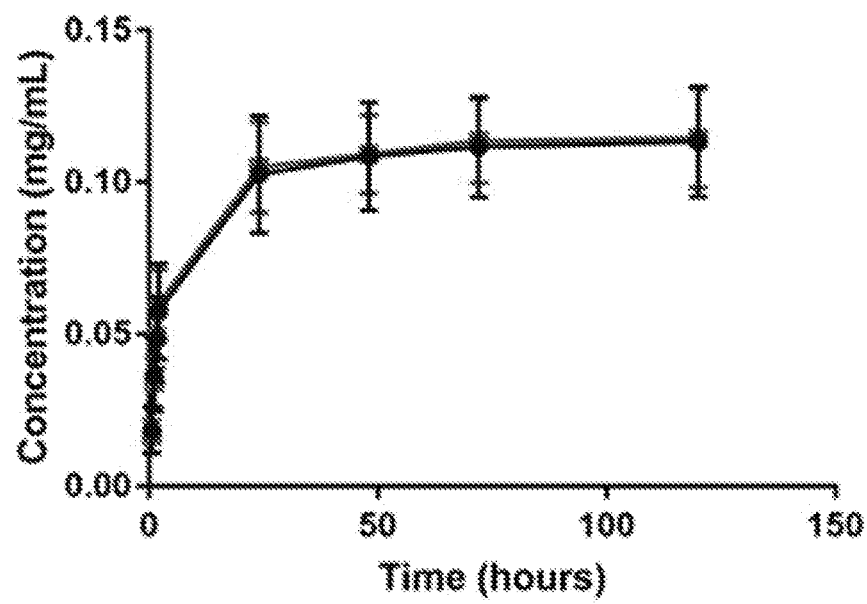
Figure 7M:
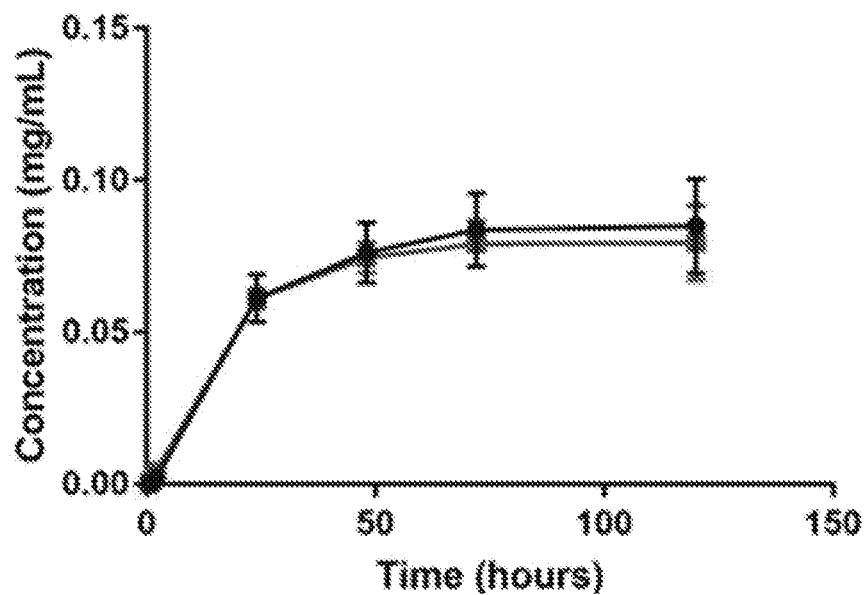
Figure 7N:
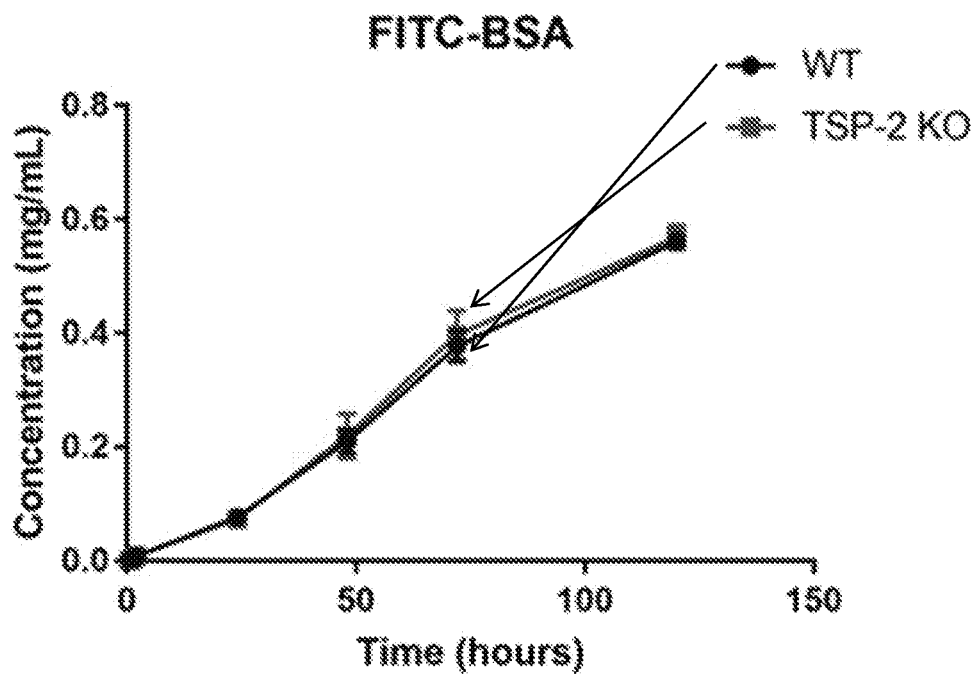

FIGS. 7K-7N are a scheme and graphs showing that the diffusion of small molecules, proteins, and large polysaccharides was unchanged between WT and TSP-2 KO hydrogels. FIG. 7K is a schematic of the diffusion experiments through the hydrogels. Fluorescein, FITC-Dextran, and FITC-BSA diffused through TSP-2 KO hydrogels at the same rate that they do through WT (FIGS. 7L-7N).

Figure 8A:
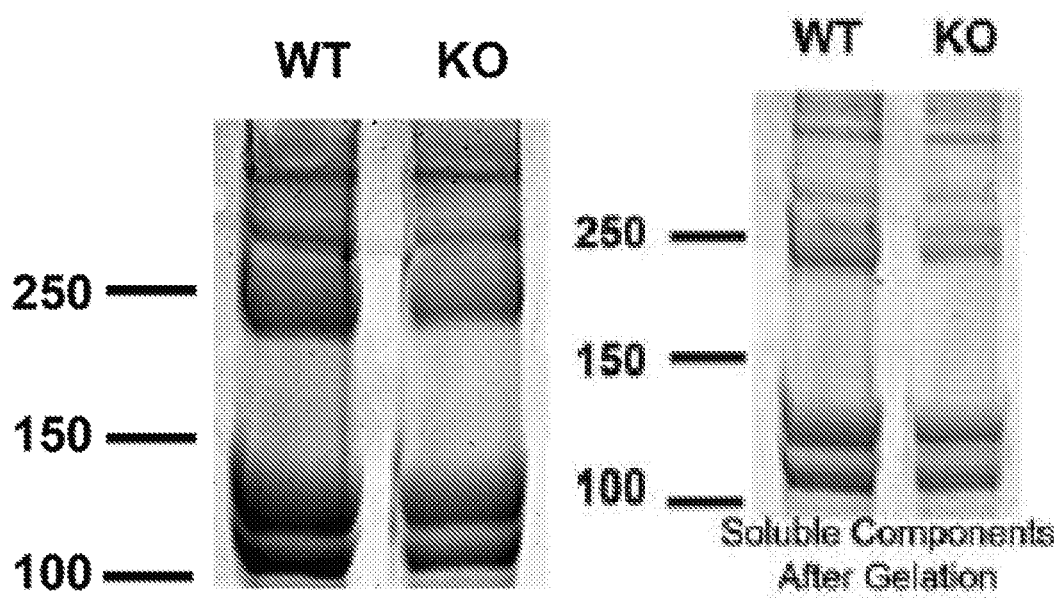
Figure 8B:
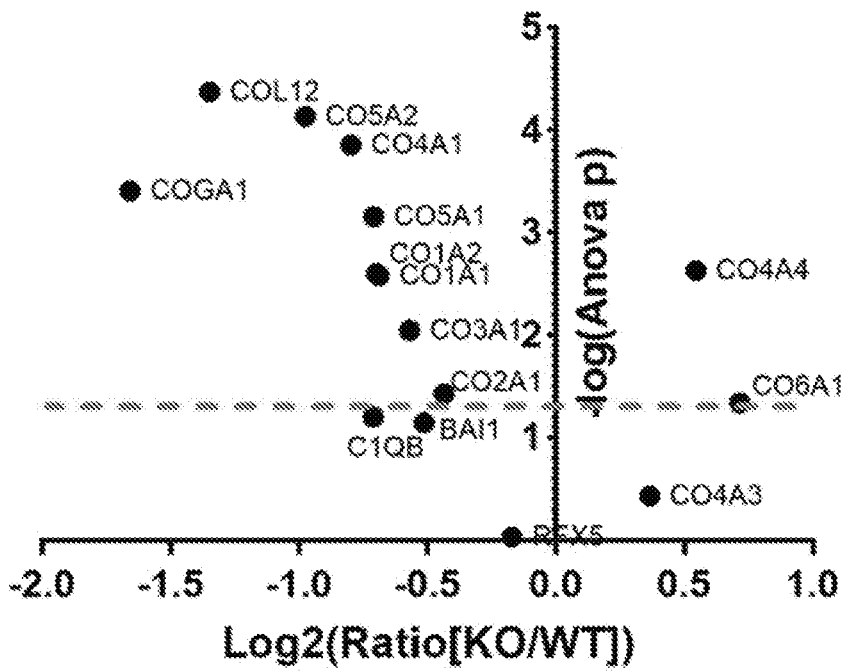
Figure 8C:
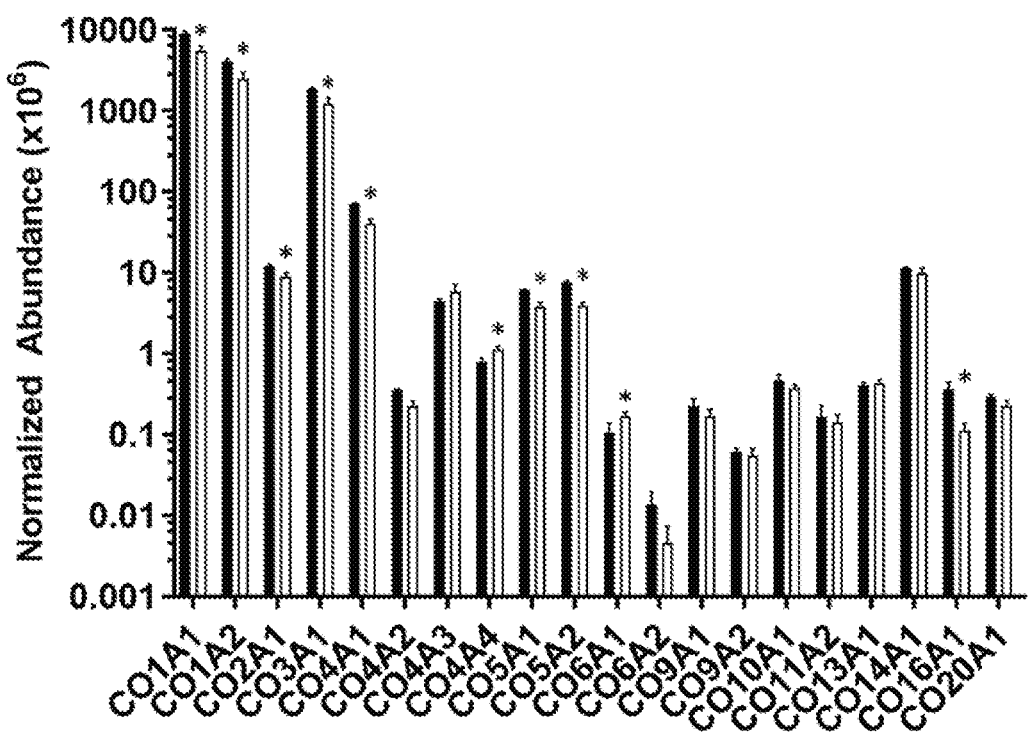
Figure 8D:
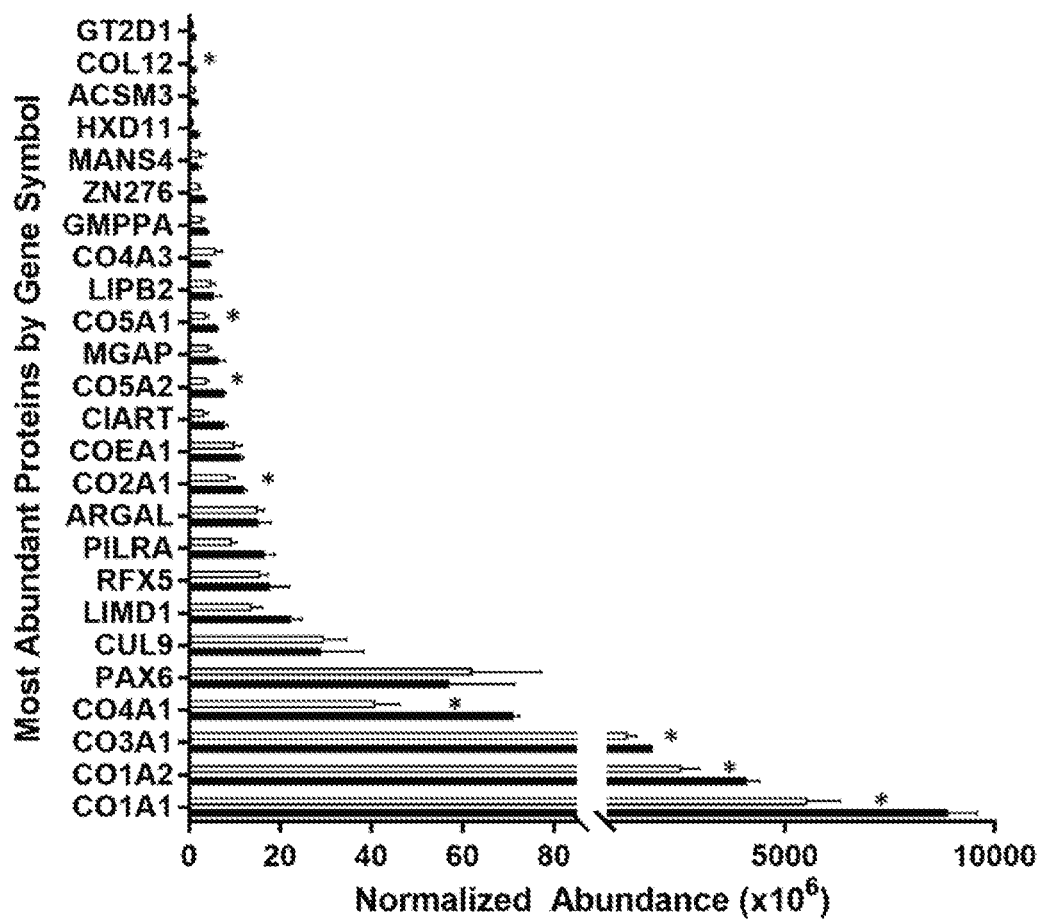

FIGS. 8A-8D are images and graphs showing subtle changes in the composition of hydrogels between genotypes. FIG. 8A is set of SDS-PAGE images demonstrating qualitative differences in the protein content of WT and TSP-2 KO gels. FIG. 8B is a volcano plot of quantitative proteomics results demonstrates significant differences between WT and TSP-2 KO (above red dashed line is p<0.05). FIG. 8C is a graph showing that collagen abundance from quantitative proteomics exhibited similar, albeit altered levels between genotypes. FIG. 8D is a graph showing that the top 25 most abundant proteins show differences between WT and TSP-2 KO gels. Results are given as mean+SEM, n=3, *p<0.05.

Figure 9A:
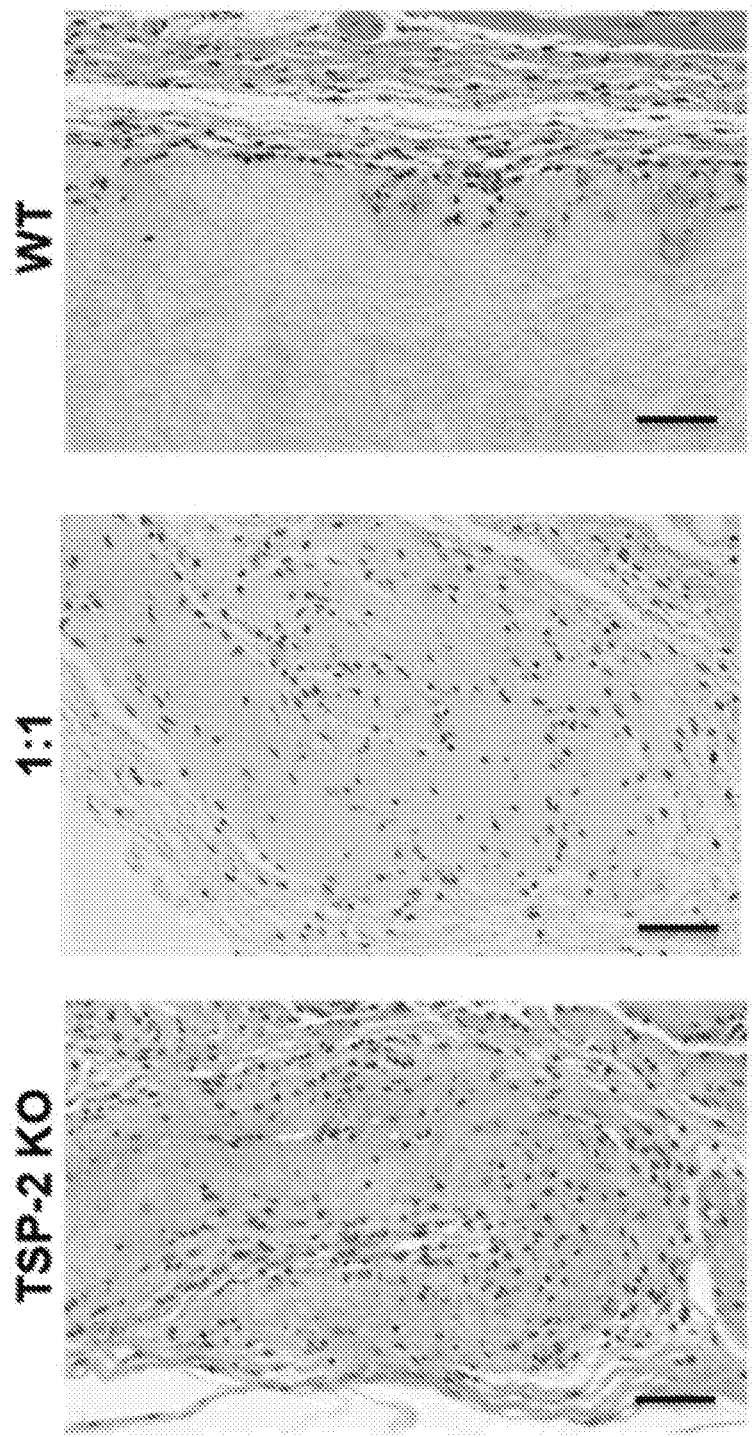
Figure 9B:
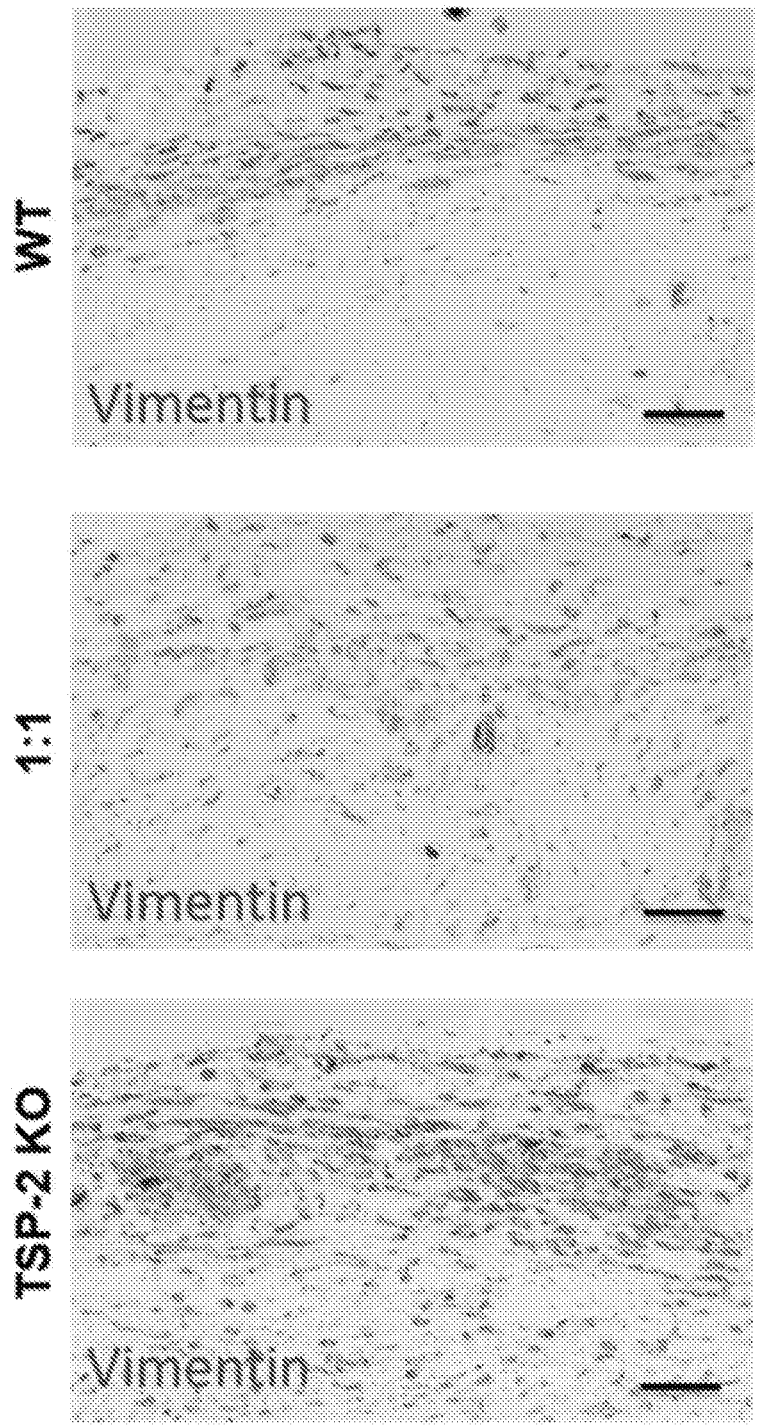
Figure 9C:
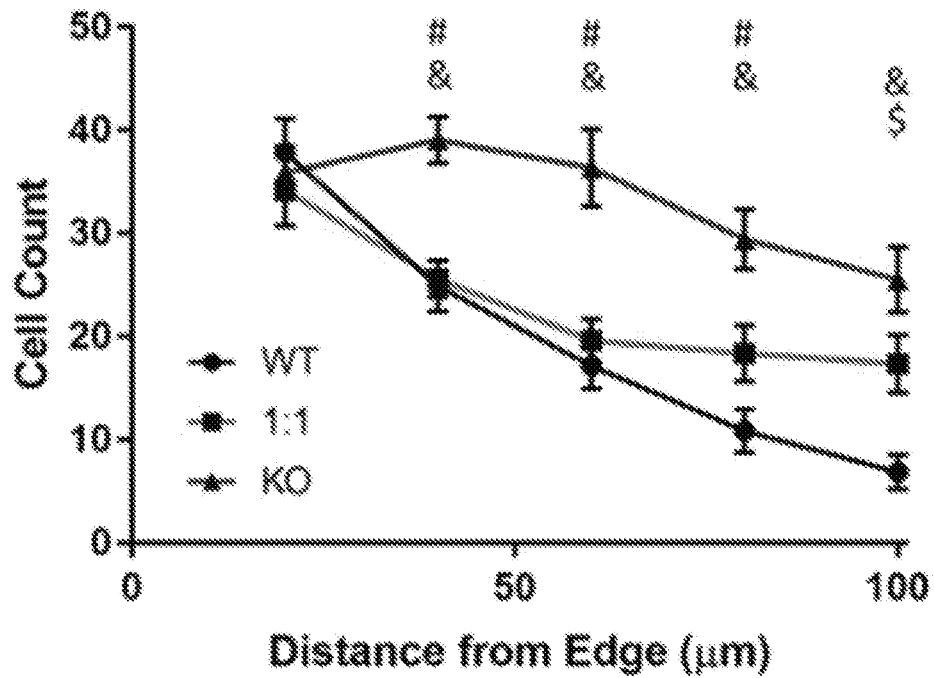
Figure 9D:
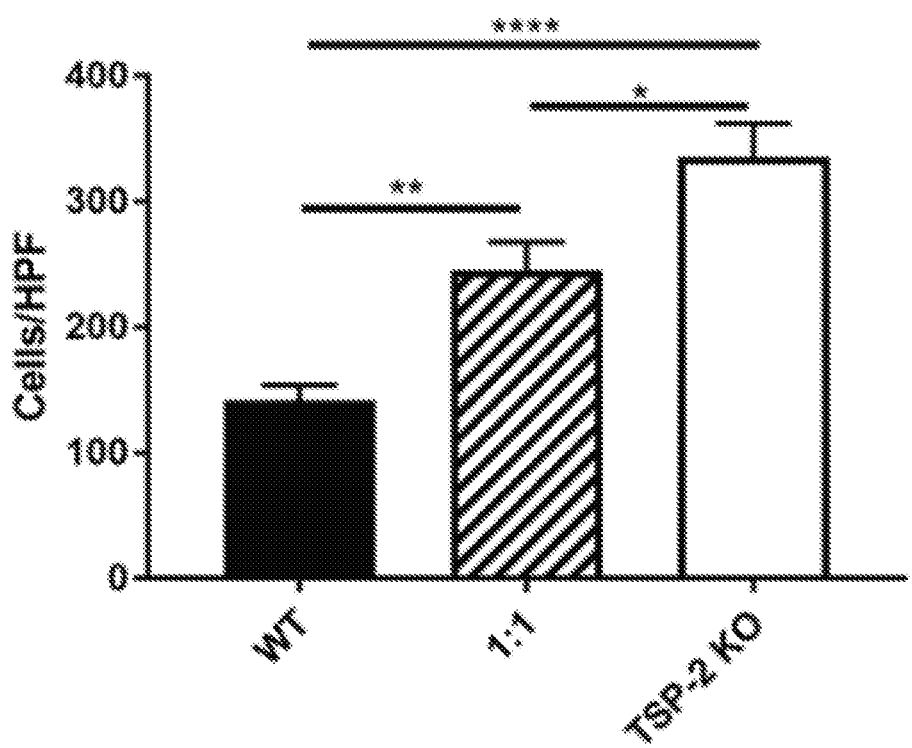

FIGS. 9A-9D are images and graphs showing that genetic manipulation permitted tunability of cell invasion into tissue-derived hydrogels. FIG. 9A is a set of representative H&E images indicating higher cell presence in TSP-2 KO gels that were implanted subcutaneously in healthy mice for 5 days. FIG. 9B is a set of vimentin staining images indicating that many of the cells present were of a mesenchymal lineage. FIG. 9C is a graph quantifying how far cells penetrated into WT, TSP-2 KO and 1:1 WT/TSP-2 KO hydrogels (FIG. 9C). FIG. 9D is a graph showing that an increasing ratio of TSP-2 KO matrix in the hydrogel resulted in increased total cellular content. Scale bars=50 μm. Results are given as mean+SEM (±SEM for panel C), n=8, *p<0.05, p<0.01, **p<0.001. # indicates that TSP-2 KO is different from WT, $ indicates that 1:1 is different from WT, and & indicates that 1:1 is different from TSP-2 KO, p<0.05.

Figure 9E:
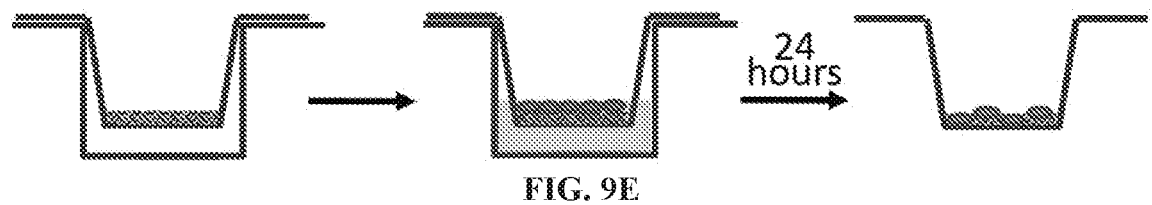
Figure 9F:
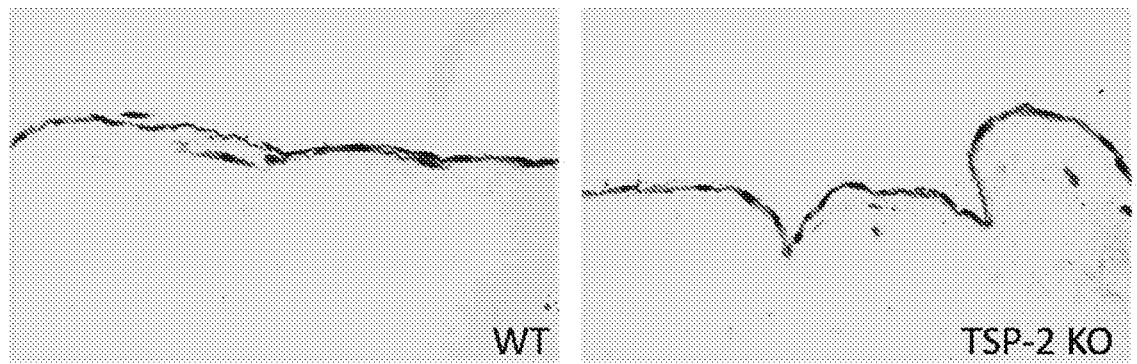
Figure 9G:
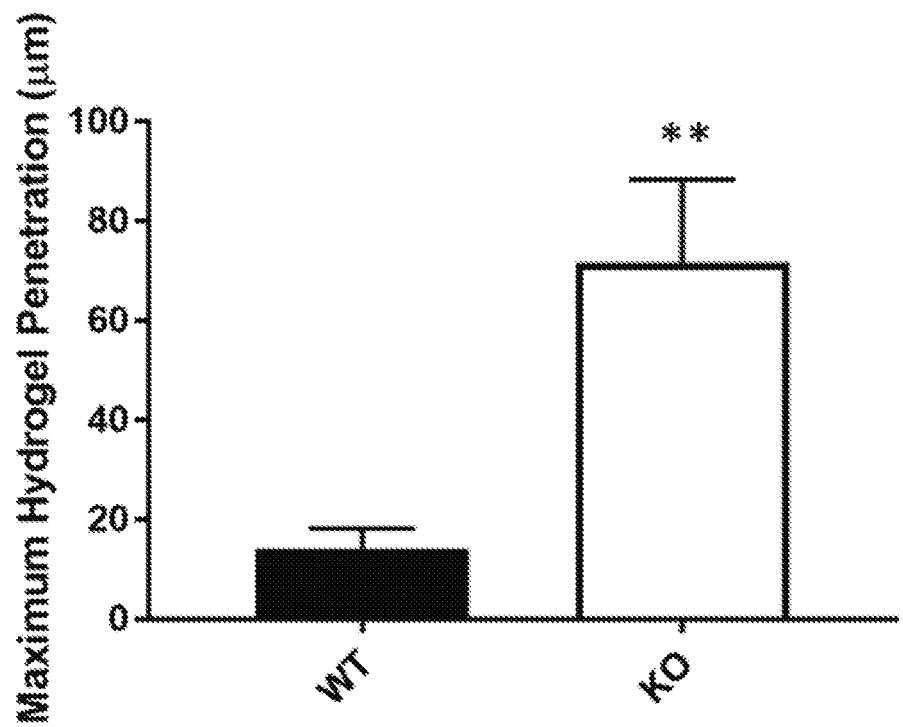

FIGS. 9E-9G are graphs showing that TSP-2 KO hydrogel was more permissive to fibroblast migration in vitro. FIG. 9E is a schematic of the in vitro migration assay for cell migration into hydrogel. FIG. 9F is an image showing that a uniform layer of cells is visible on top of the gels after 24 hours. Cells migrated into the TSP-2 KO gel faster than the WT (FIG. 9G). Results are given as mean+SEM, n=5, **p<0.01.

Figure 10A:
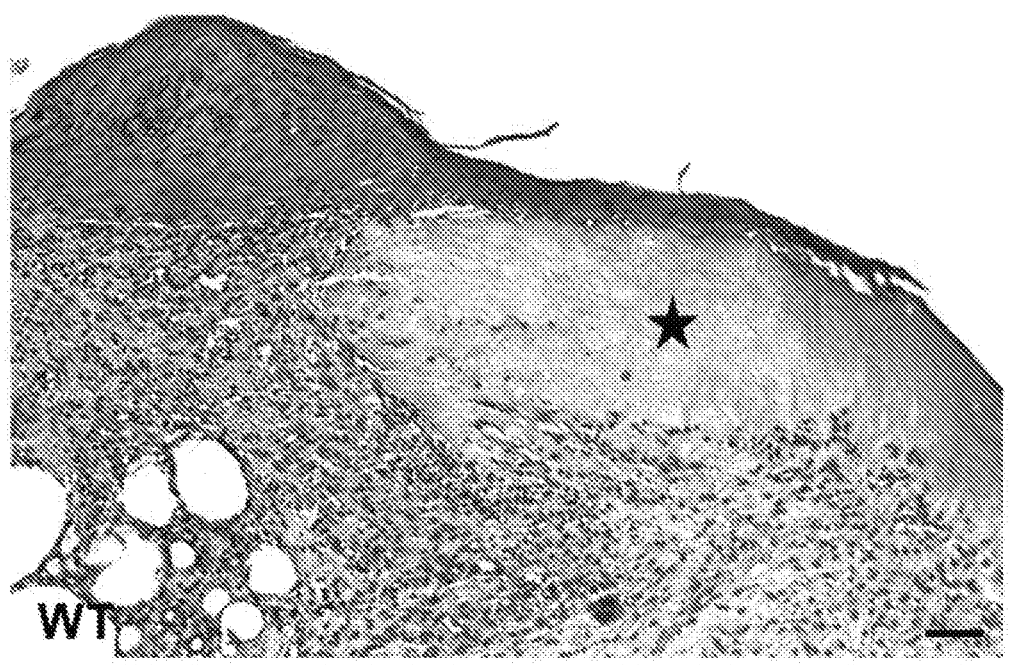
Figure 10B:
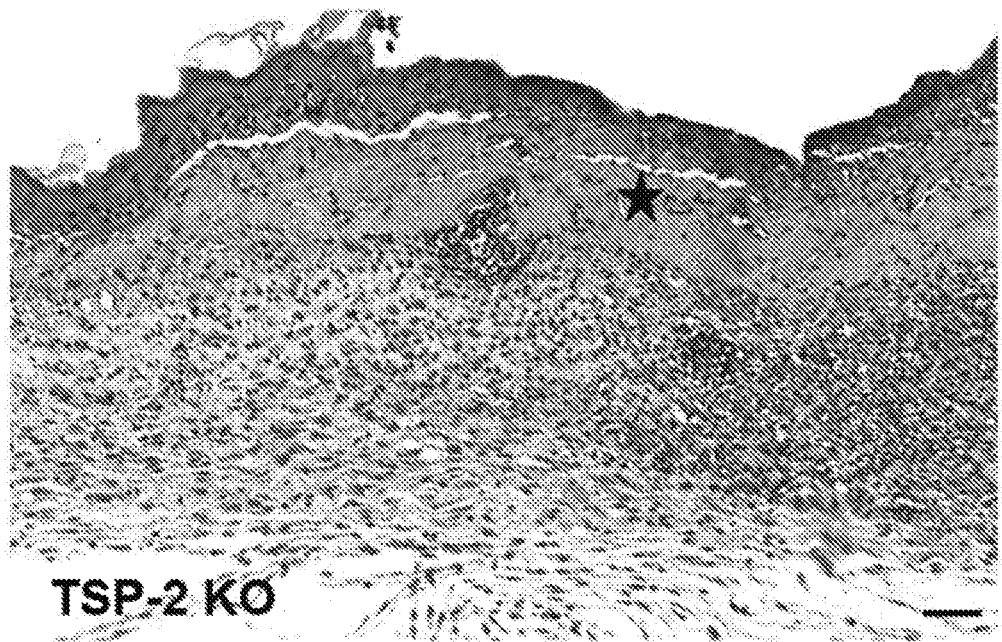
Figure 10C:
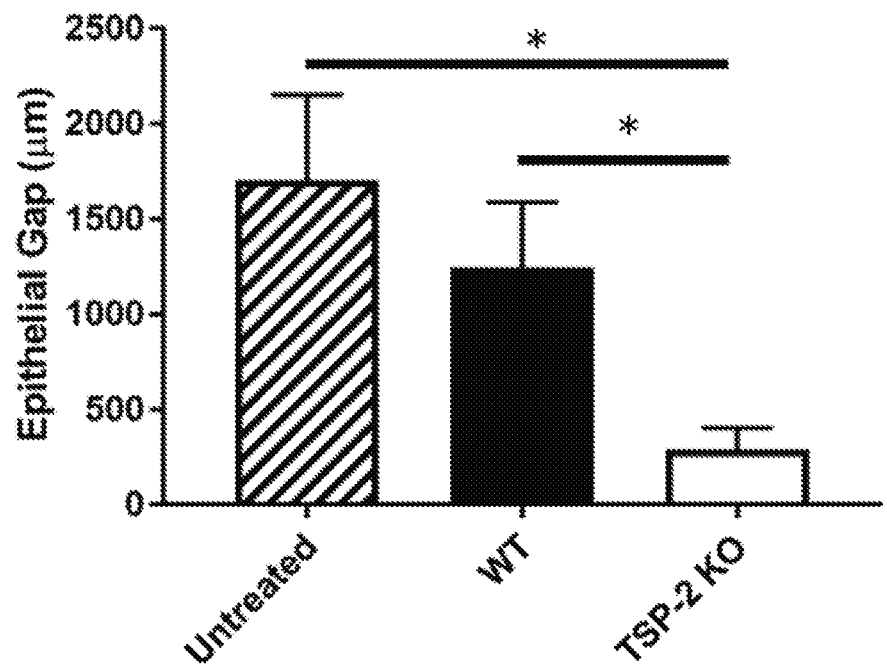
Figure 10D:
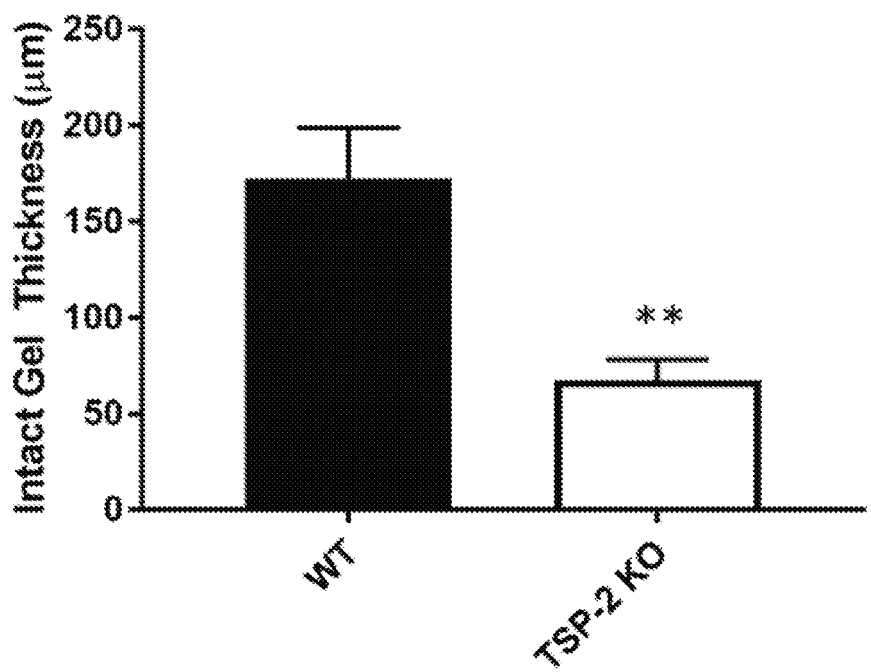
Figure 10E:
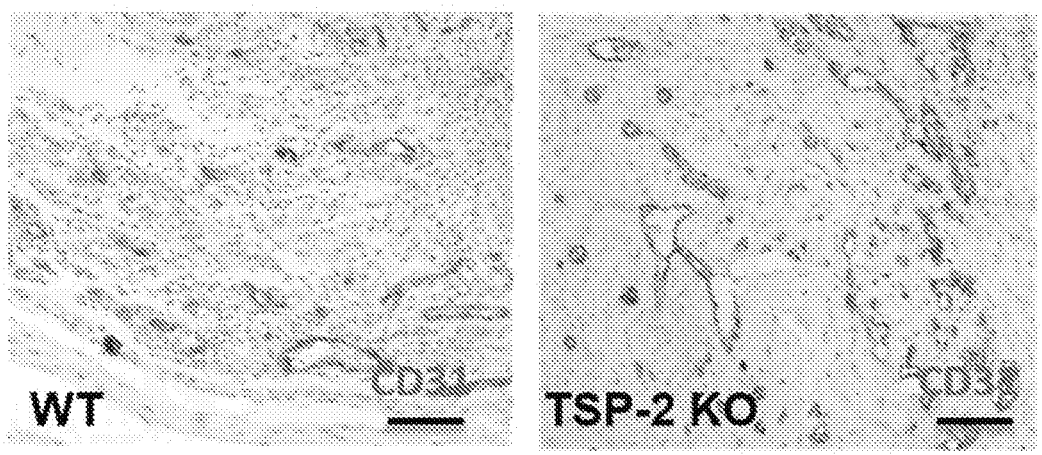
Figure 10F:
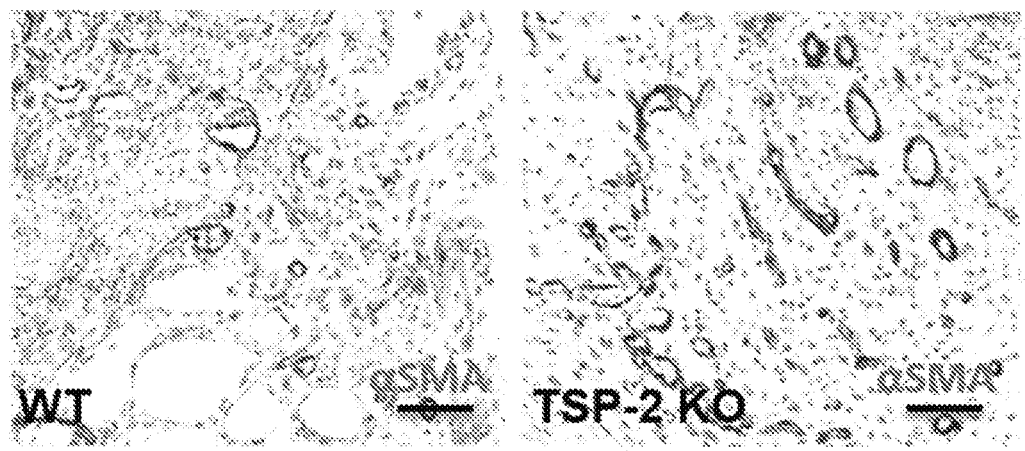
Figure 10G:
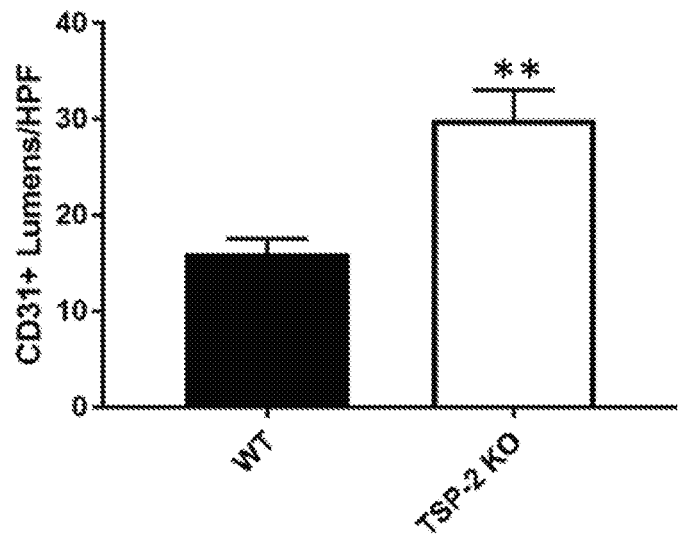
Figure 10H:
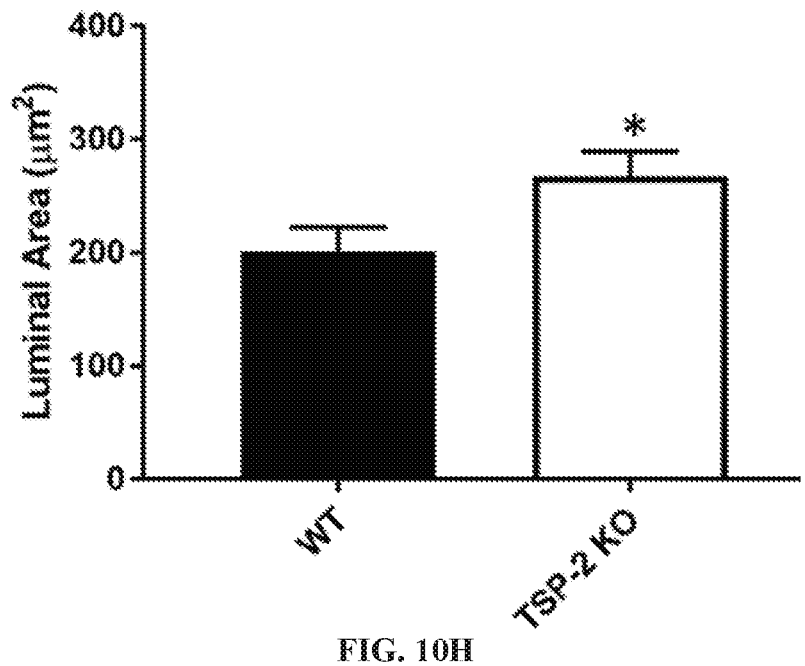
Figure 10I:
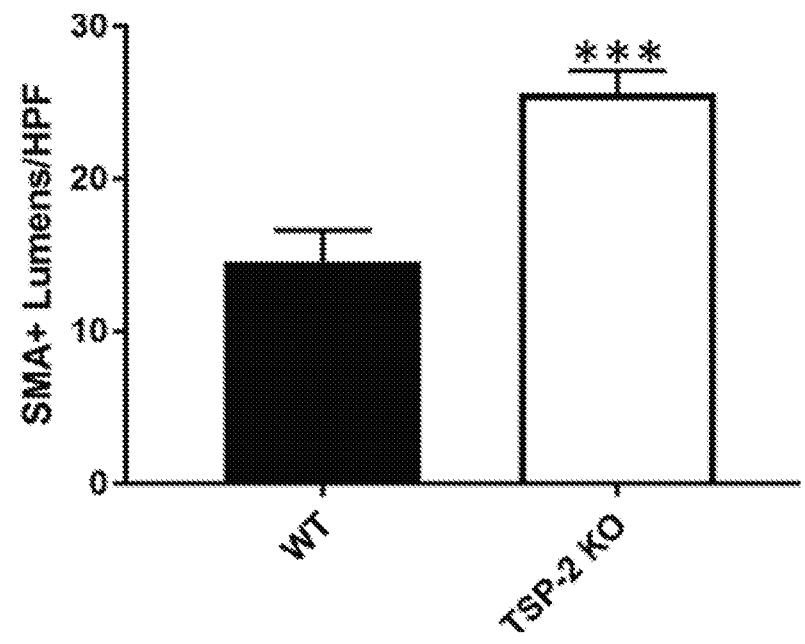

FIGS. 10A-10I are images and graphs showing improved diabetic wound closure and vascularization with TSP-2 KO hydrogel in mice. FIGS. 10A-10B are a set of representative images of H&E staining indicating higher cell presence within TSP-2 KO gels (FIG. 10B) than WT gels (FIG. 10A) that were implanted into full thickness diabetic wounds for 10 days. FIG. 10C is a graph showing that TSP-2 KO gel demonstrated a decreased epithelial gap at 10 days. FIG. 10D is a graph showing that the thickness of the remaining gel was reduced with TSP-2 KO gel, suggesting increased remodeling. FIGS. 10E-10F are representative images of CD31 stains (FIG. 10E) and αSMA stains (FIG. 10F). FIGS. 10G-10I are graphs showing quantification of CD31 and αSMA stains showing increased vessel density (FIG. 10G), size (FIG. 10H), and maturity (FIG. 10I) in wound beds treated with TSP-2 KO gel. Scale bars=50 μm. Results are given as mean+SEM, n=4 (untreated), n=9 (gel treated), *p<0.05, **p<0.01.

Figure 11A:
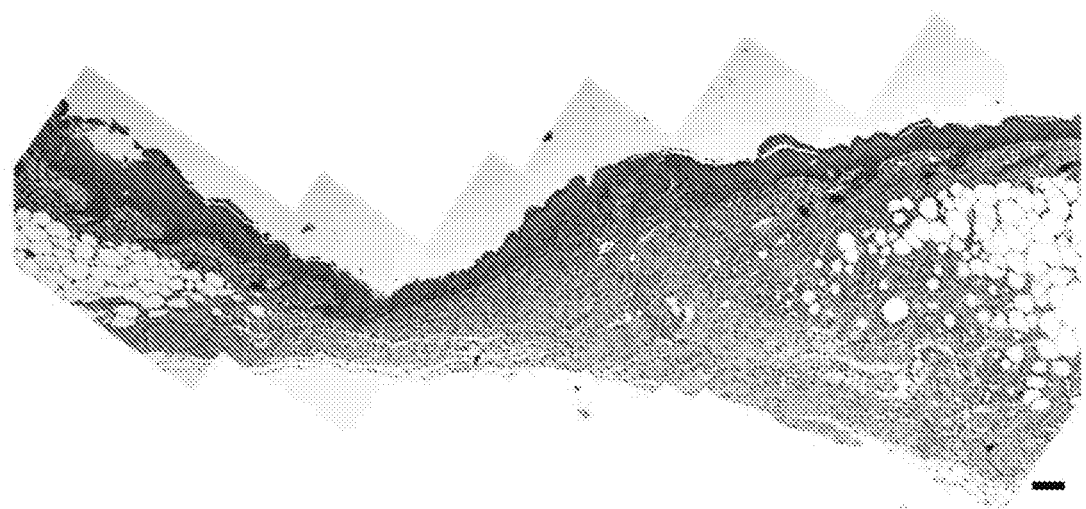
Figure 11B:
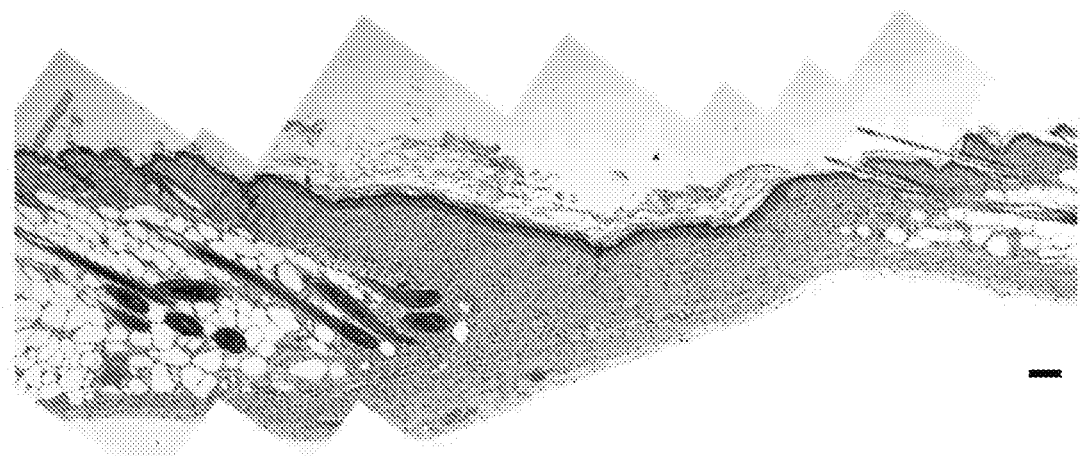
Figure 11C:
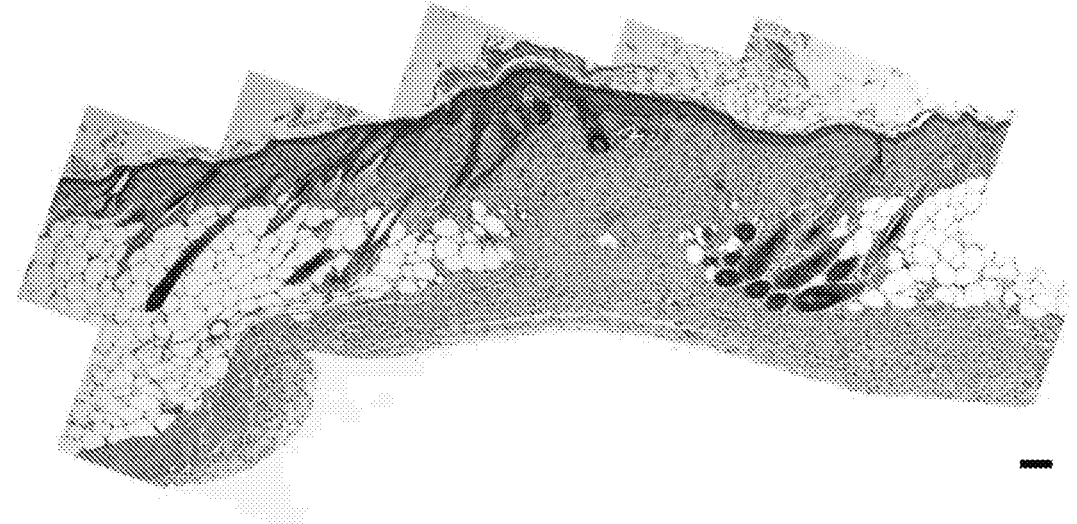
Figure 11D:
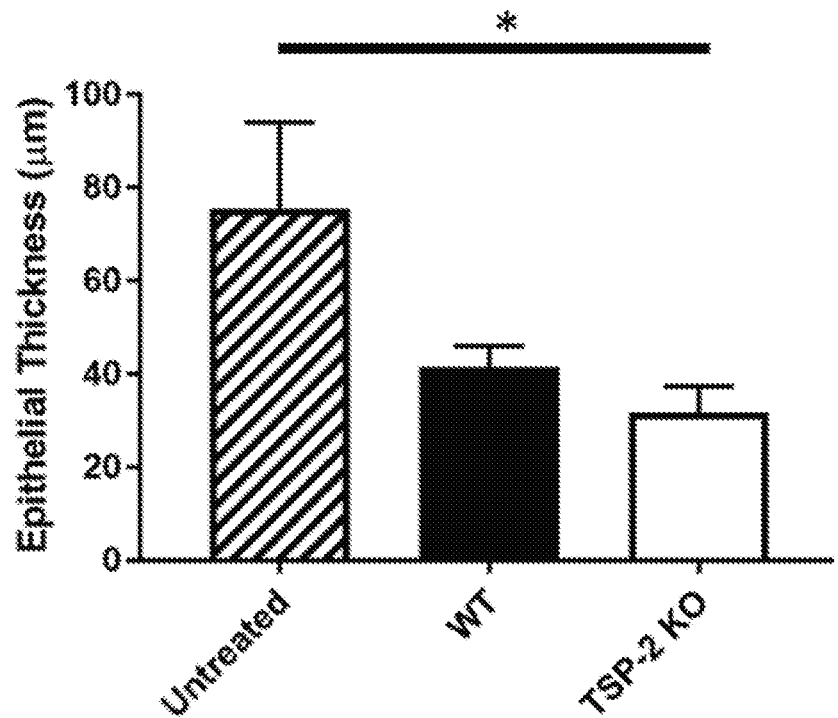
Figure 11E:
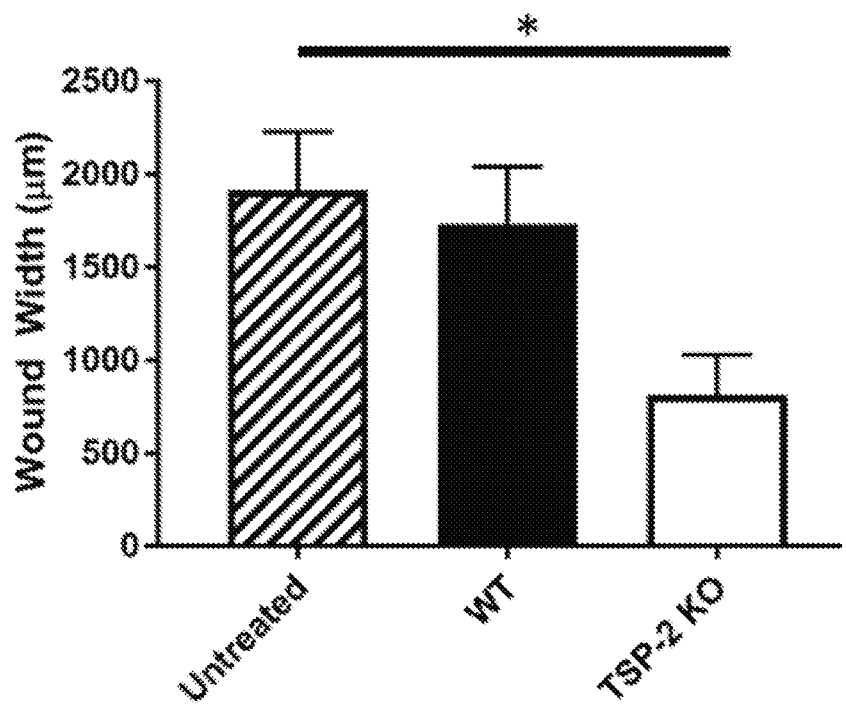

FIG. 11A-11E are images and graphs showing that TSP-2 KO hydrogels improved diabetic wound resolution compared to untreated wounds in mice. FIGS. 11A-11C are a set of representative stitched images of entire wound beds from diabetic mice after 21 days of healing that were untreated (FIG. 11A), WT gel treated (FIG. 11B), or TSP-2 KO gel-treated (FIG. 11C). FIG. 11D is a graph showing that TSP-2 KO-treated wounds demonstrated decreased epithelial thickness (a measure of maturity) by 21 days when compared to untreated control. FIG. 11E is a graph showing that TSP-2 KO gel demonstrated decreased wound width at 21 days. Scale bars=100 sm. Results are given as mean+ SEM, n=5 (untreated and WT gel treated), n=6 (KO gel treated), *p<0.05.

Figure 12A:
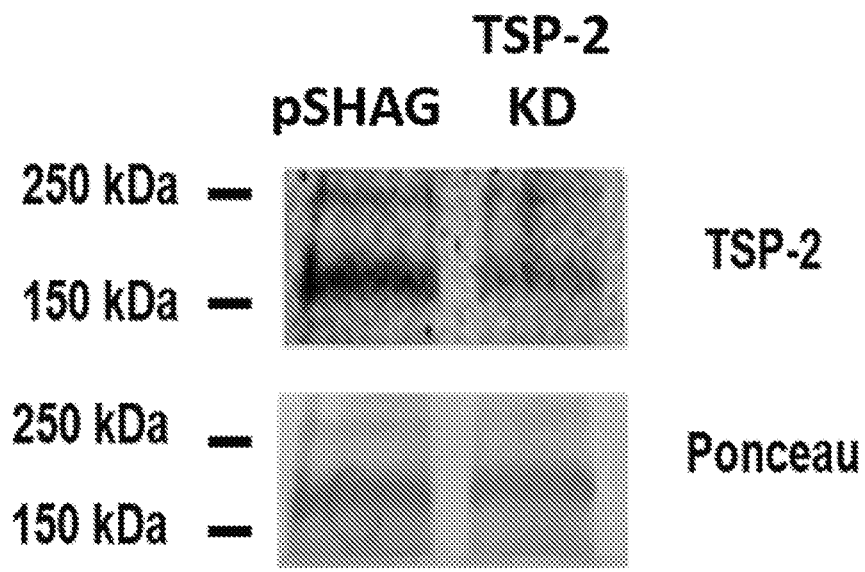
Figure 12B:
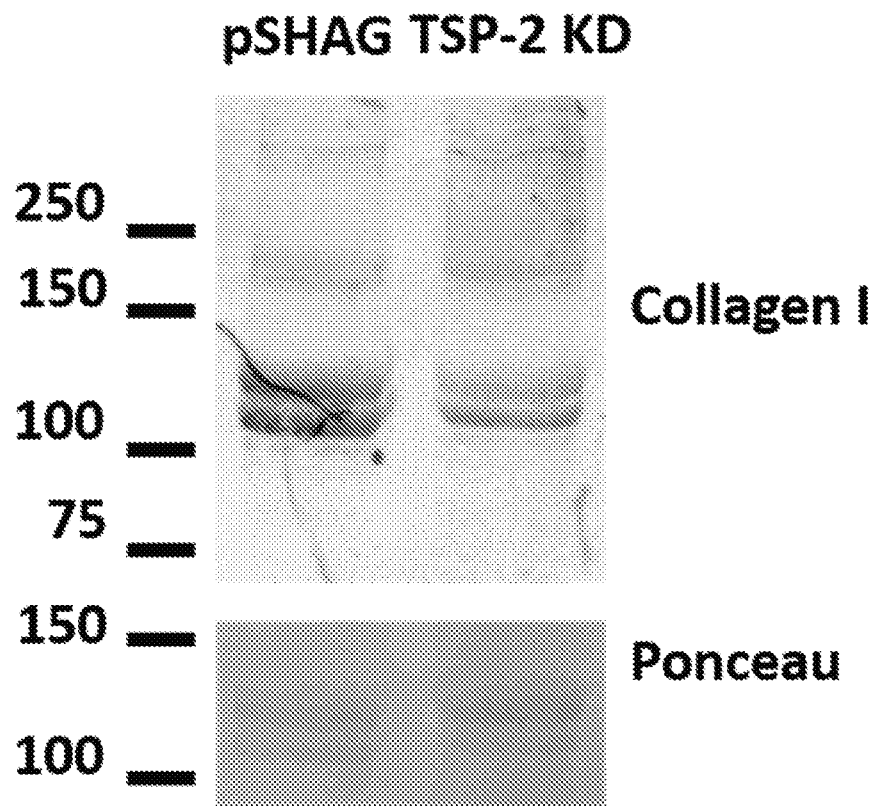
Figure 12C:
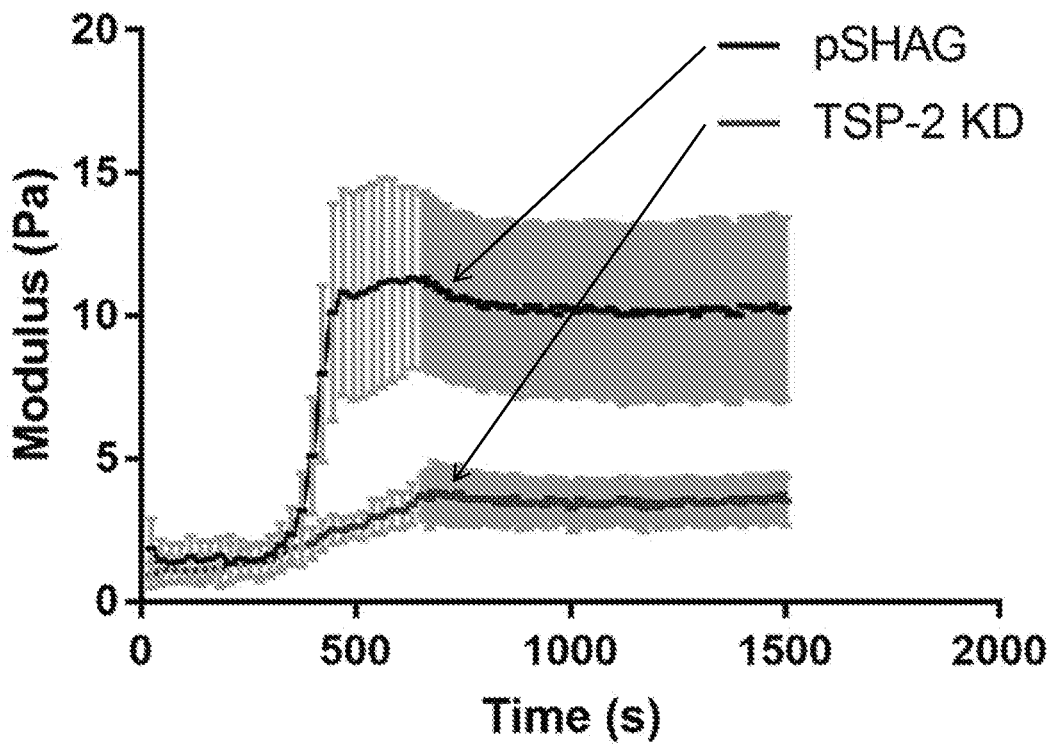
Figure 12D:
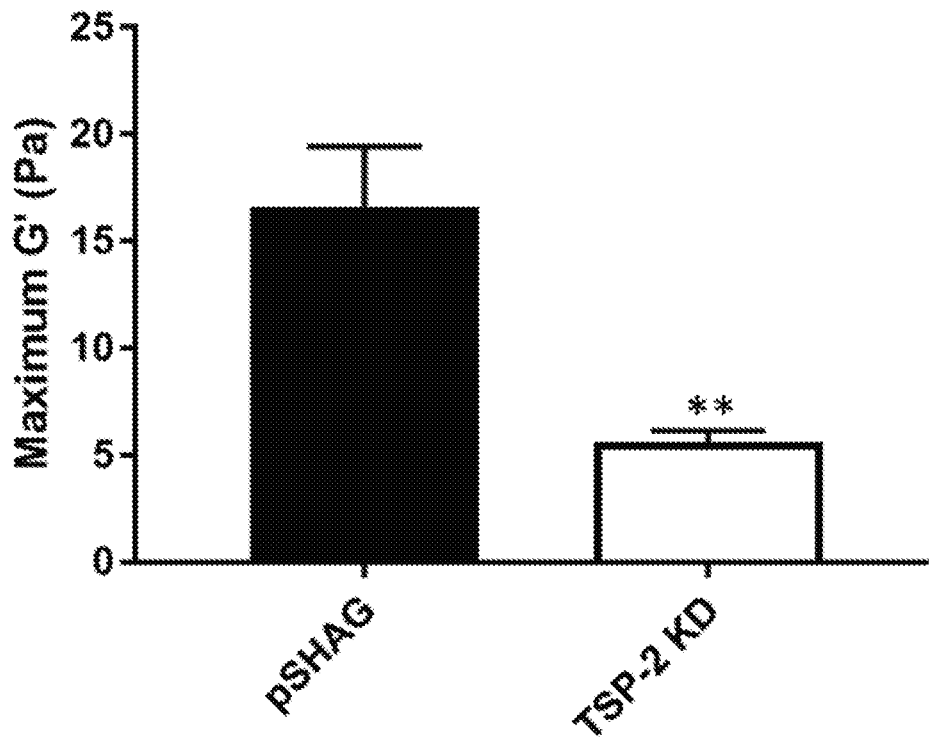
Figure 12E:
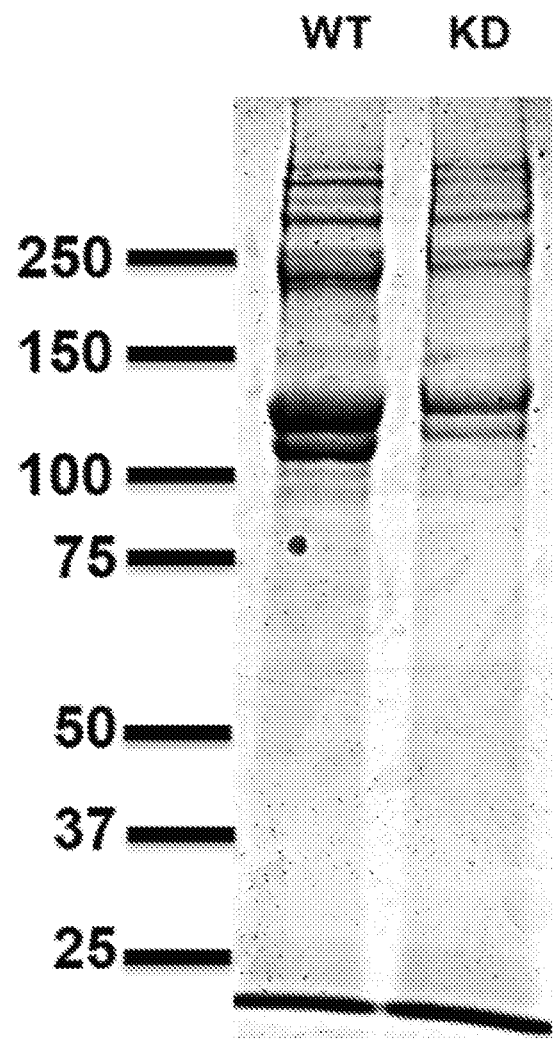

FIGS. 12A-12E are a set of images and graphs showing that hydrogels prepared from cell-derived matrix exhibited similar trends to tissue-derived matrices. FIG. 12A is a Western blot revealing successful reduction of TSP-2 expression in MC3T3-E1 cells via transfection of an shRNA. FIG. 12B is a Western blot of pre-gel demonstrating that the TSP-2 KD gels exhibit a reduction in the expression of Collagen I. Rheology showed that hydrogels prepared from MC3T3-E1 CDM exhibit similar trends to tissue-derived hydrogels with the vector control exhibiting a higher modulus than TSP-2 KD (n=6) (rheological traces are given as mean±SEM) (FIG. 12C), with quantification of the maximal storage modulus demonstrating a significant reduction in the TSP-2 KD samples (FIG. 12D). Results are given as mean+SEM, (n=6), **p<0.01. FIG. 12E is an SDS-PAGE image showing changes in protein content for TSP-2 KD hydrogels. A Coomassie Blue stain revealed changes in protein content of hydrogels derived from CDM from TSP-2 KD MC3T3-E1 cells as compared to WT.

DETAILED DESCRIPTION OF THE INVENTION

In one aspect, the present invention relates to novel compositions and methods for treating a wound, or location (or region) of interest, in a mammal by administering a decellularized extracellular matrix (ECM) lacking thrombospondin-2 (TSP-2-null ECM).

The invention provides an acellular composition comprising a decellularized TSP-2-null ECM. In certain embodiments, the invention provides a tunable hydrogel comprising a decellularized TSP-2-null ECM. The invention also provides methods for accelerating cellular migration, methods for enhancing cellular invasion, methods for enhancing vascular growth and maturation of a location to be treated, and/or methods for enhancing a wound repair in a mammal in need thereof. In certain embodiments, the method comprises administering to the location or wound to be treated an acellular composition comprising a decellularized TSP-2-null ECM.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

By "alteration" is meant a change (increase or decrease) in the expression levels or activity of a marker or clinical indicator as detected by standard art known methods such as those described herein. As used herein, an alteration includes a 10%-100% change in measured levels (e.g., 10, 20, 30, 40, 50, 60, 75, 80, 85, 90, 95, 100%).

The term "biocompatibility" refers to the properties of materials, such as a medical device or an implant, device being biologically compatible by not eliciting local or systemic responses from a living system or tissue. In other embodiments, the device does not elicit any significantly and/or measurably deleterious responses from the living system or tissue. A biocompatible device is substantially non-toxic, non-injurious or non-inhibiting or non-inhibitory to cells, tissues, organs, and/or organ systems that would come into contact with the device, scaffold, composition, etc.

The term "coating" refers to a covering, layer or film, of a substance applied to the surface of a substrate. The coating may be an all-over coating, completely covering the substrate, or it may only cover parts of the substrate.

As used herein, the term "comminute" and any other word forms or cognates thereof, such as, without limitation. "comminuting", refers to the process of reducing larger particles into smaller particles, including, without limitation, by grinding, blending, shredding, slicing, milling, cutting ECM can be comminuted while in any form, including, but not limited to, hydrated forms, frozen, air-dried, lyophilized, powdered, sheet-form.

The expression "difference in the level of" or "differentially present" refers to differences in the quantity and/or the frequency of a marker present in a sample taken from subjects having a disease as compared to a control subject. A marker can be differentially present in terms of quantity, frequency or both. A difference in the level of a polypeptide is present between two samples if the amount of the polypeptide in one sample is statistically significantly different from the amount of the polypeptide in the other sample. Alternatively or additionally, a polypeptide is differentially present between two sets of samples if the frequency of detecting the polypeptide in a diseased subjects' samples is statistically significantly higher or lower than in the control samples. A marker that is present in one sample, but undetectable in another sample is differentially present.

A "disease" is a state of health of an animal wherein the animal cannot maintain homeostasis, and wherein if the disease is not ameliorated then the animal's health continues to deteriorate. "Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The terms "extracellular matrix" or "ECM" refer to proteins that are secreted by cells and assembled in a three dimensional manner to provide structural support for cells. Generally, extracellular matrix comprises proteins such as collagens (e.g. type I, III, IV, and V collagens), vitronectin, fibronectin, laminin, thrombospondin, entactin, and nidogen; and glycosaminoglycans and proteoglycans. However, it is noted that the extracellular matrix can vary in composition, and structural assembly, depending on its anatomic origin. In some instances, ECMs include an isolated basement membrane produced by vascular endothelial cells and a membrane on which the cells rest in vivo. Non limiting examples of ECMs are ones produced using fibroblasts (primary dermal fibroblasts, as well as cell lines MC3T3s and NIH3T3s) and primary smooth muscle cells. While matrices may differ somewhat in their composition, they are primarily composed of collagens (e.g. type I, III. IV. VI collagens), fibronectin, laminins, and other matricellular proteins. Despite the variation due to anatomic origin, extracellular matrix from any anatomic site could be useful in the present invention. Of particular interest in the present invention, are ECMs that comprise extracellular molecules that form a three-dimensional structure supporting cell and tissue growth. The molecules and structure secreted by matrix-producing cells could be produced in in vitro.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a host response to an antigen that occurs when lymphocytes identify antigenic molecules as foreign and induce the formation of antibodies and/or activate lymphocytes to remove the antigen.

As used herein, the terms "immunosuppression" or "immunosuppressive therapy (IST)" involve an act that reduces the activation or efficacy of the immune system. Deliberately induced immunosuppression is performed to prevent the body from rejecting an organ transplant, treating graft-versus-host disease after a bone marrow transplant, or for the treatment of auto-immune diseases such as rheumatoid arthritis or Crohn's disease.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

By "marker" is meant any protein or polynucleotide having an alteration in level or activity that is associated with a disease or disorder.

By the term "modified" as used herein, is meant a changed state or structure of a molecule or cell of the invention. Molecules may be modified in many ways, including chemically, structurally, and functionally. Cells may be modified through the introduction of nucleic acids therein.

The term "model organism" refers to a non-human species that is easy to maintain and breed in a laboratory setting and has particular experimental advantages. Model organisms as used herein provide an in vivo model to research the effects of a human disease or condition and/or biological activities associated with a disease or condition, such as thrombosis.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Monitoring" refers to recording changes in a continuously varying parameter (e.g. monitoring progression of a disease).

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose: starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative: antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The terms "purified", "biologically pure" or "isolated" as used herein mean having been increased in purity, wherein "purity" is a relative term, and not to be necessarily construed as absolute purity. For example, the purity of a substance, for example, but not limited to a nucleic acid, can be at least about 50%, can be greater than 60%, 70%, 80%, 90%, 95%, or can be 100%. The terms "purified", "biologically pure" or "isolated" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, "sample" or "biological sample" refers to anything, which may contain an analyte (e.g., polypeptide, polynucleotide, or fragment thereof) for which an analyte assay is desired. The sample may be a biological sample, such as a biological fluid or a biological tissue. In certain embodiments, a biological sample is a salivary sample. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

By the term "specifically binds," as used herein with respect to an antigen binding molecule is meant an antigen binding molecule which recognizes a specific antigen, but does not substantially recognize or bind other molecules in a sample. For example, an antigen binding molecule that specifically binds to an antigen from one species may also bind to that antigen from one or more species. But, such cross-species reactivity does not itself alter the classification of an antigen binding molecule as specific. In another example, an antigen binding molecule that specifically binds to an antigen may also bind to different allelic forms of the antigen. However, such cross reactivity does not itself alter the classification of an antigen binding molecule as specific. In some instances, the terms "specific binding" or "specifically binding," can be used in reference to the interaction of an antigen binding molecule, an antibody, a protein, or a peptide with a second chemical species, to mean that the interaction is dependent upon the presence of a particular structure (e.g., an antigenic determinant or epitope) on the chemical species; for example, an antigen binding molecule or an antibody recognizes and binds to a specific protein structure rather than to proteins generally. If an antigen binding molecule is specific for epitope "A", the presence of a molecule containing epitope A (or free, unlabeled A), in a reaction containing labeled "A" and the antigen binding molecule, will reduce the amount of labeled A bound to the antigen binding molecule.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "host" (or "recipient"). An organ, or graft, transplanted between two genetically different individuals of the same species is called an "allograft". A graft transplanted between individuals of different species is called a "xenograft".

As used herein, "transplant rejection" refers to a functional and structural deterioration of the organ due to an active immune response expressed by the recipient, and independent of non-immunologic causes of organ dysfunction.

As used herein, the term "tolerance" is a state of immune unresponsiveness specific to a particular antigen or set of antigens induced by previous exposure to that antigen or set. Tolerance is generally accepted to be an active process and, in essence, a learning experience for T cells. Tolerance, as used herein, refers to the inhibition of a graft recipient's ability to mount an immune response which would otherwise occur, e.g., in response to the introduction of a non-self MHC antigen into the recipient. Tolerance can involve humoral, cellular, or both humoral and cellular responses.

To "treat" a disease as the term is used herein, means to reduce the frequency or severity of at least one sign or symptom of a disease or disorder experienced by a subject. It will be appreciated that, although not precluded, treating a disorder or condition does not require that the disorder, condition or symptoms associated therewith be completely eliminated.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: ADM, acellular dermal matrix; CDM, cell-derived matrix; ECM, extracellular matrix; HA, hyaluronic acid; H&E, hematoxylin and eosin; HUVECs. Human umbilical vein endothelial cell; KO, knock-out; SEM, scanning electron microscope; TSP-2-null ECM, decellularized extracellular matrix lacking thrombospondin-2; WT, wild-type.

DESCRIPTION

The present invention relates to compositions and methods for treating a wound, or location of interest, in a mammal. In certain embodiments, the mammal is administered a decellularized extracellular matrix (ECM) lacking thrombospondin-2 (TSP-2-null ECM).

In certain embodiments, the invention provides an acellular composition comprising a decellularized TSP-2-null ECM. In other embodiments, the invention provides a tunable hydrogel comprising a decellularized TSP-2-null ECM. In yet other embodiments, the decellularized TSP-2-null ECM is chemoattractant to at least one cell type selected from the group consisting of endothelial cell, mesenchymal cell, fibroblast, and osteoblast. In yet other embodiments, the compositions of the invention are useful for the methods recited elsewhere herein.

METHODS OF THE INVENTION

The invention provides methods for accelerating cellular migration, methods for enhancing cellular invasion, methods for enhancing vascular growth and maturation of a location to be treated, and methods for enhancing wound repair in a mammal in need thereof. In certain embodiments, the methods of this invention comprise administering to the location or wound to be treated an acellular composition comprising a decellularized TSP-2-null ECM, whereby cellular migration, cellular invasion, vascular growth and maturation, and/or wound repair are enhanced or accelerated as compared to a location administered a wild typeECM or untreated.

In certain embodiments, the decellularized TSP-2-null ECM is derived from at least one selected from the group consisting of a primary matrix-producing cell, a fibroblast, an osteoblast, and a smooth muscle. In certain embodiments, the decellularized TSP-2-null ECM is combined with a wild type ECM.

Generation of Decellularized TSP-2-Null ECM
Obtaining ECM

The ECM is obtained using methods known to those skilled in the art. In certain embodiments, the ECM is isolated from a mammalian tissue. As used herein, the term "mammalian tissue" refers to tissue derived from a mammal, wherein the tissue comprises any cellular component of an animal. For example and without limitation, tissue can be derived from aggregates of cells, an organ, portions of an organ, or combinations of organs. In some instances, the ECM is isolated from a vertebrate animal, for example and without limitation, human, monkey, pig, cattle, and sheep. In other instances, the ECM is isolated from any tissue of an animal, for example and without limitation, urinary bladder, liver, central nervous system (CNS), adipose tissue, small intestine, large intestine, colon, esophagus, pancreas, dermis, and heart.

In certain embodiments. ECM can be obtained as an in vitro structure by isolating primary matrix-producing cells or plating matrix producing cells from established cell lines and culturing them in the presence of an inducer of matrix deposition, such as ascorbic acid, to aid in the excretion of collagen molecules for 3 to 60 days depending on the intended need thereof. A decellularization of the ECM is then performed via a short wash (2-10 minutes) with a basic wash solution (e.g. 40 mM ammonium hydroxide and 0.5% triton X-100) at a temperature range of 25° C. to 37° C. In certain embodiments, the ECM is subsequently treated with DNAse to circumvent the possibility of genomic DNA contamination. DNAse treatment is generally performed at a temperature range of 25° C. to 37° C. for about 1 hour.

The ECM is the natural substrate on which cells migrate, proliferate, and differentiate. These components are linked in such a way that the resulting structure is tri-dimensional scaffolding in vivo. Thus, the ECM provides scaffolding, support and strength to cells grown on it, allowing those cells to differentiate and mediate physiologic responses. ECMs from different anatomic sites may vary in their ability to support and allow for proper differentiation of cells not from that respective anatomic site. Further, without wishing to be bound by any theory, the ECM should ideally be produced from cells derived from the same species as the recipient or from species known to in the art to have compatibility with the recipient. In certain embodiments, if the recipient is a human, a non-limiting ECM is a matrix made from human vascular endothelial cells, since it is the most natural surface for such endothelial cells; and provides matrix recognition domains and corresponding cell receptors specific for, and enhancing the growth of, human vascular endothelial cells that colonize and modify the graft subsequent to coating. In other embodiments, if the recipient is a human, the ECM matrix originates from an animal known to have compatibilities with humans such as, but not limited to, a primate or a pig.

Decellularized TSP-2-Null ECM

Generation of a TSP-2-null ECM can be accomplished in a number of ways. In some aspects, the absence of expression of the TSP-2 gene in the ECM may result from a full or partial knock-out of the TSP-2 gene. Methods of gene knock-out are well known in the art. Briefly, a gene knock-out refers to a genetic technique in which one of an organism's genes is made inoperative. Knock-out is accomplished through a combination of well-established molecular techniques. In general, individual stem cells are genetically transfected with the DNA construct for the goal of creating a transgenic animal that has the altered gene. Embryonic stem cells are genetically transformed and inserted into early embryos. The resulting transgenic animals with the genetic alteration in their germline cells then pass the knock-out to future generations. For instance, a knock-out mouse refers to a mouse in which a gene or genes have been mutated such that the activity of the gene has been reduced or eliminated. Of particular interest for the present invention, the thrombospondin-2 (TSP-2) gene is knocked out in a genetically engineered animal such as a mouse or a pig. In other aspects, TSP-2 gene is knocked down using other molecular techniques known in the art such as, but not limited to. RNA interference (RNAi), small hairpin RNA (shRNA) and Clustered Regularly Interspaced Short Palindromic Repeats (CRISPRs). Knocked-down expression of TSP-2 is useful for generation of TSP-2-null ECM in mammals where knock-out of TSP-2 is not possible. e.g., in humans. Thus, the term "TSP-2-null ECM" as used herein should be construed to mean ECM derived from a mammalian tissue where the mammal comprises a TSP-2 knockout genotype as well as ECM derived from a mammalian tissue where expression of TSP-2 in the tissue has been knocked down using any means available in the art. In the latter instance, expression of TSP-2 may be diminished when compared with wild type expression, and/or may be eliminated altogether. In some aspects, the characteristics of a TSP-2-null ECM produced by a TSP-2 knock-down are optimized and similar to the ones produced by a TSP-2 knock-out.

The TSP-2-null ECM composition of this invention can be decellularized by methods known in the art. In one aspect, decellularization is performed to prevent a pro-inflammatory response. As such, in one aspect, a decellularized ECM product refers to ECM material that is decellularized to the extent that a pro-inflammatory response, and thus growth of fibrotic tissue, is not elicited to any substantial degree in favor of constructive remodeling.

In certain embodiments, the decellularized TSP-2-null ECM as described herein retains activity of at least a portion of its structural and non-structural biomolecules, including, but not limited to, collagens, elastins, laminins, glycosaminoglycans, proteoglycans, antimicrobials, chemoattractants, cytokines, and/or growth factors. In certain embodiments, the activity of the biomolecules within the TSP-2-null ECM can be removed chemically or mechanically, for example, by cross-linking and/or by dialyzing the ECM. In one aspect, the decellularized ECM composition of this invention is cross-linked by addition of a chemical cross-linking agent. In other aspect, the ECM materials described herein essentially have not been cross-linked and/or dialyzed. Thus, in one aspect, the ECM material is not cross-linked and/or dialyzed in anything but a trivial manner which does not substantially affect the gelation and functional characteristics of the TSP-2-null ECM material in its uses described herein.

Formulation of the TSP-2-Null ECM

In one embodiment, the decellularized TSP-2-null ECM of this invention is formulated as sheet of material such as but not limited to STRATTICE™ or ALLODERM™ regenerative tissue matrix (Allergan, Dublin, Ireland).

In another embodiment, the decellularized TSP-2-null ECM is formulated in at least one selected from the group consisting of a silicone and a hydrogel.

In certain embodiments, the decellularized TSP-2-null ECM is formulated in a hydrogel with tunable properties. In some instances, the hydrogel is a reverse gel, which forms a gel upon an increase in temperature. As the temperature rises above a certain temperature in a reverse gel, a hydrogel is formed. The general concept of reverse gelation of polymers and, e.g., its relation to lower critical solution temperature (LCST) are broadly known in the chemical arts. The ECM compositions described herein are prepared, for example, from decellularized or devitalized, intact ECM as described elsewhere herein. An ECM gel is prepared by digestion of the ECM material with an acid protease, neutralization of the material to form a pre-gel, and then raising the temperature of the pre-gel above a gelation temperature, for example the LCST of the pre-gel, to cause the pre-gel to become a gel. As used herein, the term "gel" includes hydrogels. The transition temperature for acid-protease-digested from solution to gel is typically within the range of from about 10° C. to 40° C. and any increments or ranges therebetween, for example from about 20° C. to 35° C. For example, the pre-gel can be warmed to about 37° C. to form a hydrogel.

Tissue for preparation of ECM, ECM-derived pre-gel solutions, and gels as described herein may be harvested in any useful manner. Decellularized or devitalized ECM can be dried, either lyophilized (freeze-dried) or air dried. The ECM composition is optionally comminuted at some point, for example prior to acid protease digestion in preparation of an ECM gel, for example prior to or after drying. In certain embodiments, the decellularized TSP-2-null ECM of the invention is comminuted. The comminuted ECM can also be further processed into a powdered form by methods, for example and without limitation, such as grinding or milling in a frozen or freeze-dried state.

In order to prepare solubilized ECM tissue, the ECM is digested with an acid protease in an acidic solution to form a digest solution. As used herein, the term "acid protease" refers to an enzyme that cleaves peptide bonds, wherein the enzyme has increased activity of cleaving peptide bonds in an acidic pH. For example and without limitation, acid proteases include pepsin and trypsin and mixtures thereof.

As an example, the digest solution of ECM is kept at a constant stir for a certain amount of time at room temperature. In one aspect, the pH is maintained at less than pH 4.0 or at pH 2.0±0.3 during acid protease digestion of the decellularized tissue as described herein. The ECM digest can be used immediately or can be stored at −20° C. or frozen at, for example and without limitation, −20° C. or −80° C. In certain aspects, the ECM digest is snap frozen in liquid nitrogen. To form a "pre-gel" solution, the pH of the digest solution is raised to a pH between 6.8 and 7.8. The pH can be raised by adding one or more of a base or an isotonic buffered solution, for example and without limitation, NaOH or PBS at pH 7.4. In some aspect, the pre-gel solution is freeze dried and stored at −20° C. or −80° C. until needed. The method optionally does not include a dialysis step prior to gelation, yielding a more complete ECM-like matrix that typically gels at 37° C. more slowly than comparable collagen or dialyzed ECM preparations. The gel therefore retains more of the qualities of native ECM due to retention of many native soluble factors, such as, without limitation, cytokines. Without intending to be limited to any particular theory, these factors contribute to chemoattraction of cells and proper rearrangement of tissue at the site of wound or injury, rather than a fibrotic response that leads to unwanted scarring. In other embodiments, the ECM is dialyzed prior to gelation to remove certain soluble components.

As used herein, the term "isotonic buffered solution" refers to a solution that is buffered to a pH between 6.8 and 7.8, e.g., pH 7.4, and that has a balanced concentration of salts to promote an isotonic environment. As used herein, the term "base" refers to any compound or a solution of a compound with a pH greater than 7. For example and without limitation, the base is an alkaline hydroxide or an aqueous solution of an alkaline hydroxide. In certain embodiments, the base is NaOH, or NaOH in PBS. This "pre-gel" solution can, at that point be incubated at a suitably warm temperature, for example and without limitation, at about 37° C. to gel.

In the method of preparing an ECM gel, the ECM may be partially or completely digested with the acid protease, such as pepsin. The digested ECM is then neutralized to a pH of 6.8-7.8, e.g., 7.2-7.6, or 7.4 and the neutralized and digested ECM material is gelled by incubation at a temperature at which the material gels, e.g., at a temperature above 20, 25, 30, or 35° C., such as at 37°. The degree of digestion can be determined by comparison on a gel, or by ascertaining the degree of degradation of hyaluronic acid, for example by Western blot (anti-hyaluronic acid antibodies are commercially-available from multiple sources) or chromatographic methods, as are broadly known. For example in a partial digestion, hyaluronic acid is digested less than 50%, 40%, 30%, 25%, 20% or 10%.

Compositions and methods of the present invention are useful for treatment of mammals, and particularly humans. In certain embodiments, the mammal is immune compromised, suffers from an autoimmune disease, has or will have transplant, or suffers from a condition with high risk for wounds. In certain embodiments, the mammal suffers from at least one condition selected from the group consisting of: diabetes, hernia, mastectomy, peripheral vascular disease, and neuropathy. In certain embodiments, the mammal is in need for regenerative medicine to replace or repair a tissue or organ that has been damaged by a disease, a trauma or a congenital issue (such as, but not limited to, empty nose syndrome). In other embodiments, the compositions and methods of the present invention are useful for aesthetic purposes.

Cell-Derived Matrix Hydrogels

The invention further provides a Cell-Derived Matrix (CDM) hydrogel composition comprising an extracellular matrix produced by cells cultured in an in vitro environment. In certain embodiments, the hydrogel is made by culturing one or more cells in a cell culture such that an extracellular matrix (ECM) is produced, decellularizing the cell culture such that the ECM remains substantially intact, optionally contacting the ECM with an acid protease, and forming a hydrogel from the ECM material.

In certain embodiments, the CDM hydrogel is derived from at least one cell type selected from the group consisting of dermal fibroblast cells, osteoblast cells, cardiac fibroblast cells, smooth muscle cells, mesenchymal stem cells and embryonic stem cells. In other embodiments, the at least one cell type is a type of fibroblast cell. In other embodiments, the CDM hydrogel is derived from a wild-type cell line or a genetically modified cell line. In yet other embodiments, the CDM hydrogel is derived from a TSP-2 knockout cell line. In yet other embodiments, the CDM hydrogel is derived from an immortalized cell line.

In certain embodiments, the hydrogel is a reverse gel, which forms a gel upon an increase in temperature. As the temperature rises above a certain temperature in a reverse gel, a hydrogel is formed. The general concept of reverse gelation of polymers and, e.g., its relation to lower critical solution temperature (LCST) are broadly known in the chemical arts. In certain embodiments, the CDM gel is prepared by digestion of the cell culture derived ECM material with an acid protease, neutralization of the material to form a pre-gel, and then raising the temperature of the pre-gel above a gelation temperature, for example the LCST of the pre-gel, to cause the pre-gel to become a gel. As used herein, the term "gel" includes hydrogels. The transition temperature for acid-protease-digested from solution to gel is typically within the range of from about 10° C. to 40° C. and any increments or ranges therebetween, for example from about 20° C. to 35° C. For example, the pre-gel can be warmed to about 37° C. to form a hydrogel.

Decellularized CDM can be dried, either lyophilized (freeze-dried) or air dried. The CDM composition is optionally comminuted at some point, for example prior to acid protease digestion in preparation of an CDM gel, for example prior to or after drying. In certain embodiments, the decellularized TSP-2-null CDM of the invention is comminuted. The comminuted CDM can also be further processed into a powdered form by methods, for example and without limitation, such as grinding or milling in a frozen or freeze-dried state.

In the method of preparing an CDM gel, the CDM may be partially or completely digested with the acid protease, such as pepsin. The digested ECM is then neutralized to a pH of 6.8-7.8, e.g., 7.2-7.6, or 7.4 and the neutralized and digested CDM material is gelled by incubation at a temperature at which the material gels, e.g., at a temperature above 20, 25, 30, or 35° C., such as at 37°. The degree of digestion can be determined by comparison on a gel, or by ascertaining the degree of degradation of hyaluronic acid, for example by Western blot (anti-hyaluronic acid antibodies are commercially-available from multiple sources) or chromatographic methods, as are broadly known. For example in a partial digestion, hyaluronic acid is digested less than 50%, 40%, 30%, 25%, 20% or 10%.

The invention provides hydrogels derived from CDM. When the source cells are genetically manipulated, similar phenotypes occur to what is observed for tissue derived hydrogels. This allows for more rapid genetic engineering of ECM derived hydrogels, since genetically manipulating whole animals is not necessary in order to procure a modified ECM material. This method can be performed with human or porcine cells to rapidly create genetically engineered matrix materials suitable for clinical translation.

Combination Therapies

The decellularized TSP-2-null ECM compound described herein is also useful when combined with at least one additional compound. The additional compound may comprise commercially available compounds known to treat, prevent, or reduce the symptoms associated with graft transplants or implantation of a device into a subject.

In one aspect, the present invention contemplates that the decellularized TSP-2-null ECM of the invention may be used in combination with a therapeutic agent such as an immunosuppressive agent. Non-limiting examples of immunosuppressive agents known in the art are cyclosporine, azathioprine, everolimus and glucocorticoids, mycophenolic acid, fingolimod, antimetabolites (such as, but not limited to, methotrexate, fluorouracil), antibiotics (such as, but not limited to, dactinomycin, mitomycin C, bleomycin), and antibodies (such as, but not limited to, Atgam, Muromonab-CD3, basiliximab, daclizumab).

In another aspect, the present invention provides the decellularized TSP-2-null ECM of the invention as a delivery vehicle for one or more active pharmaceutical agents or drugs. In certain embodiments, the decellularized TSP-2-null ECM of the invention further comprises at least one active pharmaceutical agent selected from the group consisting of a Rac1 inhibitor, a NFKB inhibitor, a p38 MAPK inhibitor, a RhoA inhibitor, a growth factor (including, but not limited to, VEGF, PDGF and BMP-2), Fasudil, Ripasudil, antibiotics, immune modulators (including, but not limited to, IL-4, IL-33 and IL-10), an anti-inflammatory (including, but not limited to, glucocorticoids and NSAIDs), a cytokine and oligonucleotides (including, but not limited to, siRNA, shRNA, plasmid DNA, and/or virus for gene therapy). In yet other embodiments, the at least one active pharmaceutical agent is an anti-inflammatory drug that influences the response of macrophages, such as, but not limited to BAY-11. In yet other embodiments, the at least one pharmaceutical agent is selected from the group consisting of CAS 1177865-17-6. SB 202190 SB203580, RKI-1447, and Y-27632.

Pharmaceutical Compositions and Formulations.

The invention includes the use of a pharmaceutical composition combined with the decellularized TSP-2-null ECM preparation as described herein for use in the methods of the invention. The invention also includes the use of a pharmaceutical composition combined with the CDM hydrogel preparation as described herein for use in the methods of the invention.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease or wound being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions are formulated using one or more pharmaceutically acceptable excipients or carriers. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences, 1991, Mack Publication Co., New Jersey.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Kit

In one aspect of the invention, a commercial kit is provided comprising the decellularized TSP-2-null ECM composition described herein. A kit comprises suitable packaging material and the composition. In certain embodiments, the kit comprises a decellularized tissue as a sheet of material (e.g. STRATTICE™ or ALLODERM™) or a digest solution in a vessel, which may be the packaging, or which may be contained within packaging. In one embodiment, if the sheet of material or digest solution is neutralized, it may be frozen, cooled, e.g., kept at near-freezing temperatures, such as, without limitation, below about 4° C. or kept at room temperature, e.g., 20-25° C. In another embodiment, the kit comprises a first vessel containing an acidic solution comprising a pre-neutralization digest as described elsewhere herein, and a second vessel comprising a neutralizing solution comprising a base and/or buffer(s) to bring the acidic solution of the first vessel to physiological ionic strength and pH, to form a neutralized digest. In a further embodiment, the first vessel contains a terminally sterilized, lyophilized, pre-neutralization digest that can be hydrated using water or a suitable aqueous solution that optionally neutralizes the acid. In this embodiment, a second vessel is optionally provided comprising a neutralization solution as described above that is capable of both hydrating the lyophilized product and neutralizing it, or optionally a third vessel comprising water or any other suitable solution useful in hydrating the lyophilized product prior to neutralization with the neutralization solution. This kit also optionally comprises a mixing needle and/or a cold-pack. The vessel may be a vial, syringe, tube or any other container suitable for storage and transfer in commercial distribution routes of the kit.

Administration/Dosing

The regimen of administration may affect what constitutes an effective amount. Several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

The compositions described herein find use as, without limitation, an injectable graft (e.g., xenogeneic, allogeneic or autologous) for tissues, for example, bone or soft tissues, in need of repair or augmentation most typically to correct a wound, a trauma or disease-induced tissue defects. The compositions also may be used as a filler for implant constructs comprising, for example, a molded construct formed into a desired shape for use in cosmetic or trauma-treating surgical procedures.

Administration of the compositions of the present invention to a subject (being a patient), preferably a mammal, more preferably a human, may be carried out using known procedures, at dosages and for periods of time effective to treat the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday. and so on. The frequency of the dose is readily apparent to the skilled artisan and depends upon any number of factors, such as, but not limited to, the type and severity of the disease being treated, and the type and age of the animal. Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient. A medical doctor. e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of wound in a patient.

Routes of Administration

One skilled in the art will recognize that although more than one route can be used for administration, a particular route can provide a more immediate and more effective reaction than another route.

Routes of administration of any of the compositions of the invention include parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration. Suitable compositions and dosage forms include, for example, sheets of material (e.g. STRATTICE™ or ALLODERM™) that could be sutured into wounds or used as supporting meshes/slings, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Particularly, the compositions may be implanted into a patient, human or animal, by a number of methods. In certain embodiments, the compositions are injected as a liquid into a desired site in the patient. As used herein, the term "seed," "seeding," or "seeded" refers to the addition, incorporation, propagation of, or spreading of a defined volume of a cell suspension or a defined cell number into a specific composition. The composition may be pre-seeded with cells, and then preferably injected using a larger-bore, e.g. 16 gauge needle, to prevent shearing of cells. In another embodiment, the composition is gelled within a mold (e.g. a silicone mold) or formulated as a hydrogel, and the gelled, molded product or the hydrogel product is then implanted into the patient at a desired site. The gelled, molded product may be pre-seeded (laid onto the molded gel or mixed in during gelation) with cells, such as cells of the patient.

In certain embodiments, the administration of the decellularized TSP-2-null ECM or CDM hydrogel is at least one selected from the group consisting of subcutaneous and topical. In other embodiments, the composition of the invention is injected, seeded or surgically implanted to the region to be treated.

In certain embodiments, the composition of the invention is applied to a bandage or dressing, which is then applied to the wound or treatment site of a subject. For example, in one embodiment, a dressing is soaked in a liquid solution or liquid suspension comprising decellularized TSP-2-null ECM or CDM hydrogel. In another embodiment, an ointment comprising decellularized TSP-2-null ECM is applied to a surface of a dressing or bandage. In yet other embodiments, the decellularized TSP-2-null ECM or CDM hydrogel is incorporated into a pharmaceutical formulation including topical ointments, creams, aerosol sprays, and the like.

In certain embodiments, the administration route is a continuous subcutaneous administration for at least 2 days. In another embodiment, the administration route is a continuous subcutaneous administration for at least 20 days. In yet another embodiment, the administration route is a continuous subcutaneous administration for at least 30 days.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials and Methods for Examples 1-6

Isolation and Decellularization of Murine Skin

Isolation and decellularization of murine skin was conducted (Morris, et al., *BioResearch Open Access*, 5(1): 177-187, 2016). Briefly, 12-14 week old mice on a C57BL/6 background were shaved and treated with depilatory cream to remove hair. Skins were subsequently harvested, flash frozen, and stored at −80° C. until use. Skins were incubated for 6 hours in 0.25% Trypsin-EDTA (J.T. Baker), followed by washes in ddH20 three times for 15 minutes. Skins were incubated in 70% ethanol for 12 hours and 3% H202 (Sigma) for 15 minutes, followed by two 15 minute washes in ddH20. Skins were then incubated in 1% Triton X-100 (American Bioanalytical) in 0.69% Tris (American Bioanalytical)/0.26% EDTA (Sigma) for 6 hours and then overnight. Skins were terminally sterilized in 0.1% peracetic acid in 4% ethanol for two hours. Finally, skins were washed in ddH20 six times for fifteen minutes each. All above steps were performed at room temperature on an orbital shaker. Skins received a final wash in serum-free Dulbeccos Modified Eagles Medium (DMEM; Gibco) with 1% penicillin/streptomycin (Pen Strep; Gibco) on a rotating shaker at 37° C. for 24 hours. Afterward, skins were lyophilized and stored at −80° C. until use. Samples of each skin were fixed, prepared for histological analysis, and then stained with hematoxylin and eosin using standard protocols. For scanning electron microscopy (SEM), samples were mounted to an SEM stub with carbon tape and coated with approximately 8 nm of iridium and imaged with a Hitachi SU-70 SEM.

Tensile Testing

Lyophilized skins were cut into dogbone shaped specimens using a scalpel and laser cut stencil. Samples were then permitted to rehydrate in PBS for at least 5 minutes before testing and were kept hydrated during testing. Tissue thickness of each sample was determined by measuring the thickness at 3 points within the narrow section using a Mitutoyo digital micrometer. Samples were glued to sections of sandpaper at the end of their length and mounted into the grips attached to the 10 N load cell of the Instron 5848. Tissues were pulled until failure at a rate of 3.3 mm/min, (n=3). Engineering stress and strain were calculated from force, distance, and tissue dimensions according to the following equations where $\sigma$ is engineering stress, F is force. Ag is initial cross-sectional area, F is engineering strain, $l_f$ is final length, and $l_o$ is initial length:

$$\sigma = \frac{F}{A_0}$$

$$\varepsilon = \frac{l_f - l_0}{l_0}$$

Biochemical Analysis

Collagen content was determined using a hydroxyproline assay (QUICKZYME®) according to manufacturer's instructions (n=7). Sulfated glycosaminoglycan (sGAG) content was determined using the Blyscan sGAG assay (BIOCOLOR®). Samples were digested in papain overnight at 65° C. overnight before proceeding with protocol according to manufacturer's instructions (n=3). Residual DNA was quantified with a DNeasy Blood & Tissue Kit (Qiagen) according to manufacturer's instructions (n=3).

Denaturation Analysis

To analyze denaturation, a protocol described by Hwang, et al. was used (Hwang, el al., *Acta Biomaterialia*, 53:268-278, 2017). The collagen hybridizing peptide (CHP), GGG-(GPO)$_9$. (O represents hydroxyproline) with an N-terminal FITC tag was synthesized by United Peptide. Prior to lyophilization, constructs were embedded in OCT mounting medium (TISSUETEK®). 8 μm thick sections were cut and mounted on slides. WT, and TSP-2 KO construct sections were mounted. Additionally, native WT skin and heat denatured native WT skin were mounted as controls. Heat denaturation was accomplished by incubating section for 10 minutes at 95° C. Samples were washed 3 times for 5 minutes with PBS before being incubated in 30 μM FITC-CHP in PBS for 2 hours at 4° C. Samples were rinsed 3 times for 5 minutes in PBS before mounting in VECTASHIELD® Mounting Medium (Vector Labs) and imaging. Three 10× images of each sample were quantified in Image J to determine the integrated density of the FITC signal. Data were then normalized to a percent of the heat denatured control sample. Three experiments were performed (n=3).

Enzymatic Degradation Kinetics

Enzymatic degradation was performed as an accelerated measure of in vivo degradation. First constructs were massed and cut into 1×1 cm squares, type IV collagenase (50 U/mL, Sigma) or pepsin (1 mg/mL, Sigma) in PBS (for collagenase) or 0.0 IN HCL (for pepsin) was added for a final concentration of 5 mg dry weight skin/mL. Samples were incubated at 37° C. At specified time points, mixture was centrifuged at 18,000 g for 1 minute. 20 uL samples of the digest solution were collected at each time point and stored at −20° C. until analysis. Protein concentration of the releasate was evaluated with the Bradford Assay (BioRad) against a BSA standard curve (n=3).

Cell Culture

Cells were maintained in vitro with standard protocols. Briefly, mouse embryonic fibroblast cell line NIH3T3 (ATCC), primary dermal fibroblasts, and RAW 264.37 (ATCC) cells were maintained in growth medium, DMEM (Gibco) with 10% FBS and 1% pen strep. The mouse preosteoblastic cell line MC3T3-E1 was maintained in growth medium, αMEM with 10% FBS and 1% pen strep. Human umbilical cord vein cells (HUVECs, Yale VBT Core Facility) were maintained in M199 medium (Gibco) supplemented with 20% FBS and 1% pen strep and 3% endothelial cell growth supplement (ECGS).

ECM Solubilization

To analyze the chemoattractant properties of constructs, concentrated degradation products were produced by incubating constructs at 10 mg dry weight per mL fluid in a solution of 1 mg/mL pepsin in 0.01 N HCl (Sigma) for 72 hours (Reing, et al., Tissue engineering. Part A, 15(3):605-14, 2009). Degradation products were then neutralized and buffered with 1/10th the digest volume of NaOH and 1/9th the digest volume of 10×PBS.

To create media containing degradation products, solubilized ECM was added to cold serum-free media (appropriate medium selected based on cells) at a final matrix concentration of 50 µg/mL and stored at −20° C. until use. Cells were serum-starved overnight before use. NIH3T3, MC3T3-E1, and RAW 264.37 cells were starved in serum free media and HUVEC were starved in 0.5% FBS. TRANSWELLS® with 8 µm pores (Corning) were coated with 50 µg/mL collagen I (BD) for 30 minutes at 37° C. Cells were harvested by addition of 0.25% Trypsin/EDTA. A suspension of 50,000 cells was added to each TRANSWELL® in 100 µl serum free media. 600 µl media containing degradation products or pepsin control was added to the bottom of the well and cells were allowed to migrate for 6 hours at 37° C., before being fixed in 100% methanol and stained with a modified Giemsa-May Grunwald stain (Diff-Quik). Wells were imaged at 20× and quantified by measuring the number of cells per image (n=3).

Subcutaneous Implantation

Decellularized skin was comminuted. Constructs were passed through a Wiley mini mill (Thomas Scientific, Swedesboro, N.J.) and stored at −80° C. until use. Silicone trays were used for subcutaneous implantation, because of the difficulty of retrieving powdered matrix after implantation. The trays were fabricated by cutting two 6 mm squares of silicone and punching a 4 mm biopsy punch through one of them. The two squares were then treated with oxygen plasma and allowed to form a permanent bond. After tray fabrication, matrix was loaded into the tray to create a layered silicone, matrix product (Dearth, et al., Tissue Engineering Part A, 21(19-20): 2526-2535, 2015). 4 mm intact slabs of decellularized matrix were placed in the trays and implanted upright so that the ECM was in contact with the dermis.

Subcutaneous (SC) implantations were performed (Morris, et al., BioResearch Open Access, 5(1): 177-187, 2016; Morris, et al., Advanced Healthcare Materials, 1700370: 1700370, 2017; Kyriakides, et al., The Journal of Investigative Dermatology, 113(5): 782-787, 1999). Trays were implanted SC for 2 weeks in 12-14 week old C57BL/6 mice. Each mouse received two implants in its dorsal region, each from a different construct. Implants were excised en bloc and prepared for histological analysis. Sections were stained with hematoxylin and eosin according to standard protocols. Additionally, samples were analyzed by immunohistochemistry, with antibodies against macrophage antigen-3 (Mac-3) (BD PharMingen), CD31 (Dianova), αSMA (Dako), and PCNA (Millipore). For quantifying cell invasion into intact slabs, histological sections were imaged in the central region of the implant (10×) and the number of cells per high power field (HPF) was quantified in Image J (n=4). For quantifying vascularity around powdered skin, three 40× images were taken per implant and the number and size of CD31+ and SMA+ lumens was quantified in Image J (n=6).

In Vitro Migration Through Cell-Derived Matrix

To probe mechanisms of enhanced cell penetration into intact slabs of TSP-2 null matrix, an in vitro assay was used in a similar manner to previous work (Krady, et al., American J. of Pathology, 173(3): 879-91, 2008). Briefly, primary dermal fibroblasts were isolated from WT or TSP-2 null mouse skin and 50,000 cells were seeded into the top chamber of a TRANSWELL® (Corning). Cells were cultured in the presence of 100 µM ascorbic acid for 7 days before decellularization with 40 mM NH4OH and 0.5% Triton X-100. Next, 50,000 fibroblasts isolated from either WT or db/db mice (serum starved overnight in 0.5% FBS) in 100 µl serum free media were added to the top of the TRANSWELLS®. 600 µl media with 10% FBS was added to the bottom of the well and cells were allowed to migrate at 37° C. for 6 hours, before being fixed in 100% methanol and stained with a Giemsa-May Grunwald stain, as described previously (Moore, et al., Acta Biomaterialia. 11:37-47, 2015). Wells were imaged at 20× and quantified by measuring the number of cells per image (n=5).

In Vivo Wound Healing in Diabetic Animals

Homozygous genetically diabetic 12-week-old, Lep/r db/db mice (B6.BKS(D)-Leprdb/J, Jackson) were used for wound experiments (Kobsa, et al. Biomaterials, 34(15): 3891-901, 2013: Kyriakides, et al., The Journal of Investigative Dermatology, 113(5):782-787, 1999). The day before surgery, hair was clipped and depilated (NAIR™). Animals were anesthetized with isothesia, and two symmetrical 6 mm full-thickness circular wounds were created on the dorsa of the animals using a biopsy punch (ACUPUNCH®). Wounds were covered with the appropriate constructs and sutured into place using Polysorb 4-0 suture (COVIDIEN®). The entire area was then covered with TEGADERM® (3M). TEGADERM® was sutured to the skin to ensure scaffolds remained hydrated.

At 10 days or 21 days, animals were euthanized and the wound area was excised together with the surrounding tissues for analysis. Wounds were fixed overnight in Z-FIX (Anatech) and prepared for histological analysis by bisecting the wound. Sections were stained with hematoxylin and eosin and Masson's Trichrome according to standard protocols. Additionally, samples were analyzed by immunohistochemistry, as described above (anti-vimentin from Millipore was also used). For quantifying cellular content of grafts, three 20× images were taken per implant and the number of vimentin+ cells and number and size of CD31+ and SMA+ lumens was quantified in ImageJ. For analysis of collagen remodeling, paraffin-embedded sections were analyzed as described by Hwang, et al. (Hwang, et al., Acta Biomater, 53 (2017) 268-278). Briefly, paraffin was removed by incubation in xylenes, and tissue was rehydrated in an ethanol series. Subsequently, sections were blocked in 5% goat serum for 20 minutes. Sections were stained with the collagen-hybridizing peptide and DAPI overnight at 4° C. as described above. Slides were washed three times with PBS and mounted with Vectashield Mounting Medium. For quantification, four 40× images were taken along the edge of the construct to examine collagen remodeling. Images were quantified for integrated intensity using ImageJ.

Scanning Electron Microscopy

To prepare samples for SEM, cross-sections of lyophilized skins were mounted to stubs with carbon tape, sputter-coated with iridium, and viewed via SEM (Hitachi SU-70).

Statistical Analysis

Data are expressed as the mean+the standard error of the mean (SOM). One-way ANOVA with Tukey's Multiple Comparisons test was used for all statistical analysis of data with more than two samples. For experiments where data was collected from only two samples, a two-tailed Students t-test was used. P-values <0.05 were considered statistically significant.

The results of the experiments on TSP-2 KO decellularization are now described in the following examples.

Figure 1A:
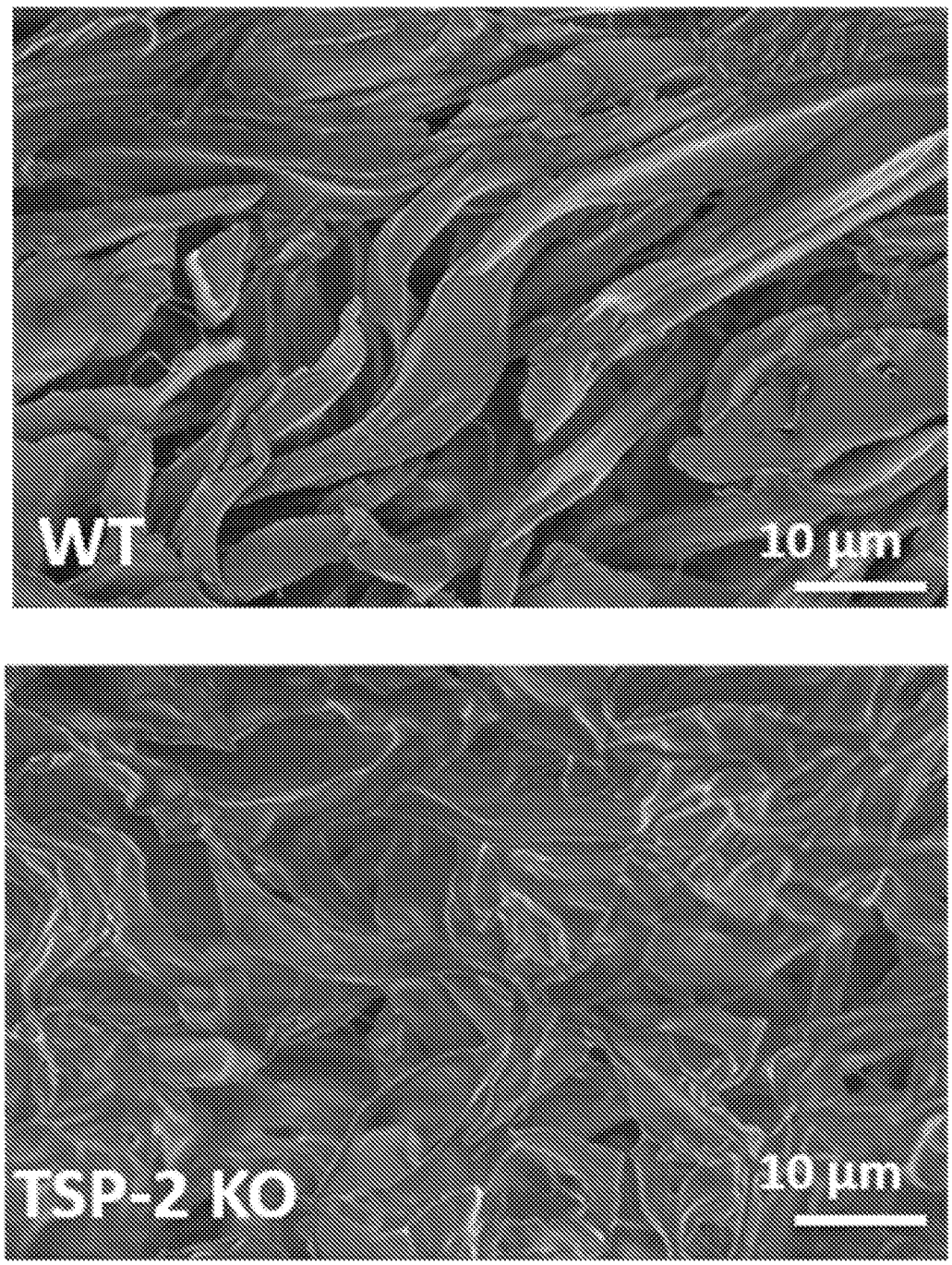
FIGS. 1A-1F show that TSP-2 KO ADM exhibited altered structure and mechanics.
Figure 1B:
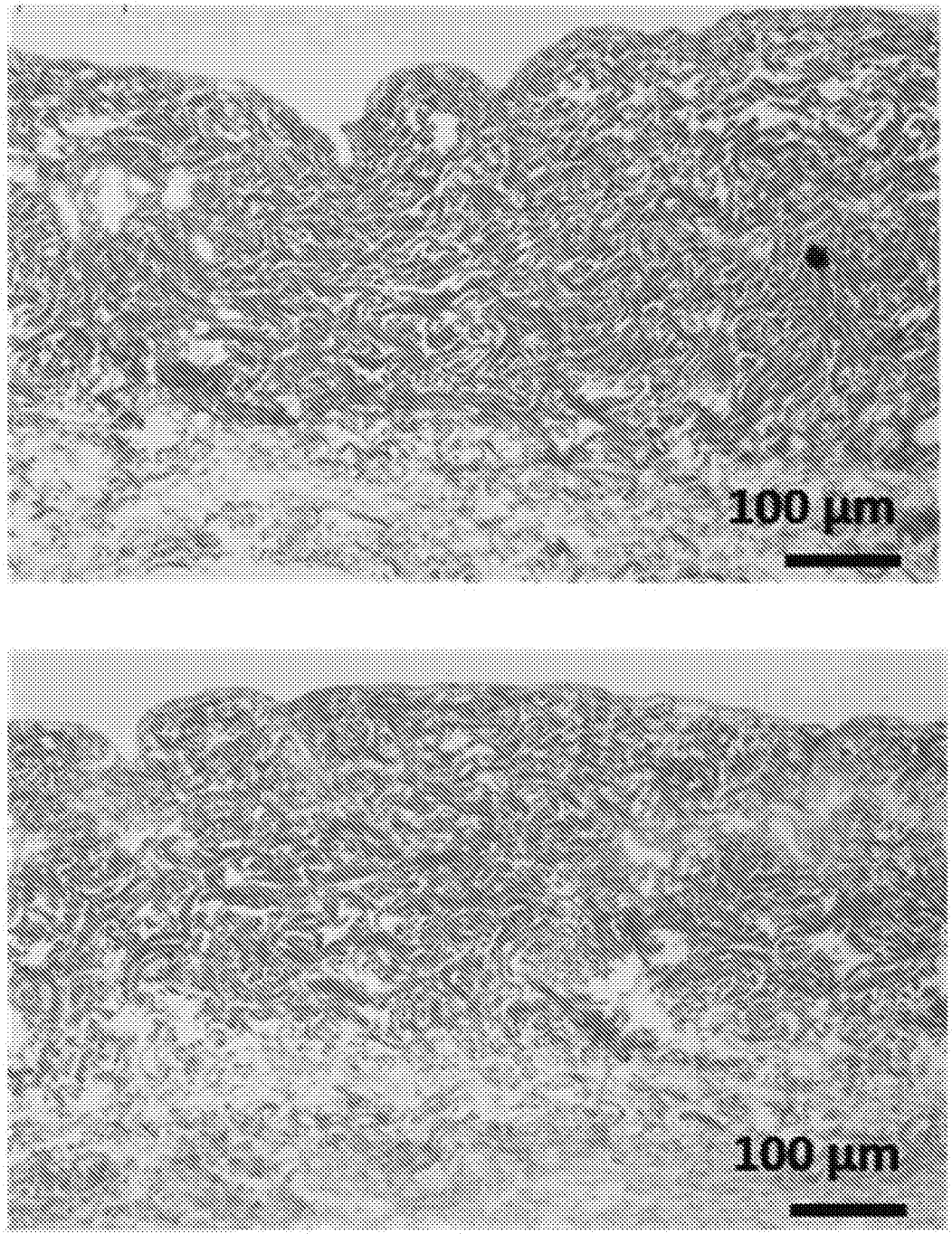
Figure 1C:
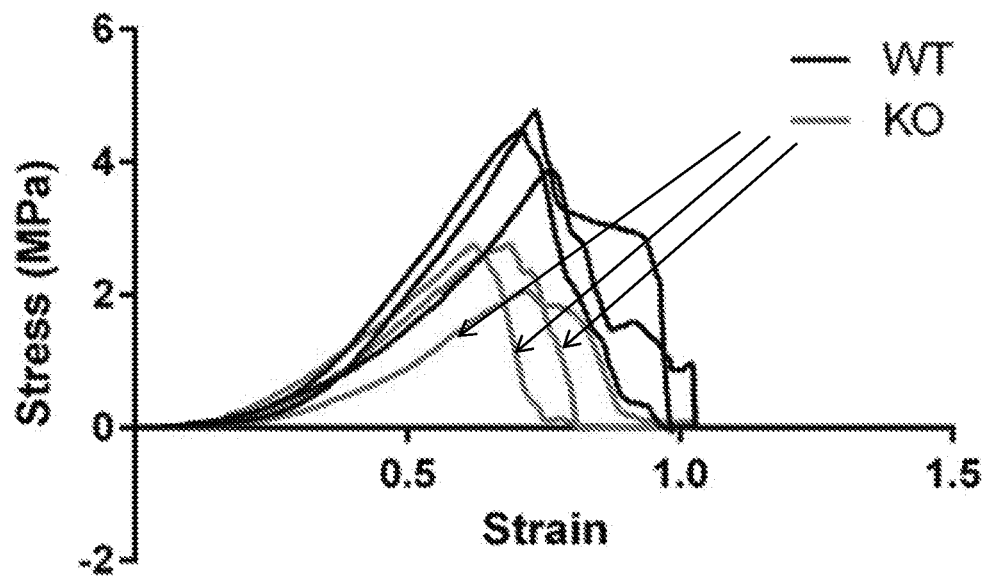
Figure 1D:
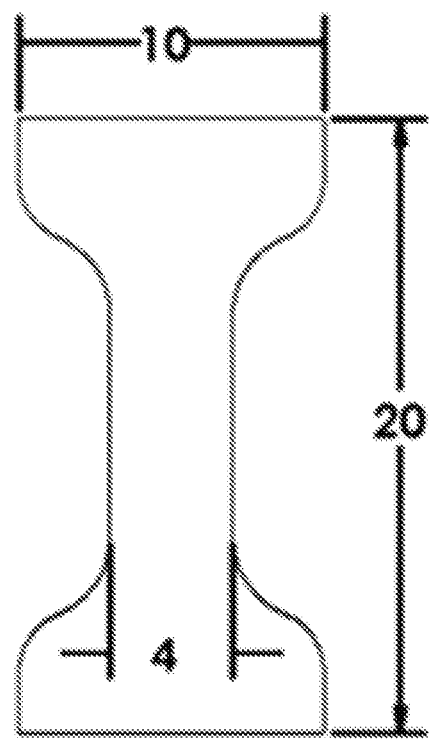
Figure 1E:
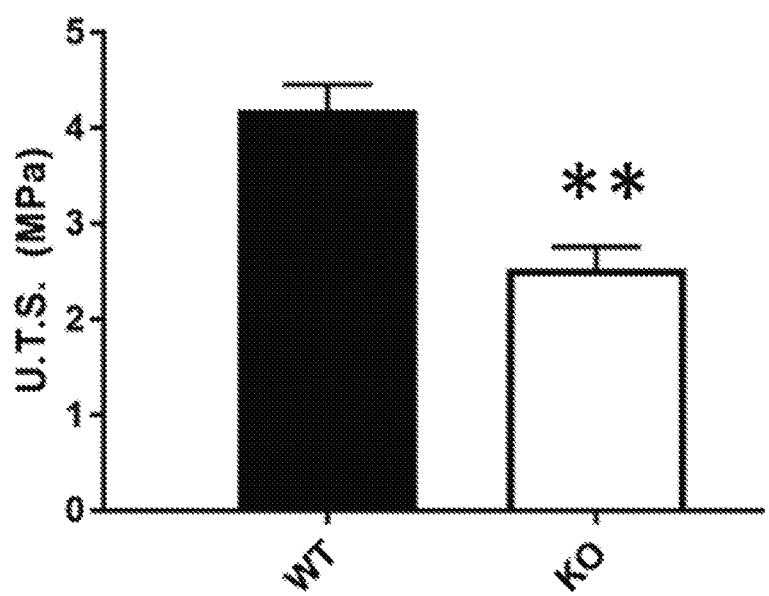
Figure 1F:
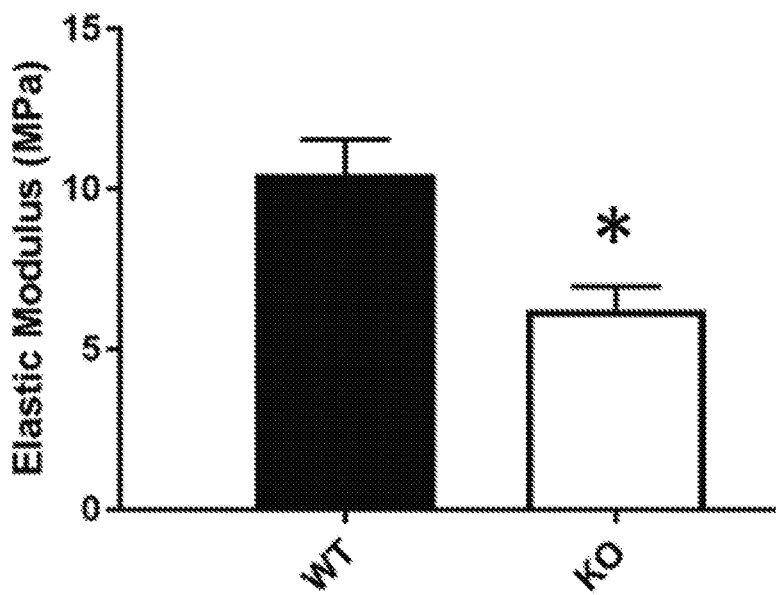

Example 1: Genetic Manipulation Alters Scaffold Structure and Mechanical Properties The decellularization process previously optimized for WT mouse skin was able to adequately decellularize TSP-2 KO skin as well (Morris, et al., *BioRe-search Open Access*, 5(1): 177-187, 2016). Decellularization resulted in removal of bulk cellular and nuclear material, which was clearly demonstrated by the lack of nuclear remnants on the hematoxylin and eosin (H&E) stained tissue (FIG. 1B). SEM demonstrated the basket-weave morphology of the dermis of the WT construct, contrasting with the less-organized morphology of the TSP-2 KO construct (FIG. 1A). Mechanical testing demonstrated a right shifted stress-strain curve with lower peaks at failure corresponding to reduced elastic modulus and ultimate tensile strength (U.T.S.) respectively (FIGS. 1C-1F).

Figure 2A:
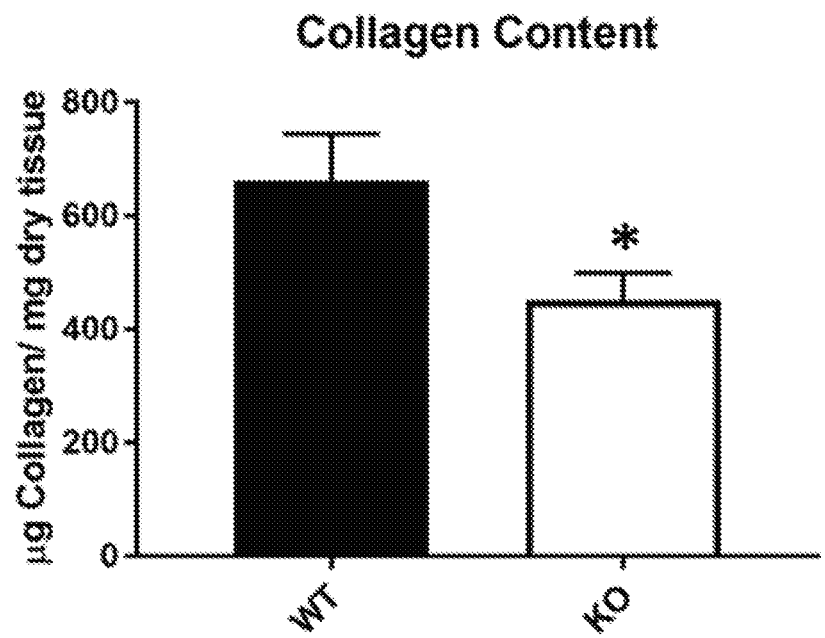
FIGS. 2A-2F are graphs showing that TSP-2 KO ADM exhibited reduced collagen content, but is otherwise biochemically similar to WT.
Figure 2B:
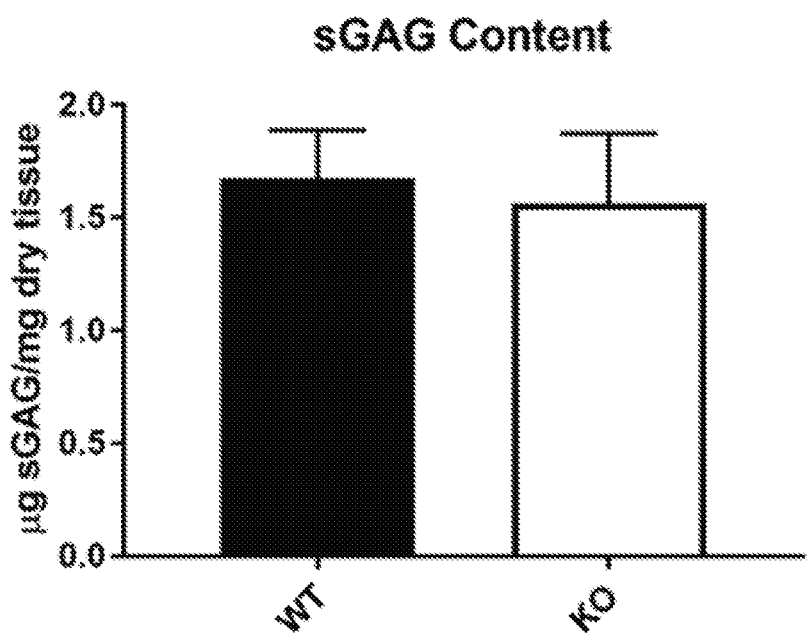
Figure 2C:
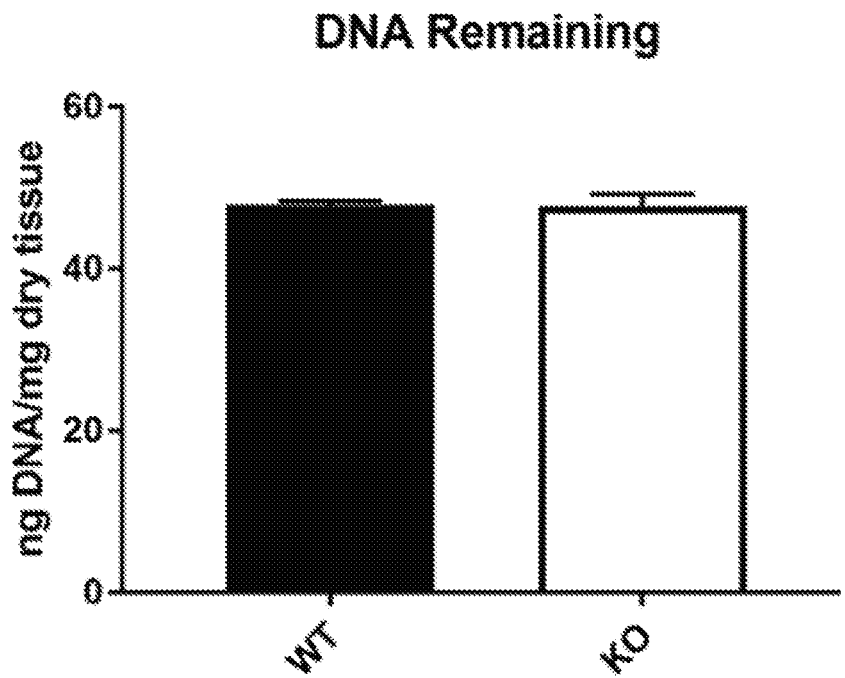
Figure 2D:
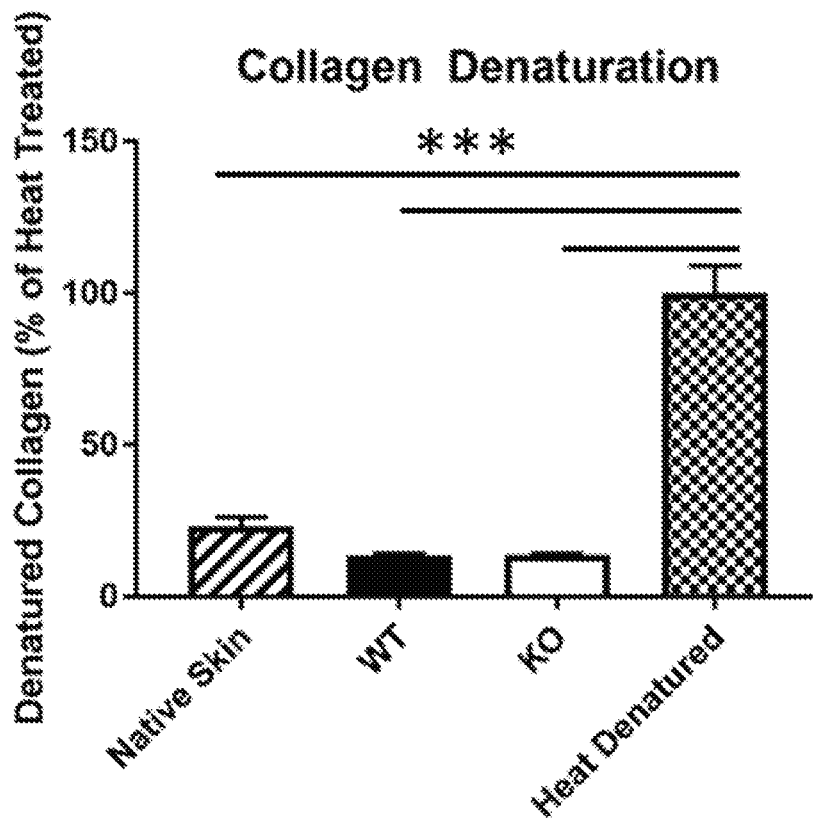
Figure 2E:
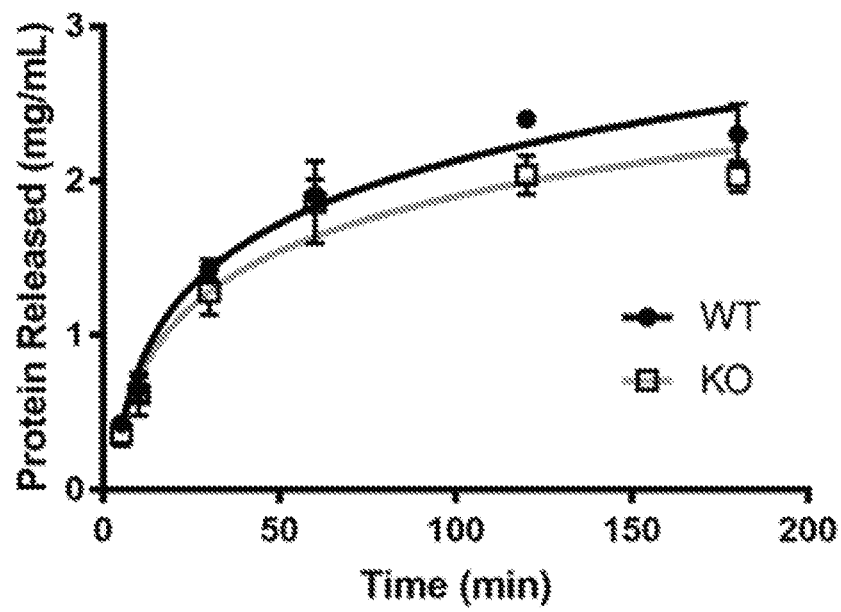
Figure 2F:
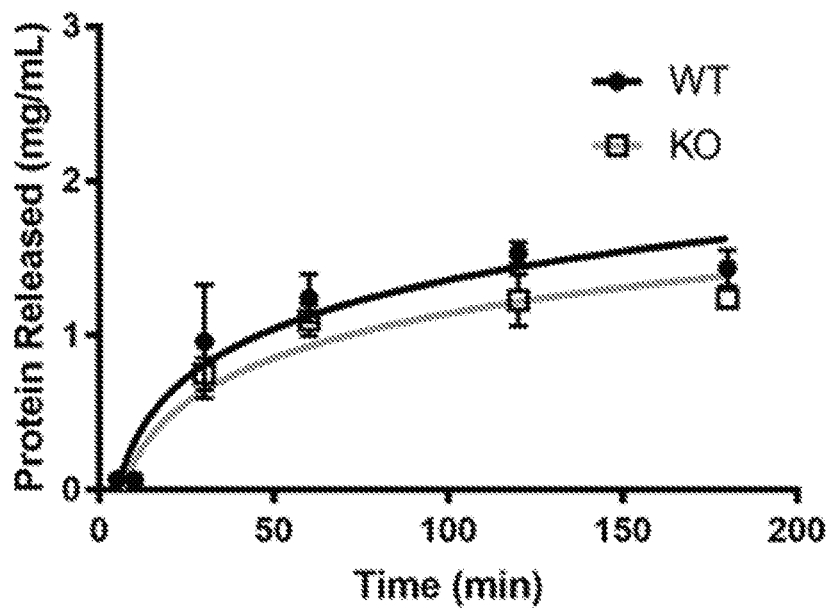
Figure 2G:
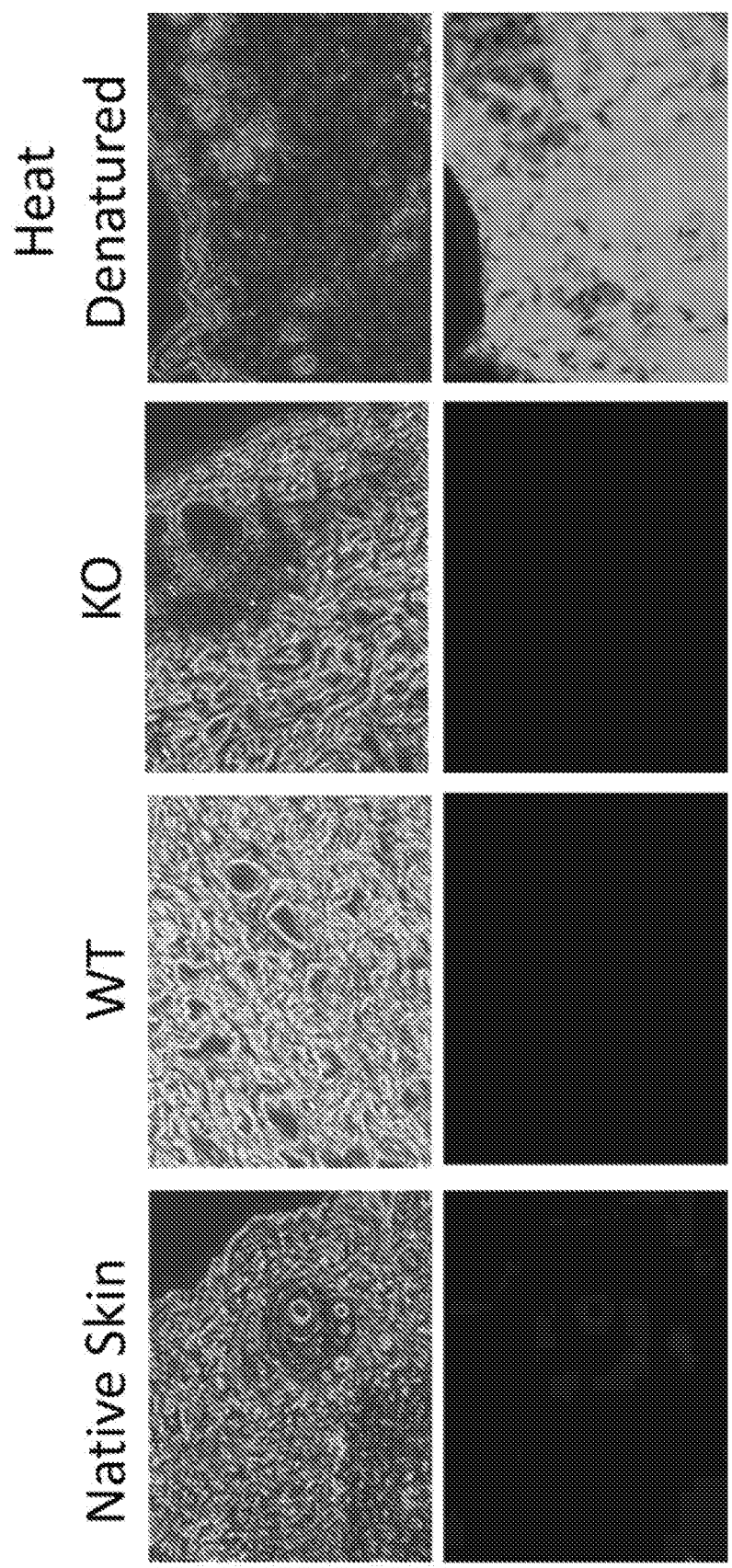
FIG. 2G is set of images of denatured collagen in ADM showing no changes between WT and KO. Denatured collagen was imaged in native skin, WT and KO ADM, and heat denatured native skin by incubation in a collagen-hybridizing peptide (bottom row). The WT and KO ADM showed almost no staining with minor background staining evident in the native skin. The heat denatured samples showed strong positive staining. Presence of material was verified by phase contrast imaging (top row).

Example 2: Composition, Denaturation Quantification, and Degradation Kinetics Collagen content was reduced in the TSP-2 KO construct as compared to WT (FIG. 2A), but sGAG and residual DNA content did not change with genotype (FIGS. 2B-2C). The similar residual DNA content was below the commonly accepted threshold of 50 ng dsDNA per mg ECM, and indicates that the tissues are equally well decellularized. Denatured collagen was quantified with a collagen hybridizing peptide using a previously published method (Hwang, et al., *Acta Bionaterialia*, 53:268-278, 2017). No difference was found in the total amount of denatured collagen between native skin, WT construct, or KO construct, but the heat denatured control demonstrated significantly more denaturation (FIG. 2D, FIG. 2G) Digestion of decellularized constructs in purified enzyme solution indicated that WT and TSP-2 KO acellular dermal matrix (ADM) have equal susceptibility to both collagenase and pepsin (FIGS. 2E-2F). In vivo degradation is cell mediated and thus enzyme susceptibility is not a perfect predictor of in vivo material lifetimes.

Example 3: Chemoattractant Properties of Degradation Products

Figure 3A:
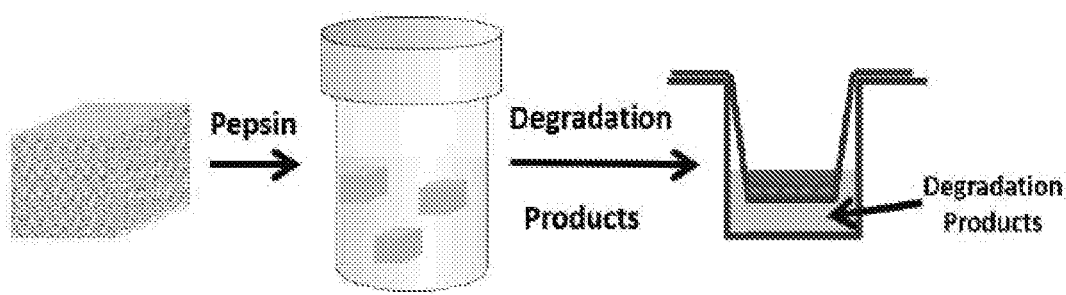
FIGS. 3A-3G are a scheme and graphs showing that TSP-2 KO degradation products induced chemotactic effects. Degradation products were prepared by incubating decellularized skin in a pepsin solution (FIG. 3A). Degradation products were added to serum-free media at a concentration of 50 μg/mL, and chemotaxis toward them was tested in a TRANSWELL®. NIH/3T3 embryonic fibroblasts (FIG. 3B) and MC3T3-E1 preosteoblasts (FIG. 3C) migration significantly increased toward TSP-2 KO matrix than the pepsin control. WT displayed no greater chemotaxis than control. HUVECs (FIG. 3D) and RAW 264.7 macrophages (FIG. 3E) displayed no chemotactic activity toward either degradation product (n=3).
Figure 3B:
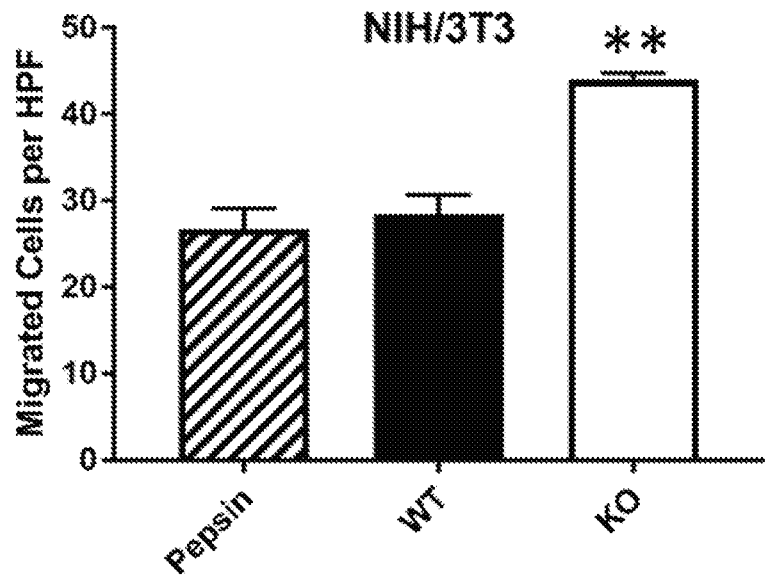
Figure 3C:
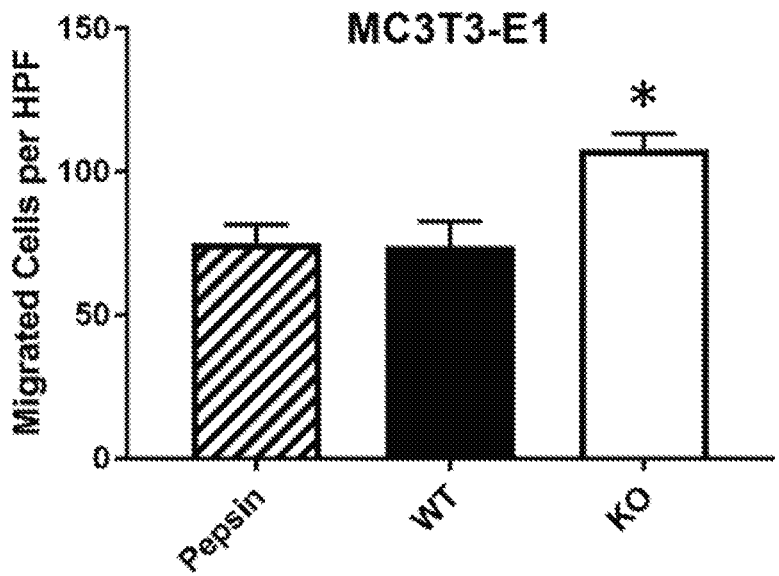
Figure 3D:
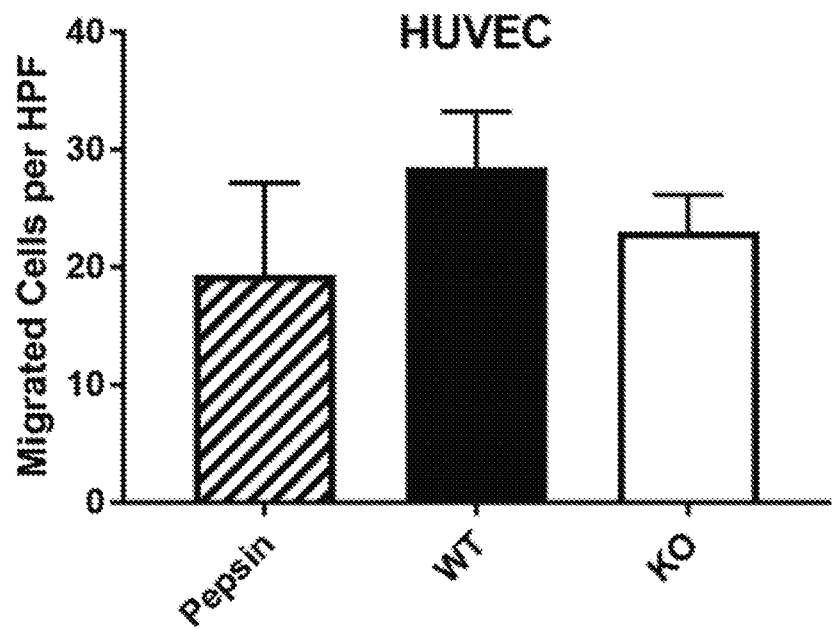
Figure 3E:
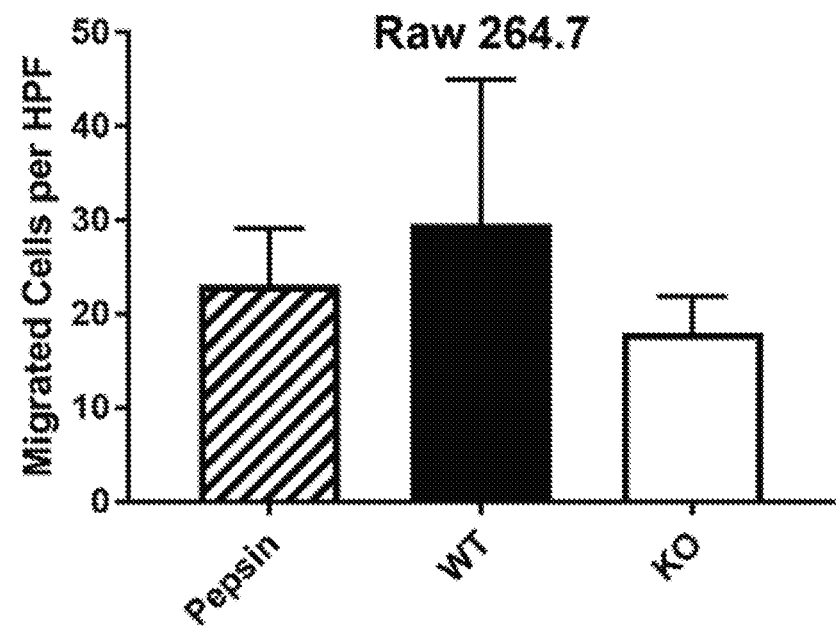
Figure 3F:
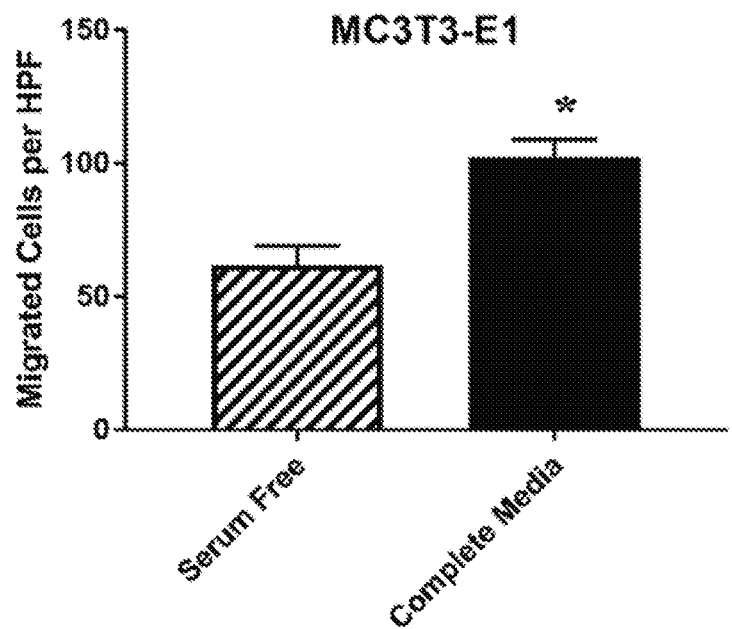
Figure 3G:
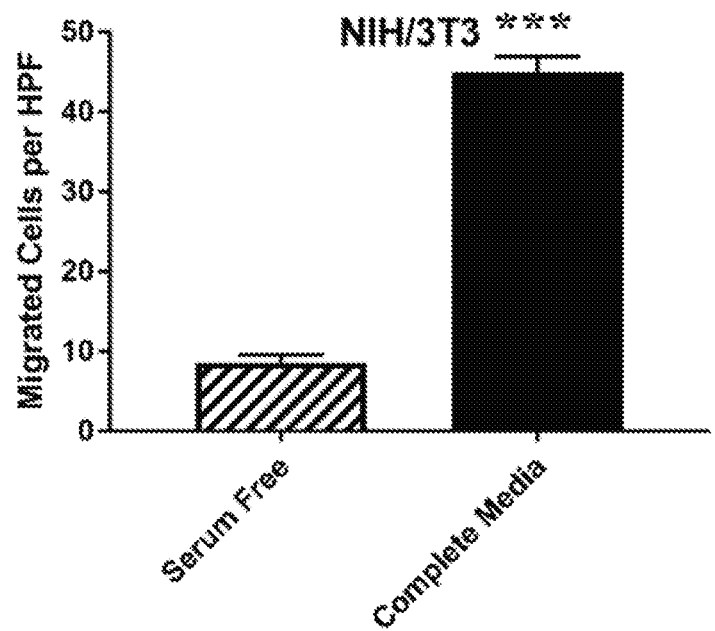
Figure 3H:
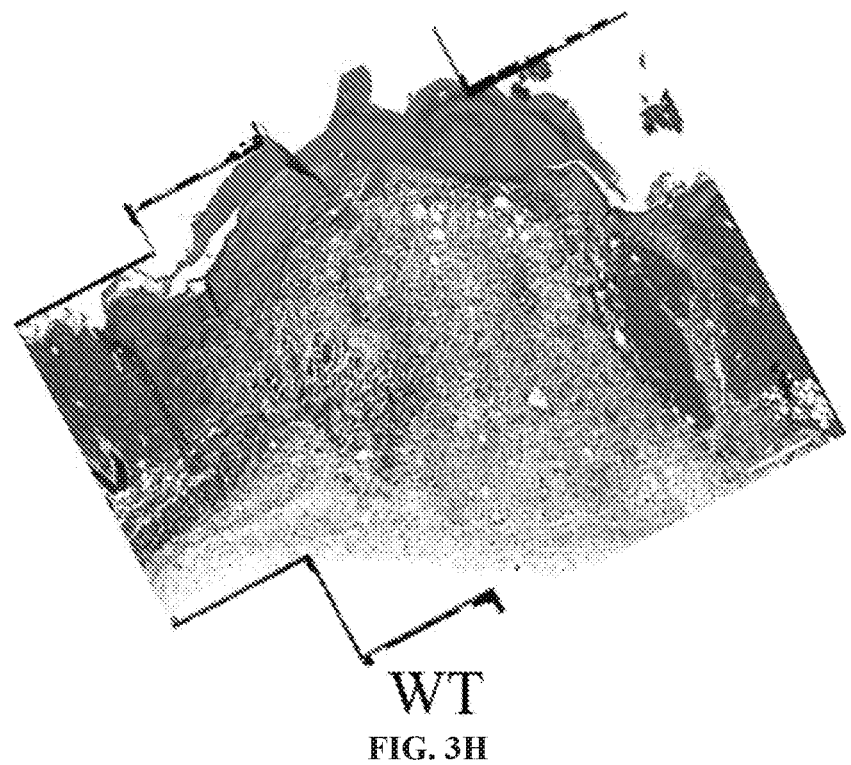
FIGS. 3H-3J are images and graphs showing that TSP-2 KO ADM accelerated wound healing in healthy mice when used as a wound covering. Decellularized skins were cut to match the size of the wounds, hydrated, sutured into place, and allowed to heal for 7 days before excision and histological staining for Masson's Trichrome (FIGS. 3H-3I). Quantification of Masson's Trichrome was performed by measuring the percent of the wound bed covered with dark blue pixels indicating mature collagen. Quantification demonstrates significantly more mature collagen in the wound beds that were covered with TSP-2 KO matrix (FIG. 3J). Results are given as mean+SEM, n=4, *p<0.05.
Figure 3I:
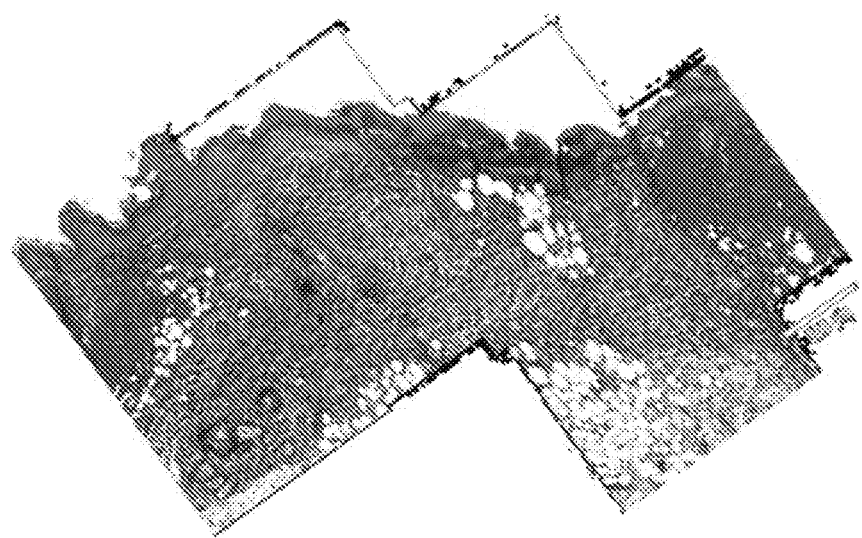
Figure 3J:
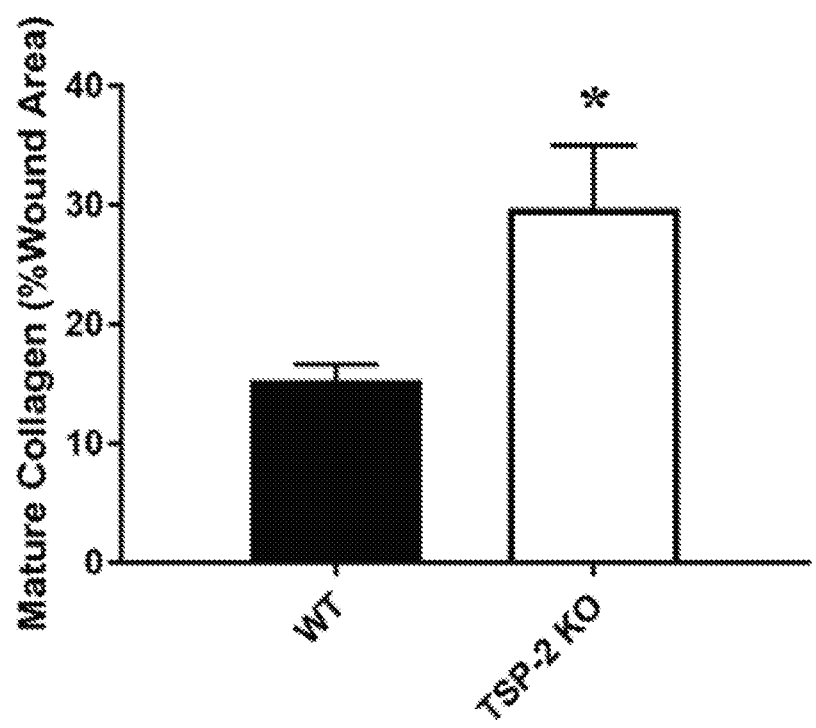

To test whether degradation products of the TSP-2 KO and WT materials had differential chemoattractant effects on cells, the materials were digested in pepsin to create degradation products which were added to media. This preparation was used as the chemoattractant solution in migration assays. Several cell types were selected including NIH/3T3 fibroblasts because they are an important cell type in skin homeostasis and secrete their own ECM. MC3T3-E1 preosteoblasts, another cell type that secretes extensive ECM in vitro, and HUVECs and RAW 264.7 cells because of the essential role of vascularization and inflammation in wound healing. Enhanced migration toward TSP-2 KO, but not WT degradation products, was observed for NIH/3T3 fibroblasts and MC3T3-E1 preosteoblastic cells (FIGS. 3B-3C). HUVECs and RAW 264.7 cells displayed no chemotaxis toward degradation products (FIGS. 3D-3E). Differential effects on different cell types indicated that the chemotactic effects of TSP-2 null ADM degradation products were cell-specific. In preliminary experiments, ADM were used as wound coverings for healthy WT mice, and the TSP-2 KO ADM demonstrated accelerated healing by 7 days post-implantation (FIGS. 3H-3J), suggesting the degradation products translated favorable chemoattractant properties to an in vivo setting.

Example 4: Comminuted ECM

Comminuted (or micronized) ECM is popular for use as a tissue filler and has been examined as an occlusive dressing for fingertip injuries (Gilbert, et al., *Biomaterials*, 26(12): 14315, 2005, Wise, et al., *Plastic and reconstructive surgery*, 120(5):1156-60, 2007: Dreifuss, et al., *Plastic and Aesthetic Research*, pages 2014-2015, 2015). To study the in-fluence of genetic manipulations on the host response to comminuted ECM, silicone trays were used to implant decellularized skin that had been comminuted (herein referred to as WT or KO powder), subcutaneously (FIGS. 4A-4B). The trays were necessary because retrieving powder after in vivo application in the subcutaneous space was challenging. After two weeks, trays with the ECM were retrieved. H&E stained sections containing the powdered ECM demonstrated that regardless of genotype, cells invaded throughout (FIG. 4B). Immunohistochemical staining for CD31 revealed more blood vessels around the TSP-2 KO powder than there were around the WT (FIGS. 4C-4D). The vessels were also larger around the KO powder than the WT (FIGS. 4C and 4F). Additionally, there were more αSMA-positive blood vessels around the TSP-2 KO powder (FIGS. 4D and 4G). Together, the CD31 and αSMA stains demonstrate enhanced vascularization and vessel maturation around the TSP-2 KO powder.

Example 5: Enhanced Cell Migration in TSP-2 Null ECM

To examine the host response to ADM, 4 mm slabs of intact decellularized skin were implanted subcutaneously in mice in silicone trays for 14 days. After excision and staining with H&E, it was observed that more cells migrated into TSP-2 KO ECM compared to WT (FIGS. 5A-5C). To investigate this mechanism in vitro, primary dermal fibroblasts were isolated from WT or TSP-2 KO mice and cultured on TRANSWELLS® to produce a layer of cell-derived matrix (CDM) (FIG. 5D). This CDM was decellularized and either primary WT fibroblasts or fibroblasts isolated from the genetically diabetic db/db mouse were seeded on top of the matrix in serum-free media. Serum containing media was added to the bottom of the well, and migration through the matrix quantified. In both cases (VT or db/db fibroblasts) the TSP-2 null matrix was more permissive to fibroblast migration (FIGS. 5E-5F). This data is consistent with previous findings demonstrating that TSP-2 KO matrix is more permissive for endothelial cell migration (Krady, et al., *The American journal of pathology*, 173(3): 879-91, 2008).

Example 6: Diabetic Wound Healing with ADM Grafts

As shown elsewhere herein, TSP-2 KO constructs demonstrate characteristics that are functionally distinct from VT including altered structure, degradation products, mechanics, and host response. Enhanced cell invasion into TSP-2 KO ECM makes it a useful material in a regenerative medicine setting where faster cell infiltration is generally considered a positive phenomenon (Lopresti and Brown. *Host Response to Biomaterials: The Impact of Host Response on Biomaterial Selection*, pages 53-73. Academic Press, 2015; Morris, et al., *Advanced Healthcare Materials*, 1700370:1700370, 2017). Utility in a compromised wound healing scenario, such as diabetic wound healing, was used fully evaluate the material in a regenerative context. Slabs of ADM were rehydrated in PBS and sutured into full thickness wounds of the genetically diabetic db/db mouse. After 10 days, the TSP-2 KO ADM integrated better with the surrounding tissue, to the point where the border between graft and normal tissue could not be discerned (FIG. 6C). Analysis of collagen demonstrated that the TSP-2 KO constructs underwent more remodeling at 10 days as compared to the WT (FIGS. 6A-6B). At 10 days, more vimentin-positive cells, a marker of cells of a mesenchymal lineage, were present within the TSP-2 KO construct than the WT, but by 21 days there was no longer a difference (FIGS. 6E-6F). At both time points (10 and 21 d), there were more αSMA-positive vessels within the TSP-2 KO construct, indicating more vessel maturation (FIGS. 6G-6H). There was no difference in CD31 staining at either time point (FIG. 6D).

The results presented in Examples 1-6 demonstrate that genetic manipulations can serve as a toolbox to impart tunability to ECM-based materials that result in increased functional performance. It has been demonstrated that tissues from a genetically modified mouse can be decellularized with techniques already in use for WT tissues, and that the resulting material exhibits altered structural and thus mechanical properties. Both structure and mechanics are central to the function of any material, and the ability to manipulate these properties is one advantage that synthetic materials currently retain over decellularized ECM. Additionally, although the modified biomaterial exhibits only subtle biochemical differences, its degradation products have a pronounced chemoattractant effect on specific cell types.

Materials and Methods for Examples 7-11

Cell Culture

Cells were maintained in vitro with standard protocols. Briefly, the mouse embryonic fibroblast cell line NIH/3T3 (ATCC) and mouse preosteoblastic cell line MC3T3-E1 were cultured in their respective growth media, DMEM and MEMα, supplemented with 10% FBS and 1% pen strep.

Hydrogel Preparation

ECM was solubilized by incubating decellularized WT or KO skin at 10 mg dry weight per mL fluid in a solution of 1 mg/mL pepsin in 0.01 N HCl (Sigma) for 72 hours as previously reported (Wolf et al., *Biomaterials*, 33(29):7028-38, 2012: Freytes et al., *Biomaterials*, 29(11):1630-1637, 2008; Singelyn et al., *Biomaterials*, 30(29):5409-5416, 2009). The solubilized ECM was neutralized and buffered with sodium hydroxide (1/10 digest volume) and 10×PBS (1/9 digest volume). To prepare tissue-derived hydrogels, buffered and solubilized ECM was diluted to a final concentration of 8 mg/mL with PBS to form the pre-gel solution, and stored on ice until use. 1:1 ratios of WT:KO gel were also prepared by mixing this solution of tissue-derived hydrogel in equal volumes.

For the preparation of hydrogels from CDM, MC3T3-E1 cells were cultured at confluence in the presence of 100 μM ascorbic acid and 4 μM inositol hexakisphosphate (IP6—to prevent matrix mineralization) for 10 days (Addison and McKee, *Bone*, 46(4):1100-7, 2010). Cells were decellularized with 40 mM $NH_4OH$ and 0.5% Triton X-100 for 1 minute and washed extensively with PBS. The ECM was rinsed with deionized water, scraped with a cell scraper into scintillation vials, and lyophilized. Hydrogels were prepared by incubating ECM at a concentration of 10 mg dry weight per mL fluid in a solution of 1 mg/mL pepsin in 0.01 N HCl (Sigma) for 24 hours before neutralization and buffering as described above.

Subcutaneous Injections

Subcutaneous injection of tissue-derived hydrogels was performed by injecting 250 μL of pre-gel (kept on ice) SC for 5 days in 12-14 week old C57BL/6 mice. Each mouse received two injections in its dorsal region, each from a different genotype of gel (WT, KO, or 1:1). Implants were excised with surrounding tissue intact, fixed in Z-FIX (Anatech), and embedded in paraffin for sectioning. Sections were stained with hematoxylin and eosin according to standard protocols, as well as immunohistochemically for vimentin (EMD Millipore). For analysis of cell penetration, three 20× images were taken per injection and the average number of cells per high power field was quantified, n=8.

In Vivo Wound Healing in Diabetic Animals

Homozygous genetically diabetic 12-week-old, Lep/r db/db mice (B6.BKS(D)-Leprdb/J, Jackson) were used for wound experiments (Kobsa, et al. *Biomaterials*, 34(15): 3891-901, 2013; Kyriakides, et al., the *Journal of Investigative Dermatology*, 113(5):782-787, 1999). The day before surgery, hair was clipped and depilated (Nair). Anesthesia was induced with isoflurane, and two full-thickness wounds were created on the dorsa using a 6 mm biopsy (Acupunch). Wounds were covered with 40 μL of pre-gel, which filled the wound and gelled in situ, and the entire area was then covered with TEGADERM® (3M) which was secured in place by sutures.

At 10 days or 21 days, animals were euthanized and the wound area was excised and prepared for analysis as described above. Sections were stained with hematoxylin and eosin according to standard protocols. For quantification of hydrogel treated wounds, 10× images were stitched to cover the entire wound width. Wound width and epithelial gap were measured in ImageJ. Epithelial thickness and un-remodeled gel thickness were determined by measuring at 5 locations throughout the wound for each wound. Additionally, samples were analyzed via immunohistochemistry with anti-CD31 (Dianova) and anti-αSMA (Dako) antibodies. For quantifying cellular content of hydrogels after implantation in wounds, ImageJ was used to quantify the number of vimentin+ cells and the number and size of CD31+ and SMA+ lumens. Three 20× images were quantified per implant.

Gene Delivery to MC3T3-E1 Cells

To create a stable cell line with reduced TSP-2 expression, a plasmid encoding a TSP-2 shRNA or its vector control (pSHAG Magic vector) was transfected into MC3T3-E1 cells with Lipofectamine. Cells were then selected in puromycin (20 μg/mL, ThermoFisher) to create a stable cell line. Reduction in TSP-2 expression was confirmed via Western Blot.

Turbidimetric Gelation Kinetics

Hydrogel gelation kinetics were measured in a similar manner to that described previously (Wolf, *Biomaterials*, 33(29):7028-38, 2012), Briefly, 100 μL of neutralized hydrogel solutions at a concentration of 4 mg/mL were loaded into wells of 96 well plates on ice. Plates were then placed in a plate reader that was preheated to 37° C. and gelation was tracked spectrophotometrically at 415 nm. Experiments were conducted at 4 mg/mL because at higher concentrations the solution was too turbid at time, t=0 to get accurate measurements. Readings were normalized with the following equation, where $A_o$ is the initial absorbance, Amax is the maximum absorbance, and A is a given absorbance measurement (Wolf, Biomaterials, 33(29):7028-38, 2012):

$$\text{Normalized Absorbance} = \frac{A - A_0}{A_{max} - A_0}$$

Additionally, $t_{1/2}$ was calculated as the time to reach 50% absorbance (n=5).

Scanning Electron Microscopy

To prepare samples for SEM, 250 µL of hydrogel precursor solution was added to cloning rings and gelled at 37° C. for 1 hour. Hydrogel samples were then fixed in 2.5% paraformaldehyde in 0.1M cacodylate buffer, dehydrated with an ethanol gradient, incubated in hexamethyldisilazane, and air dried. All samples were sputter-coated with iridium, and viewed via SEM (Hitachi SU-70).

Rheology

Rheology was performed with an AR2000 rheometer (TA Instruments) with a 25 mm parallel plate geometry. The gap height was set to 700 µm (350 µm for CDM). ECM pre-gel was pipetted onto the rheometer plate which was maintained at a temperature of 10° C. using the Peltier temperature controller. Mineral oil was added to the edge to reduce evaporation of the samples. Temperature was increased stepwise by 1 degree and allowed to stabilize for 15 seconds before a measurement was taken. This procedure was followed until the temperature reached 37° C. at which point the temperature was maintained to induce gelation. A frequency of 1 Hz and 3% strain were used to conduct measurements.

SDS-PAGE

ECM pre-gel was analyzed by SDS-PAGE on a Tris-HCl 10% polyacrylamide gel (Bio-Rad). 50 µg solubilized ECM was added to each lane and compared against the Precision Plus Dual Color Ladder (Bio-Rad). Gels were stained with Coomassie blue and imaged with a LICOR infrared scanner.

Proteomics

Chloroform-methanol:water protein precipitation was performed on buffered hydrogel precursor solution, and dried protein pellet was resuspended in RAPIGEST™ (Waters Inc) containing 50 mM ABC, reduced with DTT alkylated with iodoacetamide, and dual enzymatic digestion with LysC and trypsin (carried out at 37° C. for 4 hrs), respectively. Digestion incubation was continued overnight (16 hrs) and subsequently quenched (with 0.1% formic acid) during the de-salting step with C18 UltraMicroSpin columns. The effluents from the de-salting step were dried and re-dissolved in 5 µl 70% FA and 35 µl 0.1% TFA. An aliquot was taken to obtain total digested protein amount. A 1:10 dilution of Pierce Retention Time Calibration Mixture was added to each sample prior to injecting on the UPLC Q-Exactive Plus mass spectrometer for normalization of LFQ data.

Label-Free Quantitation (LFQ) was performed on a Thermo Scientific Q-EXACTIVE® Plus Mass spectrometer connected to a Waters NANOACQUITY UPLC® system equipped with a Waters Symmetry C18 180/µm 20 mm trap column and a 1.7-µm, 75 µm 250 mm NANOACQUITY UPLC® column (35C). The digests was diluted to 0.05 µg/µl with 0.1% TFA prior to injecting 5 µl of each duplicate analysis in block randomized order. To ensure a high level of identification and quantitation integrity, a resolution of 60,000 was utilized for MS and 15 MS/MS spectra was acquired per MS scan using HCD. All MS (Profile) and MS/MS (centroid) peaks were detected in the ORBITRAP™. Trapping was carried out for 3 min at 5 l/min in 99% Buffer A (0.1% FA in water) and 1% Buffer B ((0.075% FA in acetonitrile (ACN)) prior to eluting with linear gradients that will reach 30% B at 140 min, 40% B at 155 min, and 85% B at 160 min. Two blanks (1st 100% ACN, 2nd Buffer A) will follow each injection to ensure against sample carry over.

The LC-MS/MS data was processed with Progenesis QI Proteomics software (Non-linear Dynamics, version 2.3) with protein identification carried out using the Mascot search algorithm. The Progenesis QI software performed feature/peptide extraction, chromatographic/spectral alignment (one run was chosen as a reference for alignment), data filtering, and quantitation of peptides and proteins. A normalization factor for each run was calculated to account for differences in sample load between injections as well as differences in ionization. The normalization factor was determined by comparing the abundance of the spike in Pierce Retention Time Calibration mixture among all the samples. The experimental design was setup to group multiple injections from each run. The algorithm then calculates the tabulated raw and normalized abundances, maximum fold change, and Anova p values for each feature in the data set. The MS/MS spectra was exported as .mgf (Mascot generic files) for database searching. The Mascot search results was exported as .xml files using a significance cutoff of p<0.05 and FDR of 1% and then imported into the Progenesis QI software, where search hits was assigned to corresponding peptides. Relative protein-level fold changes was calculated from the sum of all unique, normalized peptide ion abundances for each protein on each run.

In Vitro Migration Assay

The mouse embryonic fibroblast cell line NIH3T3 (ATCC) was maintained in growth medium, DMEM (Gibco) with 10% FBS and 1% pen strep.

To perform in vitro migration assays, 200 µL of hydrogel was added to the top of TRANSWELL® inserts with 0.4 µm pores. The TRANSWELLS® were incubated for 45 minutes at 37° C. before 50,000 NIH3T3 fibroblasts were seeded on top in 100 µL of serum free media. To the bottom of the well, 600 µL of media containing 10% FBS was added. The cells were allowed to migrate for 24 hours before they were fixed with Z-FIX, embedded in paraffin, and sectioned and stained with H&E. Each section was examined and imaged where cells had penetrated the gels the furthest. Distance migrated was quantified using ImageJ, n=5.

Statistical Analysis

Data are expressed as the mean+the standard error of the mean (SOM). One-way ANOVA with Tukey's Multiple Comparisons test was used for all statistical analysis of data with more than two samples. For experiments where data was collected from only two samples, a two-tailed Students t-test was used. P-values <0.05 were considered statistically significant.

The results of the experiments on tissue derived hydrogels as tunable ECM materials are now described in the following examples.

Example 7: Genetic Manipulation Imparts Tunability to Tissue-Derived Hydrogels

Tissue-derived hydrogels were prepared from decellularized WT and TSP-2 KO mouse skin by pepsin solubilization followed by neutralization and warming to 37° C. (FIG. 7A). Both WT and TSP-2 KO hydrogels formed intact hydrogels with fibrillar structures (FIGS. 7D-7E). Turbidimetric determination of gelation kinetics indicated a sigmoidal gelation curve regardless of genotype (FIG. 7B). KO gels gelled slower than WT, and a 1:1 mixture had intermediate gelation times (FIG. 7C). Rheology demonstrated a clear distinction in mechanical properties between the WT and TSP-2 KO gels. The gels exhibited similar kinetics of gel stiffening, but the TSP-2 KO gel had a reduced storage modulus as compared to WT (FIGS. 7F-7G). A 1:1 mixture of WT and TSP-2 KO gel demonstrated a storage modulus that was reduced compared to WT but increased compared to TSP-2 KO, demonstrating that genetic modification of source tissue can yield a tunable tissue-derived hydrogel system through simple mixing (FIGS. 7F-7G). Additionally, gels with lower ECM concentration exhibited similar trends with WT having the largest storage modulus and TSP-2 KO having the smallest (FIGS. 7I-7J). There was no significant change in the rate at which molecules of various sizes (from small molecules through large proteins) diffused through these materials suggesting that these gels can potentially provide a drug delivery system with tunable mechanics, and consistent drug delivery profiles (FIGS. 7K-7N).

Example 8: Protein Content

WT and TSP-2 KO hydrogels displayed altered mechanical properties, prompting in depth analysis of the protein content of each gel. SDS-PAGE analysis indicated that the gels were composed largely of collagen, but that the TSP-2 KO gel exhibited qualitatively less collagen than WT (FIG. 8A). This is consistent with findings reported in Example 2. Proteomic analysis demonstrated significant differences in 11 proteins between WT and TSP-2 KO gels, most of which were collagens (FIG. 8B-8C). The alpha 4 chain of collagen 4 and the alpha 1 chain of collagen 6 were both increased in the TSP-2 KO gels, but various other collagens were contained at higher levels within the WT (FIG. 8C).

Example 9: Subcutaneous Injections

To assess tunability of the host response by genetic manipulation, hydrogels were injected subcutaneously into healthy mice and retrieved 5 days later. H&E staining of hydrogel sections showed that there was increased cell penetration into TSP-2 KO gels compared to WT (FIG. 9A). There were significantly more cells able to invade the 1:1 WT/KO gel than the WT, and significantly more in TSP-2 KO gel than in the 1:1 mixture. Furthermore, the TSP-2 KO and 1:1 hydrogels promoted increased cell migration into the depth of the gel (FIG. 9C). Immunohistochemical detection of vimentin indicated the presence of cells of a mesenchymal lineage (FIG. 9B). These findings mimic the in vitro observation that NIH/3T3 fibroblasts penetrated further into TSP-2 KO hydrogels than WT (FIGS. 9E-9F) and suggest that through genetic manipulation of TSP-2, it is possible to tune an aspect of the host response to a hydrogel: cell invasion.

Example 10: Wound Healing with Hydrogels

To assess whether tunable hydrogels would demonstrate utility in a regenerative medicine setting, they were applied to full thickness wounds in diabetic db/db mice for 10 and 21 days (FIGS. 10A-10I and 11A-11E, respectively). By 10 days, the wounds had begun to heal and epithelialization was visible over the tissue derived hydrogels; additionally, qualitatively more cells penetrated into the TSP-2 KO gels (FIGS. 10A-10B). Wounds treated with TSP-2 KO gel demonstrated a smaller epithelial gap compared to untreated wounds or WT gel, suggesting improved healing (FIG. 10C). Furthermore, TSP-2 KO gel displayed decreased thickness by 10 days, suggesting increased remodeling (FIG. 10D). TSP-2 KO gel promoted vascularization of the surrounding wound bed by 10 days, demonstrating increased CD31+ lumen presence, size, and stabilization by smooth muscle cells (FIG. 10E-10I). By 21 days, all wounds had closed (FIG. 11A-11C), but TSP-2 KO hydrogel-treated wounds demonstrated decreased epithelial thickness (an indicator of maturity of a healed wound) compared to untreated control (FIG. 11D). Additionally, the width of the wound bed was reduced in wounds treated with TSP-2 KO gel (FIG. 11E). Overall, treatment of diabetic wounds with TSP-2 KO hydrogel demonstrated improved wound healing associated with improved epithelialization, gel remodeling, vascularization, and ultimately a reduction in the overall size of the wound bed.

Example 11: Genetic Tunability of CDM

As demonstrated in Examples 1-11, genetically tunable tissue-derived hydrogels establish a method of providing bottom-up tunability to ECM-based materials that can control material properties and enhance their regenerative potential. However, screening various genetic manipulations for advantageous benefit requires genetically engineered animals and clinical translation using these methods would require the creation of genetically engineered large animals. Cell-derived matrix (CDM) has provided an alternative to tissue-derived ECM in applications where enhanced customizability (such as alterations in source species of ECM or mechanical conditioning) is desired. CDM can be produced by cells from a desired species (including human) in a number of culture conditions, and can even be genetically modified to include exogenous factors (Bourgine, et al., *Adv. Funct. Mater,* 2017). Therefore, hydrogels derived from CDM provide an opportunity to overcome the obstacles associated with discovery of novel genetic manipulations and translation of tissue-derived hydrogels. MC3T3-E1 pre-osteoblasts were chosen to construct CDM hydrogels because they produce a robust collagenous ECM in vitro. TSP-2 expression of MC3T3-E1 was knocked down via transfection with an anti-TSP-2 shRNA in a pSHAG-MAGIC vector (or vector control) as described previously (Bancroft, et al. *J. Biol. Chem.* 2015, 290 (1), 409-422.). Stable cell lines were created via selection in puromycin and TSP-2 KD was confirmed via western blot (FIG. 12A). A western blot for collagen indicated similar findings to tissue-derived hydrogels, demonstrating that the TSP-2 KD gel exhibited qualitatively less collagen than the vector control (FIG. 12B). SDS-PAGE was used to demonstrate similar overall protein makeup of the gels, with the gels consisting largely of collagen (FIG. 12E). Rheologically, CDM gels exhibited similar trends to their corresponding tissue-derived hydrogels with the TSP-2 KD gel having reduced storage modulus as compared to the pSHAG control (FIGS. 12C-12D). Although the CDM gels had lower overall storage moduli than the tissue-derived gels, they exhibited a similar genetic tunability.

Example 12

The present invention provides tunable ECM derived materials created using genetic manipulation. As shown herein, decellularized skin from WT and TSP-2 null animals exhibit altered structural and mechanical properties, as well as a change in functionality in vivo. Furthermore, it is demonstrated herein that it is possible to prepare hydrogels from WT and TSP-2 null decellularized skin and that these gels form entangled fibrillar structures with similar kinetics. WT and TSP-2 null gels displayed significantly different mechanical properties by rheology, and importantly a 1:1 ratio of WT to TSP-2 KO hydrogel, prepared simply by mixing the two in equal parts, had intermediate mechanical properties. These results provide evidence that genetic manipulation of source animal tissue can enable the creation of mechanically tunable hydrogels, without adjusting ECM concentration.

The invention further provides hydrogels derived from CDM. When the source cells are genetically manipulated, similar phenotypes occur to what is observed for tissue derived hydrogels. This finding is important because it allows for more rapid genetic engineering of ECM derived hydrogels, since genetically manipulating animals is not necessary. Additionally, it could be performed with human or porcine cells to rapidly create genetically engineered matrix materials suitable for clinical translation.

The disclosures of each and every patent, patent application, and publication cited herein are hereby incorporated herein by reference in their entirety.

While the present invention has been disclosed with reference to specific embodiments, it is apparent that other embodiments and variations of the present invention may be devised by others skilled in the art without departing from the true spirit and scope of the invention. The appended claims are intended to be construed to include all such embodiments and equivalent variations.

What is claimed is:

1. A composition comprising a decellularized extracellular matrix (ECM) lacking thrombospondin-2 (TSP-2-null ECM) and a decellularized wild-type ECM produced by a wildtype cell that expresses TSP-2, wherein the TSP-2-null ECM is produced by a cell comprising a knock-out of the TSP-2 gene, wherein the cell comprising the knock-out of the TSP-2 gene does not express TSP-2, wherein a storage modulus of the composition is increased and decreased compared to the decellularized TSP-2-null ECM and the wildtype decellularized ECM, respectively.

2. The composition of claim 1, wherein the composition is a hydrogel composition.

3. The composition of claim 2, wherein the composition further comprises at least one therapeutic agent selected from the group consisting of an immunosuppressive agent, an anti-inflammatory agent, an antimetabolite, an antibiotic, an antibody, a growth factor, a cytokine, a gene therapy, and an immunomodulator.

4. The composition of claim 1, wherein the cell comprising the knock-out of the TSP-2 gene is a primary matrix-producing cell, a fibroblast, an osteoblast, or a smooth muscle.

5. The composition of claim 1, wherein the knock-out of the TSP-2 gene is obtained via at least one method selected from the group consisting of RNA interference (RNAi), small hairpin RNA (shRNA) transfection, and Clustered Regularly Interspaced Short Palindromic Repeats (CRISPRs).

6. The composition of claim 1, wherein the TSP2-null ECM is produced by the cell comprising the knock-out of the TSP-2 gene in an in vitro cell culture.

7. The composition of claim 2, wherein the hydrogel composition is made by a method comprising:
contacting the TSP-2-null ECM and the wild-type ECM each with an acid protease to form a digested TSP-2-null ECM and the wild-type ECM material, respectively;
forming the hydrogel composition from each of the digested TSP-2-null ECM material and the wild-type ECM material at a gelation temperature following neutralization of the digested TSP-2-null ECM material and the wild-type ECM, respectively; and
mixing each of the hydrogels formed in equal volumes to make the hydrogel composition.

8. The composition of claim 2, wherein the cell comprising the knock-out of the TSP-2 gene is a dermal fibroblast cell, an osteoblast cell, a cardiac fibroblast cell, a smooth muscle cell, a mesenchymal stem cell, or an embryonic stem cell.

9. The composition of claim 2, wherein the composition comprises a hydrogel comprising a 1:1 mixture of the TSP-2-null ECM and the wild-type ECM, respectively.

* * * * *